United States Patent
Theofilos

(10) Patent No.: US 11,998,244 B2
(45) Date of Patent: Jun. 4, 2024

(54) MINIMALLY INVASIVE SURGERY ADD ON SCREW SYSTEM

(71) Applicant: SNJ Patents, LLC, Palm Beach Gardens, FL (US)

(72) Inventor: Charles Theofilos, Palm Beach Gardens, FL (US)

(73) Assignee: SNJ Patents, LLC, Palm Beach Gardens, FL (US)

( * ) Notice: Subject to any disclaimer, the term of this patent is extended or adjusted under 35 U.S.C. 154(b) by 0 days.

(21) Appl. No.: 17/717,069

(22) Filed: Apr. 9, 2022

(65) Prior Publication Data

US 2023/0293207 A1 Sep. 21, 2023

Related U.S. Application Data

(60) Provisional application No. 63/172,756, filed on Apr. 9, 2021.

(51) Int. Cl.
*A61B 17/70* (2006.01)
*A61B 17/86* (2006.01)
*A61B 17/00* (2006.01)

(52) U.S. Cl.
CPC ...... *A61B 17/7032* (2013.01); *A61B 17/8685* (2013.01); *A61B 17/00234* (2013.01)

(58) Field of Classification Search
CPC ............ A61B 17/7032; A61B 17/8685; A61B 17/00234
USPC ....... 606/264, 265, 266, 267, 270, 271, 272, 606/273, 276, 277, 278, 301, 305, 306, 606/308, 311, 312, 319, 324, 328
See application file for complete search history.

(56) References Cited

U.S. PATENT DOCUMENTS

| | | | |
|---|---|---|---|
| 8,337,532 B1* | 12/2012 | McLean | A61B 17/7085 606/279 |
| 9,456,859 B2 | 10/2016 | Peukert | |
| 10,786,285 B2* | 9/2020 | Stein | A61B 17/7043 |
| 2007/0239159 A1 | 10/2007 | Altarac et al. | |
| 2008/0177323 A1* | 7/2008 | Null | A61B 17/705 606/267 |
| 2010/0160981 A1 | 6/2010 | Butler et al. | |
| 2010/0256683 A1 | 10/2010 | Iott et al. | |
| 2013/0035727 A1 | 2/2013 | Datta | |
| 2014/0135839 A1 | 5/2014 | Frankel | |
| 2014/0336709 A1 | 11/2014 | Avidano et al. | |
| 2015/0032158 A1* | 1/2015 | Khajavi | A61B 50/30 606/246 |
| 2018/0228516 A1* | 8/2018 | Armstrong | A61B 17/7035 |
| 2018/0228518 A1 | 8/2018 | Carruth et al. | |
| 2018/0317972 A1 | 11/2018 | Abbasi | |

(Continued)

FOREIGN PATENT DOCUMENTS

| | | | | |
|---|---|---|---|---|
| EP | 3360495 | | 8/2018 | |
| EP | 3566665 A1 * | 11/2019 | | A61B 17/7001 |

*Primary Examiner* — Eduardo C Robert
*Assistant Examiner* — David C Comstock
(74) *Attorney, Agent, or Firm* — McHale & Slavin, P.A.

(57) ABSTRACT

A system, medical devices, and methods for use in surgical procedures, such as spinal surgeries. The system, medical devices, and methods are designed to provide a surgeon the ability to add a screw connector, or screw head such as a tulip, to pre-existing implanted bone, such as pedicle, facet, lateral mass, etc., screw system without having to remove the previously implanted screws and/or rods already existing in a patient.

20 Claims, 107 Drawing Sheets

(56) References Cited

U.S. PATENT DOCUMENTS

2020/0253644 A1* 8/2020 Biedermann ...... A61B 17/7037
2021/0085372 A1* 3/2021 Koutsoumbelis .. A61B 17/7034
2021/0177468 A1* 6/2021 Murray .............. A61B 17/7007
2023/0248397 A1* 8/2023 Lee ........................ A61B 17/86
606/270

* cited by examiner

MINIMALLY INVASIVE SURGERY ADD ON SCREW SYSTEM

CROSS REFERENCE TO RELATED APPLICATIONS

In accordance with 37 C.F.R. 1.76, a claim of priority is included in an Application Data Sheet filed concurrently herewith. Accordingly, the present invention claims priority to U.S. Provisional Patent Application No. 63/172,756 entitled "MINIMALLY INVASIVE SURGERY ADD ON SCREW SYSTEM" filed Apr. 9, 2021. The content of the above referenced application is incorporated herein by reference in its entirety.

FIELD OF THE INVENTION

The present invention relates to medical devices, systems, and methods; to medical devices, systems, and methods used in surgical procedures, such as minimally invasive surgical procedures; to medical devices, systems, and methods related to spinal surgeries; to medical devices, systems, and methods for adding additional surgical devices, such as a retractor or pedicle screw, or other bone screws, to existing surgical hardware, i.e., pedicle screws or rods already existing in a patient.

BACKGROUND OF THE INVENTION

Pedicle screw systems, such as those described in U.S. Pat. No. 9,456,859, U.S. Patent Application Publication No. 2014/0336709, and U.S. Patent Application Publication No. 2007/0239159 are typically utilized in spinal surgery to fixate the spine, including fusion surgeries from the occipital, cervical, thoracic, lumbar, sacral/coccyx spine, and pelvis. While these systems have been used for many years and are generally considered safe, such systems have their drawbacks and do not always result in a curing treatment for patients that have undergone such surgical procedures.

In the case of spinal fusion procedures, statistically, roughly three percent (3%) of patients who have undergone such a surgical procedure each year require additional surgery. Such patients typically require secondary surgical procedures to adjacent levels, this due to the additional stress added by the fusion levels. When there are existing bone screws in the spine and a level above and/or below have to be added, unfortunately, there's already a screw and rod in one of the vertebrae that will be part of the fusion during the secondary surgery performed. Utilizing minimally invasive techniques require that both vertebrae being fused have no screws in them so the surgeon can add screws attached to retractor blades, and then attach an external retractor device, if needed, to these retractor blades. This allows the surgeon to have exposure to the surgical level, as well as to perform distraction across the disc level, allowing the surgeon to insert the appropriate size cage in the disc space if needed. When a vertebra (vertebrae) already has a screw in it attached to a rod from a previous fusion, the surgeon is forced to either add a side connector to the rod, cut the rod and then remove the bone screw, or remove all the screws and rods from the previous fusion. Any one of such actions dramatically lengthens the time of the surgery, increases the infection risks, and increases the bleeding during surgical procedure. The present invention addresses these issues and provides a system, devices, and methods which can be used by the surgeon to avoid such problems.

Applicant's system, devices, and methods provide surgeons a mechanism to attach a retractor blade to an existing screw head. When completed with the surgical exposure fusion, surgeons are able to add a screw connector, or screw head such as a tulip, polyaxial, or monoaxial screw head, to the pre-existing implanted bone, such as pedicle, facet, lateral mass, etc., screw system without having to remove the previously implanted screws and/or rods. This dramatically decreases surgical time, as well as the risks and surgical exposure size for the patient. The patient should have less blood loss, less risk for infection, and a much quicker recovery with less postoperative pain.

SUMMARY OF THE INVENTION

The present invention relates to a system, medical devices, and methods for use in surgical procedures, such as spinal surgeries. The system, medical devices, and methods are designed to provide a user the ability to add a screw connector, or screw head such as a tulip, to the pre-existing implanted bone, such as pedicle, facet, lateral mass, etc., screw system without having to remove the previous implanted screws and/or rods already existing in a patient.

Accordingly, it is an objective of the invention to provide a system for use in surgical procedures.

It is a further objective of the invention to provide medical devices for use in surgical procedures.

It is a further objective of the invention to provide medical devices for use in surgical procedures in which a surgeon is required to add surgical devices, such as a screw connector, or screw head such as a tulip, to a pre-existing implanted bone screw system, such as pedicle, facet, lateral mass, etc., without having to remove the previous surgical devices, i.e. implanted screws and/or rods, already existing in a patient.

It is yet another objective of the invention to provide methods for use in surgical procedures.

It is a further objective of the invention to provide methods for use in surgical procedures in which a surgeon is required to add surgical devices, such as a screw connector, or screw head such as a tulip, to a pre-existing implanted bone screw system, such as pedicle, facet, lateral mass, etc., without having to remove the previous surgical devices, i.e. implanted screws and/or rods, already existing in a patient.

It is a still further objective of the invention to provide a system for use in spinal procedures.

It is a further objective of the invention to provide medical devices for use in spinal procedures.

It is yet another objective of the invention to provide methods for use in spinal procedures.

It is a still further objective of the invention to provide a system configured to allow a user the ability to add surgical devices, such as a screw connector, or screw head such as a tulip, to pre-existing implanted bone, such as pedicle, facet, lateral mass, etc., screw system without having to remove the previous surgical devices, i.e. implanted screws and/or rods, already existing in a patient.

It is a further objective of the invention to provide medical devices configured to allow a user the ability to add surgical devices, such as a screw connector, or screw head such as a tulip, to pre-existing implanted bone, such as pedicle, facet, lateral mass, etc., screw system without having to remove the previous surgical devices, i.e. implanted screws and/or rods, already existing in a patient.

It is yet another objective of the invention to provide methods which allow a user the ability to add surgical devices, such as a screw connector, or screw head such as a tulip, to pre-existing implanted bone, such as pedicle, facet, lateral mass, etc., screw system without having to remove the previous surgical devices, i.e. implanted screws and/or rods, already existing in a patient.

Other objectives and advantages of this invention will become apparent from the following description taken in conjunction with any accompanying drawings wherein are set forth, by way of illustration and example, certain embodiments of this invention. Any drawings contained herein constitute a part of this specification, include exemplary embodiments of the present invention, and illustrate various objects and features thereof.

BRIEF DESCRIPTION OF THE FIGURES

FIG. 37A is a perspective view of an illustrative embodiment of a tulip head connector;

FIG. 37B is an alternative perspective view of the tulip head connector shown in FIG. 37A;

FIG. 37C is a bottom perspective view of the tulip head connector shown in FIG. 37A;

FIG. 37D is an alternative bottom perspective view of the tulip head connector shown in FIG. 37A;

FIG. 37E is a top view of the tulip head connector shown in FIG. 37A;

FIG. 37F is a bottom view of the tulip head connector shown in FIG. 37A;

FIG. 37G is a front view of the tulip head connector shown in FIG. 37A;

FIG. 37H is a right side of the tulip head connector in FIG. 37A;

FIG. 37I is a left side of the tulip head connector shown in FIG. 37A;

FIG. 38A is a perspective view of an illustrative embodiment of a tulip head connector;

FIG. 38B is an alternative perspective view of the tulip head connector shown in FIG. 38A;

FIG. 38C is a bottom perspective view of the tulip head connector shown in FIG. 38A;

Figure 38A:
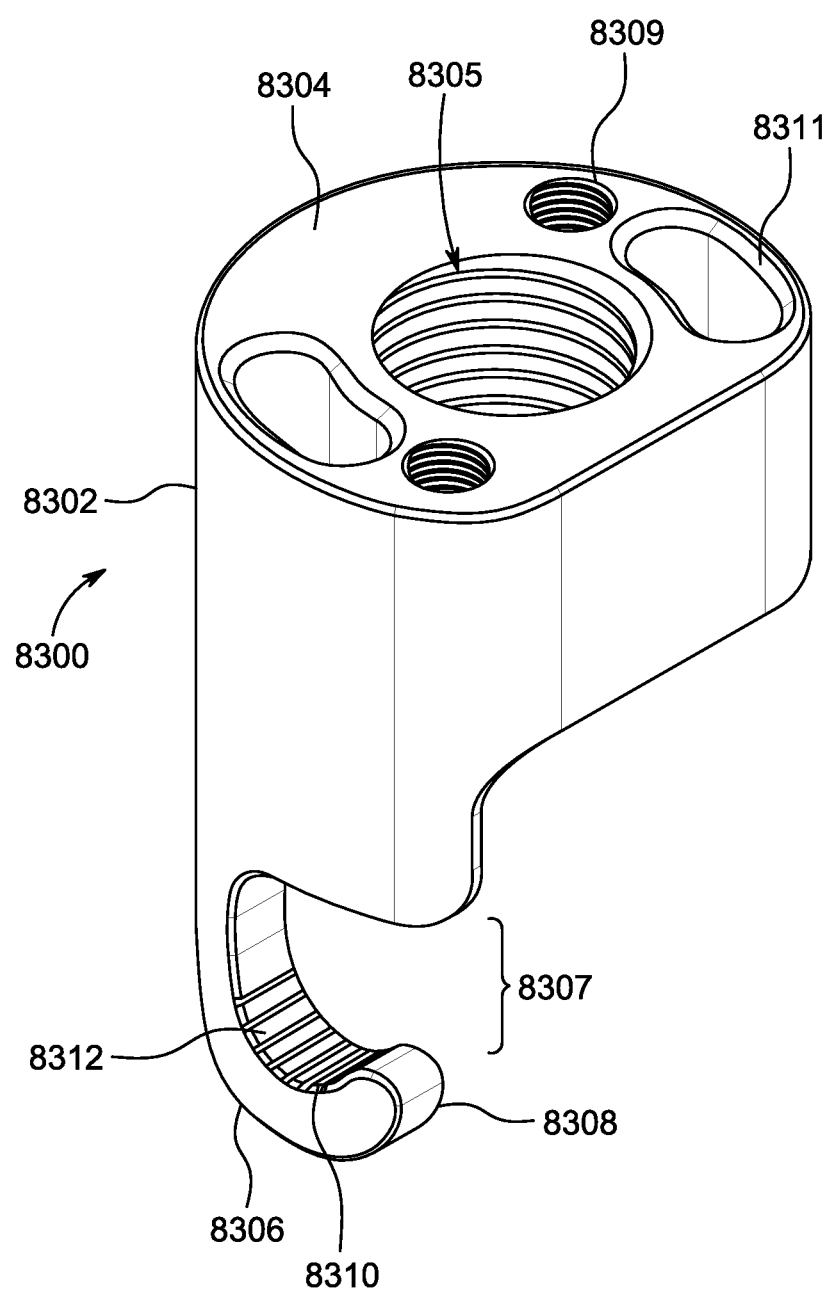
Figure 38B:
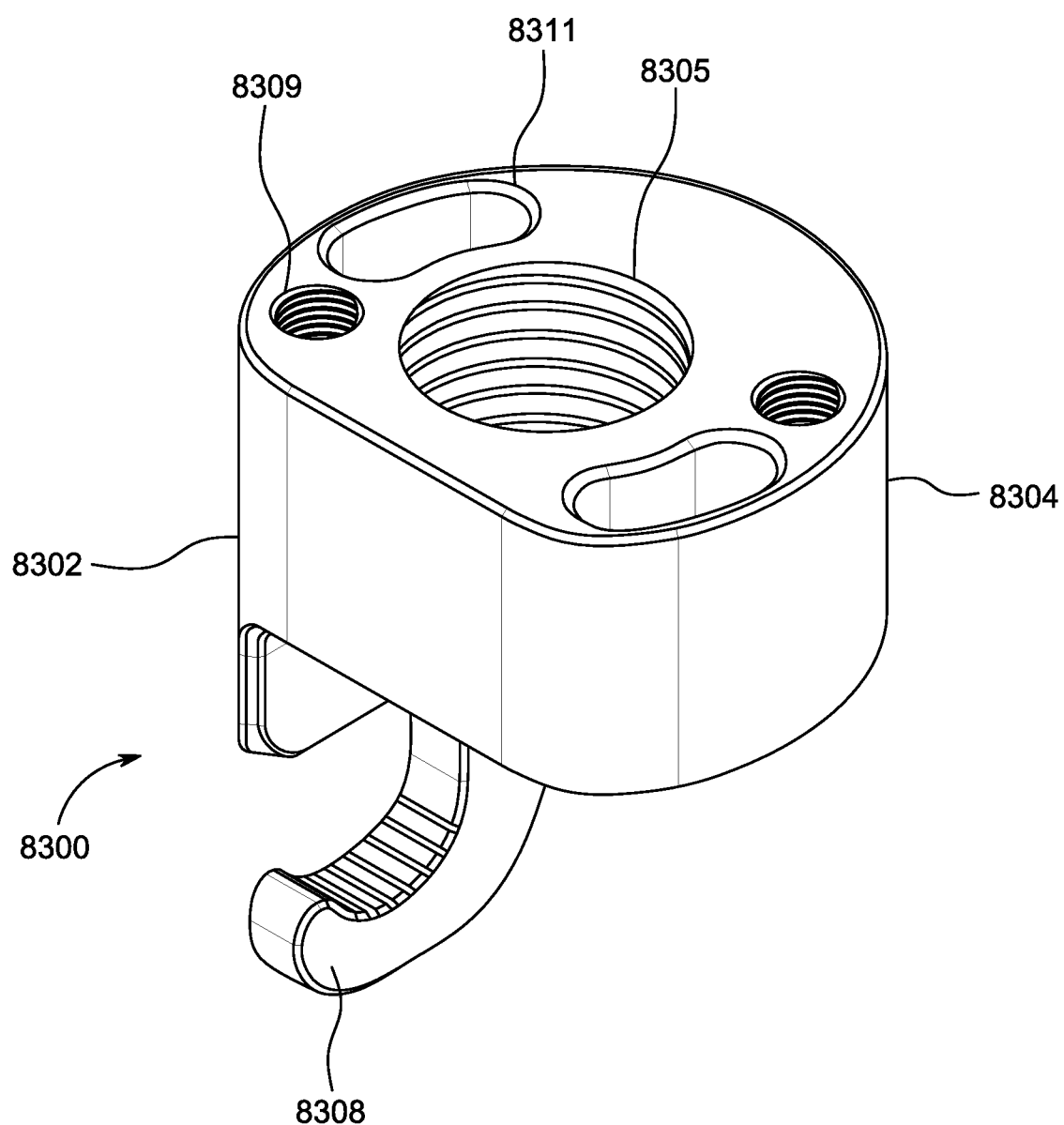
Figure 38C:
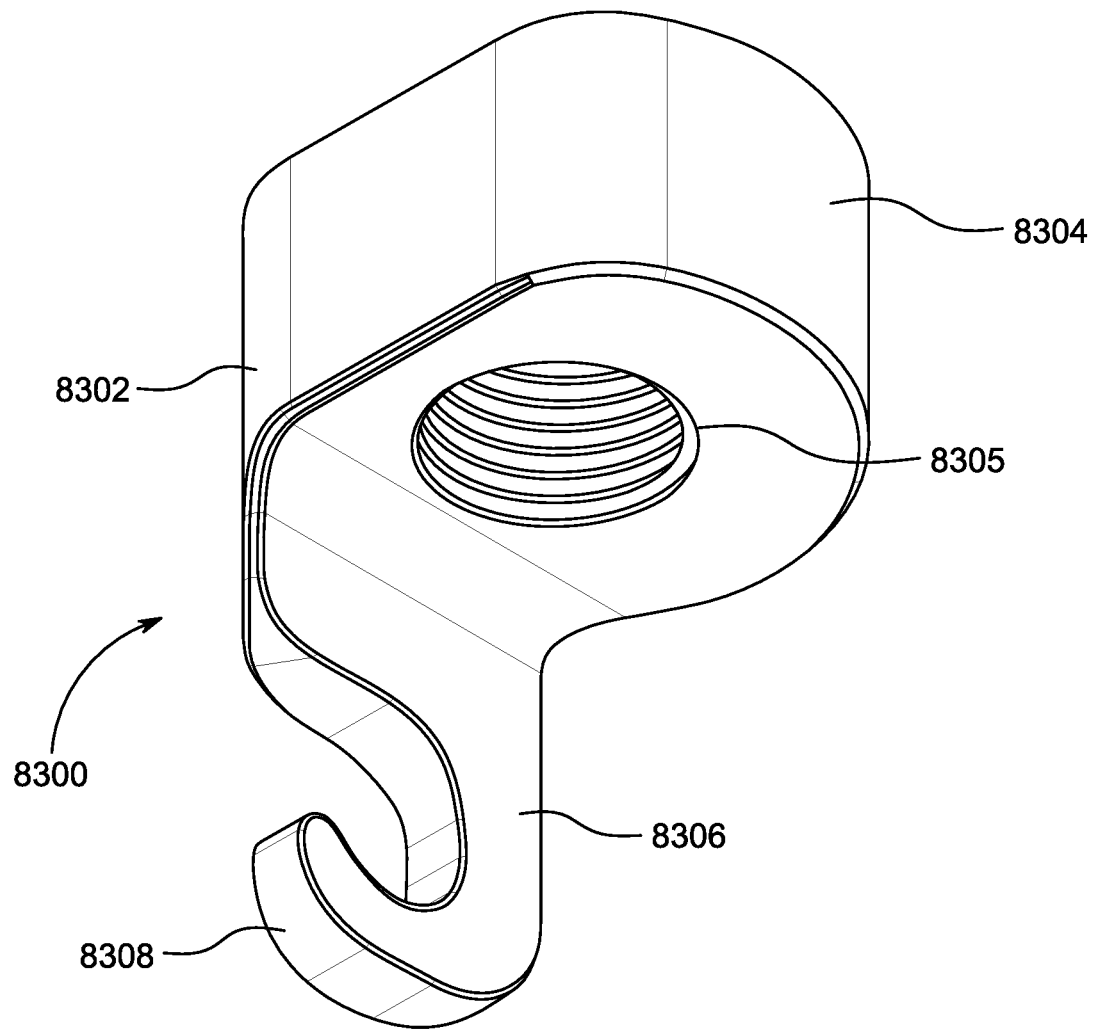
Figure 38D:
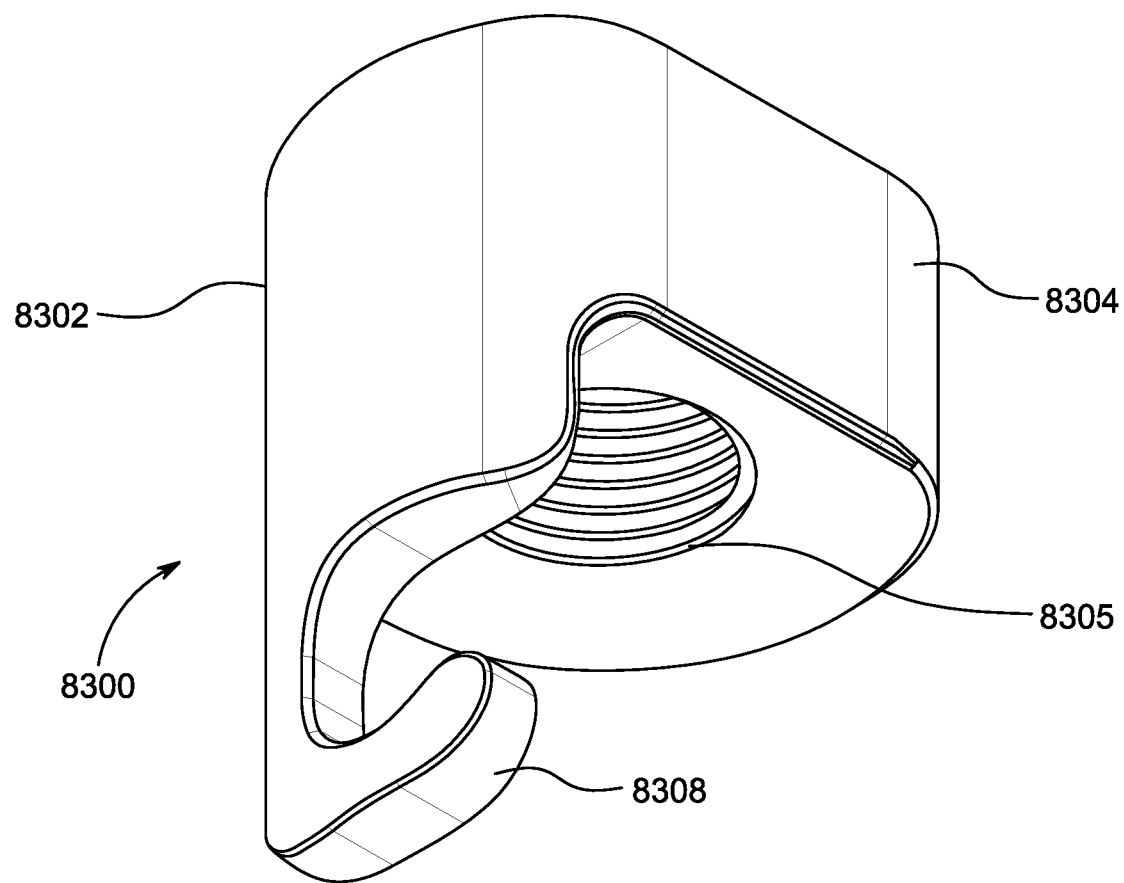
Figure 38E:
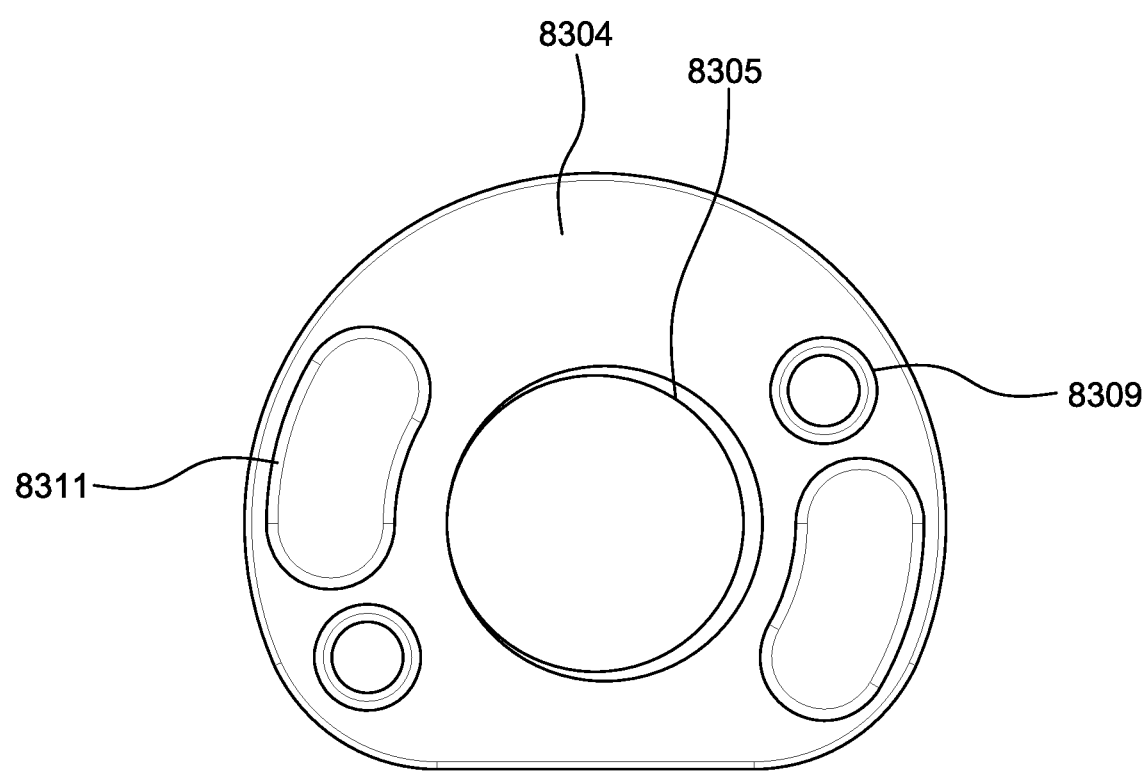
Figure 38F:
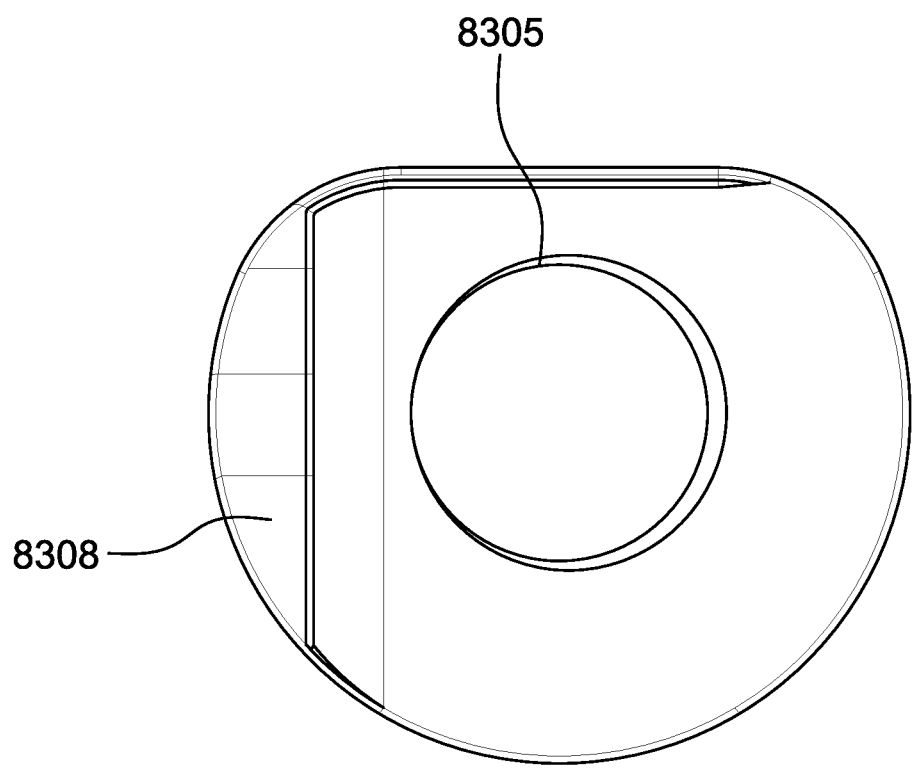
Figure 38G:
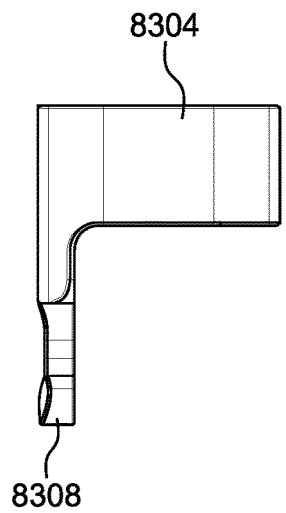
Figure 38H:
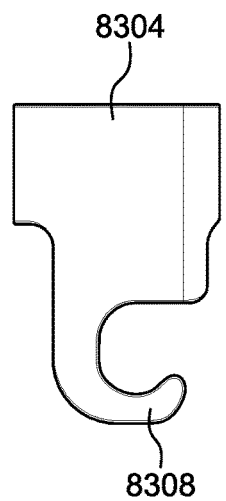

FIG. 38D is an alternative bottom perspective view of the tulip head connector shown in FIG. 38A;

FIG. 38E is a top view of the tulip head connector shown in FIG. 38A;

FIG. 38F is a bottom view of the tulip head connector shown in FIG. 38A;

FIG. 38G is a front view of the tulip head connector shown in FIG. 38A;

FIG. 38H is a right side of the tulip head connector in FIG. 38A; and

Figure 38I:
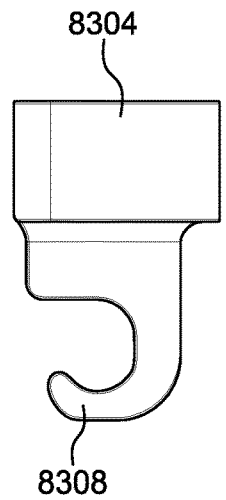

FIG. 38I is a left side of the tulip head connector shown in FIG. 38A.

DETAILED DESCRIPTION OF THE INVENTION

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

Referring to FIGS. 1-6, one or more components of an illustrative example of a surgical system for adding additional surgical devices to pre-existing surgical devices already in a patient, referred to generally as an add on screw system 100, is shown. While the add on screw system 100 is described for use with a pedicle (or bone, facet, lateral mass, etc.) screw related to spinal fusion procedures, the add on screw system 100 can be used in any orthopedic or spinal surgery in which a surgeon is required to add surgical devices, such as a screw connector, or screw head such as a tulip, to a pre-existing implanted bone screw system, such as pedicle, facet, lateral mass, etc., without having to remove the previous surgical devices, i.e. implanted screws and/or rods, already existing in a patient. In addition, while the add on screw system 100 may be described for use in minimally invasive surgical (MIS) procedures, the add on screw system 100, individually (i.e. individual components) or as an entire system, can be used in any type of surgical procedure.

The add on screw system 100 is illustrated herein attached to a primary pedicle screw system 12, representing pre-existing surgical devices already existing in a patient. While described for use with a pedicle screw, add on screw system 100 may be used with other bone screws, facet screws, lateral mass screws, etc. The primary pedicle screw system 12, also referred to as the pre-existing pedicle system 12, comprises a pedicle screw 14 having a threaded body 16 and pointed distal end or tip 18. A pedicle screw head or tulip 20 secures to the pedicle screw threaded body 16, and is configured to receive a surgical rod 22 when inserted, and held therein. The add on screw system 100 comprises a secondary tulip 102, referred to herein as the add on screw system tulip 102, an add on screw system head screw 104, and an add on screw system center threaded set screw 106.

The add on screw system tulip 102 is configured to receive and hold therein the screw system head screw 104, and includes a base, or seat, 108 separating side walls 110 and 112, and an interior 114. The interior 114 is defined by the space separating side walls 110 and 112. The inner surface 116 of side wall 110 and the inner surface 118 of side wall 112 may comprise internal threading 120 for engaging a set screw, thereby locking a secondary rod, or add on screw system rod, 122 in place between the side walls 110 and 112.

The add on screw system head screw 104 is configured to secure to the add on screw system center threaded set screw 106 at one end and to the add on screw system tulip 102 at another end. The add on screw system head screw 104 is shown having a main body 124, shown having a spherical shape, separating a first end 126 and a second end 128. The spherical shape provides for polyaxial movement or arrangement of the add on screw system tulip 102. The first end 126 has an upper surface 130 and an opening 132 exposing an interior 134. The opening 132 is sized and shaped to receive a head screw tightening device, such as a screw driver or hex wrench. The opening 132 is shown assuming a hexagonal shape, but such shape is illustrative only.

Integrally formed from or attached to, and extending from the screw system head screw main body 124 is an add on screw system center threaded set screw engagement member 136, illustrated herein as a generally cylindrically shaped threaded body. The screw system center threaded set screw engagement member threaded body 136 is sized and shaped to engage with, i.e. to secure into, a portion of the screw system center threaded set screw 106. In use, the add on screw system head screw 104 is placed within opening 138 of the add on screw system tulip 102 so a portion of the add on screw system head screw main body 124 rests on the add on screw system tulip seat 108. In this orientation, the screw system center threaded set screw engagement member threaded body 136 aligns with and engages with the add on screw system center threaded set screw 106.

The add on screw system center threaded set screw 106 is configured to secure the add on screw system tulip 102 to the pre-existing pedicle screw head or tulip 20. The add on screw system center threaded set screw 106 comprises a main body 140 having a thread on center 142. The add on screw system center threaded set screw main body 140 comprises an upper surface 145 having an opening 146, such as but not limited to a centrally positioned opening, exposing an interior 148. The opening 146 is sized and shaped to receive a set screw tightening device, such as a screw driver or hex wrench. The opening 146 is shown assuming a hexagonal shape, but such shape is illustrative only. The external surface 150 comprises threading 152 which is sized and shaped to engage with corresponding internal threading 154 of the pre-existing pedicle screw head or tulip 20. In use, the add on screw system center threaded set screw 106 is secured to the pre-existing pedicle screw head or tulip 20 by tightening the add on screw system center threaded set screw main body 140 via insertion of a set screw tightening device into the opening 146. Once secured, the add on screw system center threaded set screw engagement member threaded body 136 may be inserted into the interior 148 of the add on screw system center threaded set screw main body 140, engaging with the thread on center 142.

FIGS. 1-6 illustrate the add on screw system 100 utilizing a tulip within a tulip mechanism for securing a new tulip to an existing tulip. FIGS. 7-12 illustrate the add on screw system 100 which utilizes a side to side tulip connecting mechanism. In one embodiment of the side to side tulip connecting mechanism, a two-component device, referred to herein as a two-piece side tulip connector 156 is shown. The two-piece side tulip connector 156 comprises a first component 158 configured to engage with and/or secure to a preexisting portion of a pedicle screw, preferably at or along the tulip portion, and a second component 160, configured to engage with at least a portion of the two-piece side tulip connector first component 156 and a secondary tulip. The two-piece side tulip connector first component 158 comprises a main body 162, an upper portion 164, and a lower portion 166. The two-piece side tulip connector first component main body upper portion 164 is separated from the two-piece side tulip connector first component main body lower portion 166 by a space 170, forming a receiving channel 171.

The receiving channel 171 is sized and shaped to receive and store therein the pre-existing tulip head 20 and/or rod 22. The upper surface 172 of the two-piece side tulip connector first component main body upper portion 164 may comprise one or more openings 174 sized and shaped to receive different structures, such as a set screw 175, for securing the two-piece side tulip connector 156 to the pre-existing tulip head 20, for securing the two-piece side tulip connector second component 160 to the two-piece side tulip connector first component 158, or for securing to a retractor blade thereto.

The two-piece side tulip connector first component lower portion 166 comprises a preexisting pedicle screw engagement member 176. The preexisting pedicle screw engagement member 176 is illustrated having two arms or finger-like projections 178 and 180 extending away from the two-piece side tulip connector first component 158 main body 162. The arms or finger-like projections 178 and 180 are separated by a space 182 sufficient in size to accommodate at least a portion of a preexisting pedicle screw threaded body 16 to rest or be placed therein. As shown, the arms or finger-like projections 178 and 180 are placed at or near where the preexisting pedicle screw threaded body 16 exits from the preexisting tulip 20, and resting under the preexisting tulip 20.

The two-piece side tulip connector second component 160 comprises a first end 184, a second end 186, and a main body 188 separating the first end 184 and the second end 186. The two-piece side tulip connector second component first end 184 is designed to engage with at least a portion of the two-piece side tulip connector 156 and may contain an upper platform section 190 which may extend away from the main body 188, forming a curved or angled section. The upper platform section 190 may have an opening 192 which may be placed over opening 174. Insertion of a screw therein provides a mechanism to lock the second component 160 to the first component 158. The second end 186 may contain a secondary tulip engaging member 194, illustrated herein as a lower platform 195 with a surface 196 extending away from the main body 188. An opening 198 rests within the surface 196 and is sized and shaped to receive a tulip securing screw 200. The lower platform 194 positions the secondary tulip 202 next to and in a side by side relationship. In this position, a secondary rod may be attached to the preexisting tulip 20.

Figure 1:
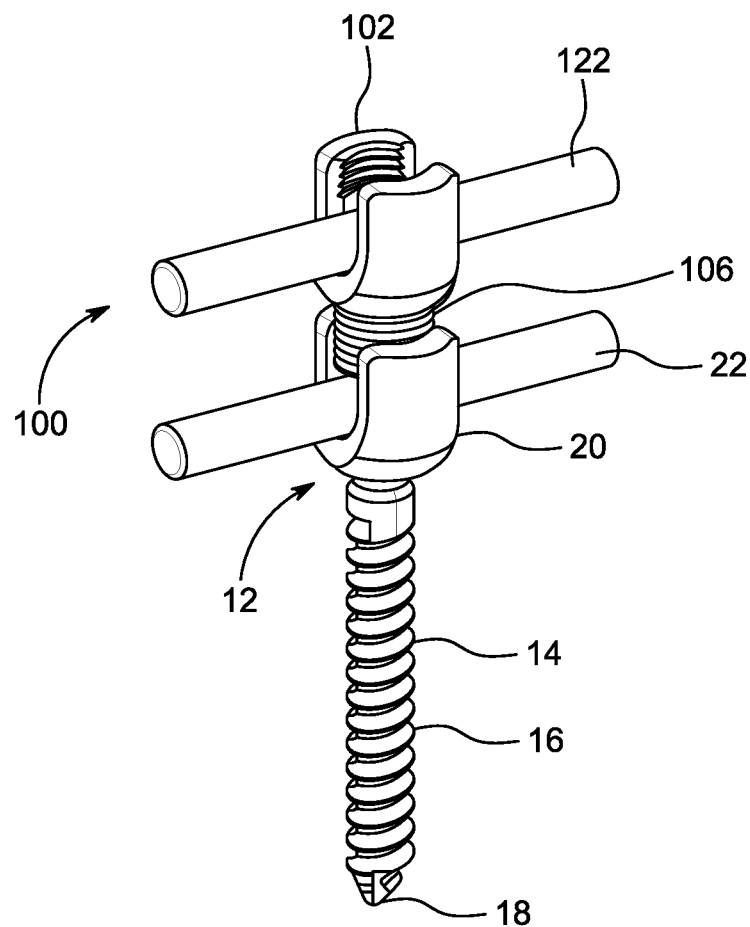
FIG. 1 illustrates a perspective view of an embodiment of an add-on screw system, illustrating a tulip within a tulip mechanism for securing an add on tulip to a preexisting tulip previously implanted into a patient.
Figure 2:
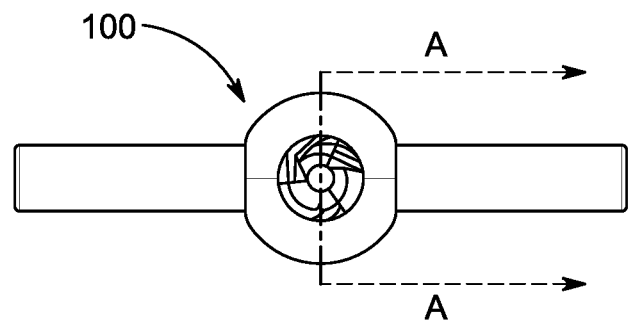
FIG. 2 is a top view of the add-on screw system illustrated in FIG. 1.
Figure 3:
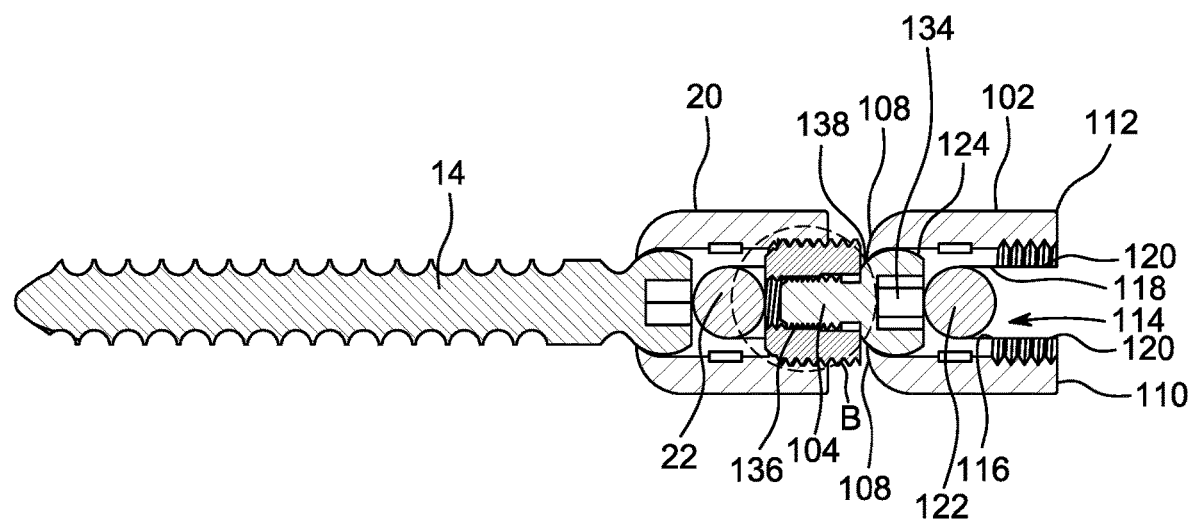
FIG. 3 is a cross section of the add-on screw system illustrated in FIG. 1, taken along lines A-A in FIG. 2.
Figure 4:
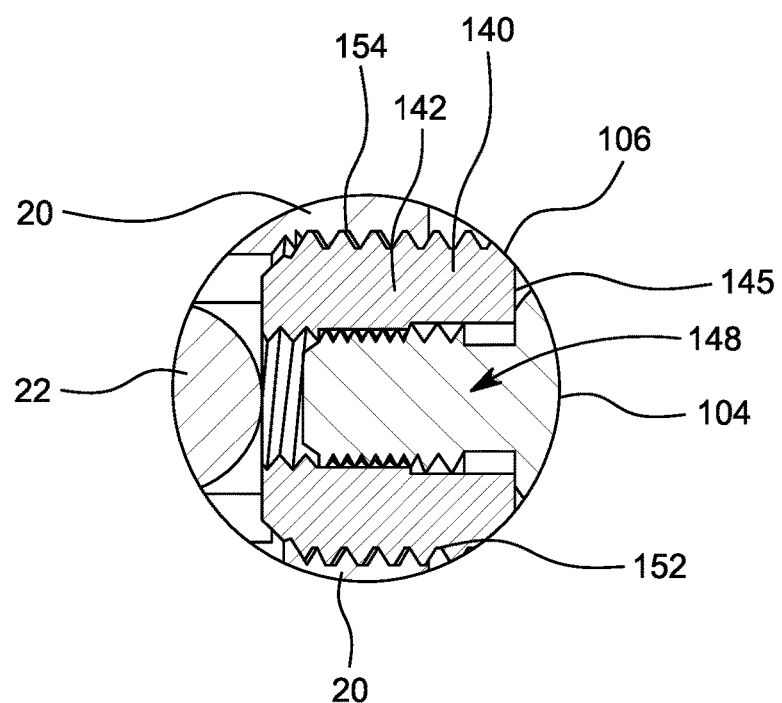
FIG. 4 is an enlarged view of Section B shown in FIG. 3.
Figure 5:
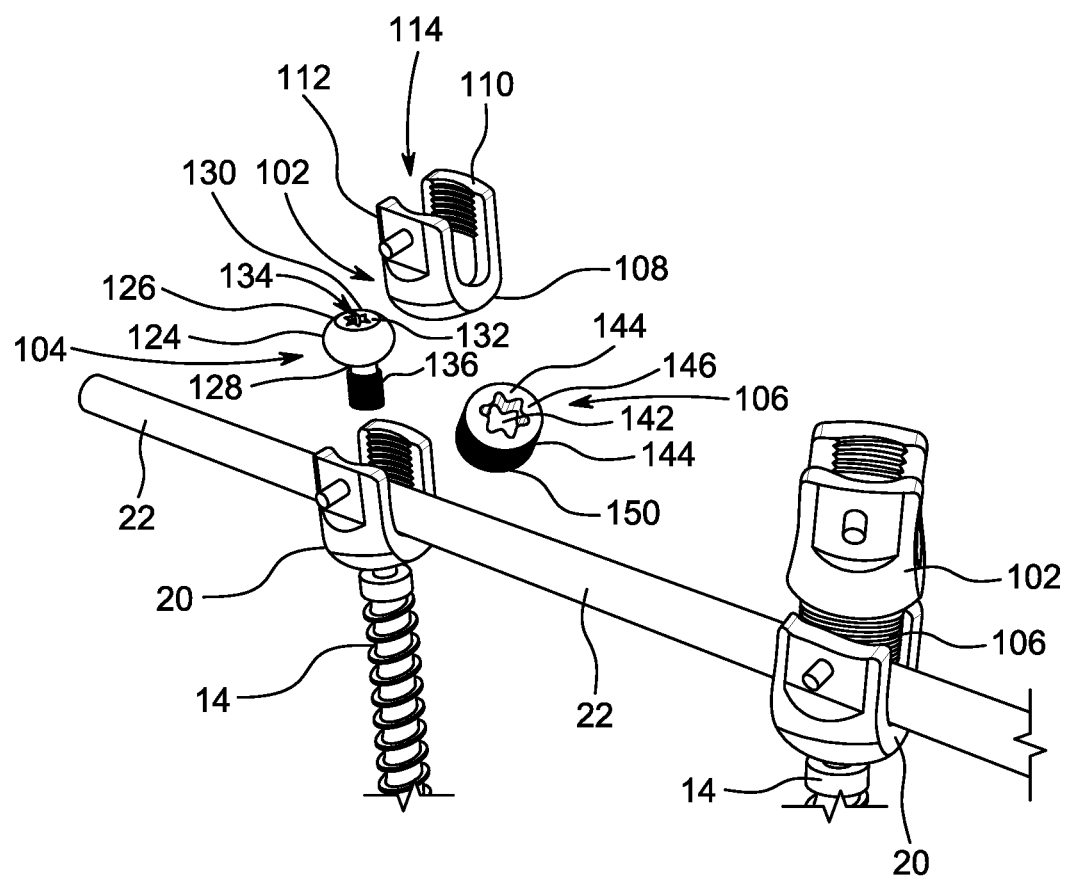
FIG. 5 is an exploded view of the add-on screw system illustrated in FIG. 1.
Figure 6:
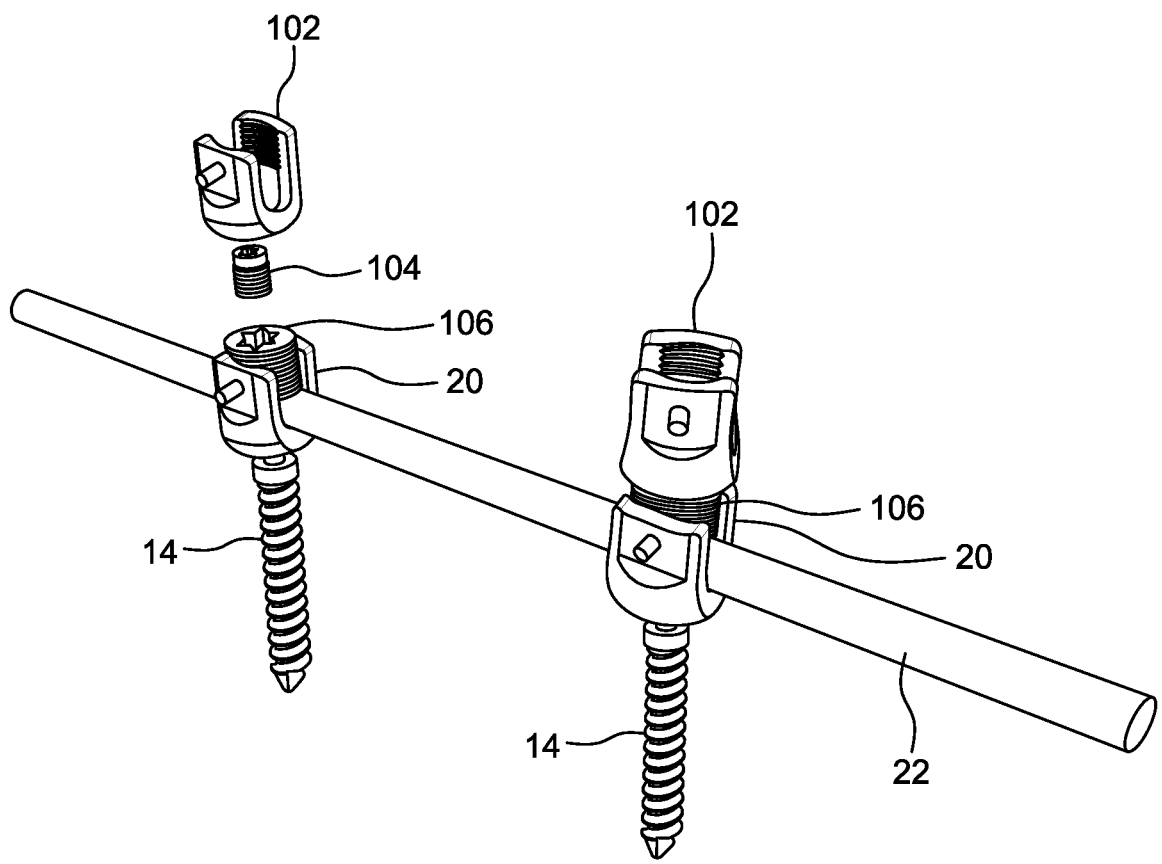
FIG. 6 illustrate add-on screw system units secured to a surgical rod.
Figure 7:
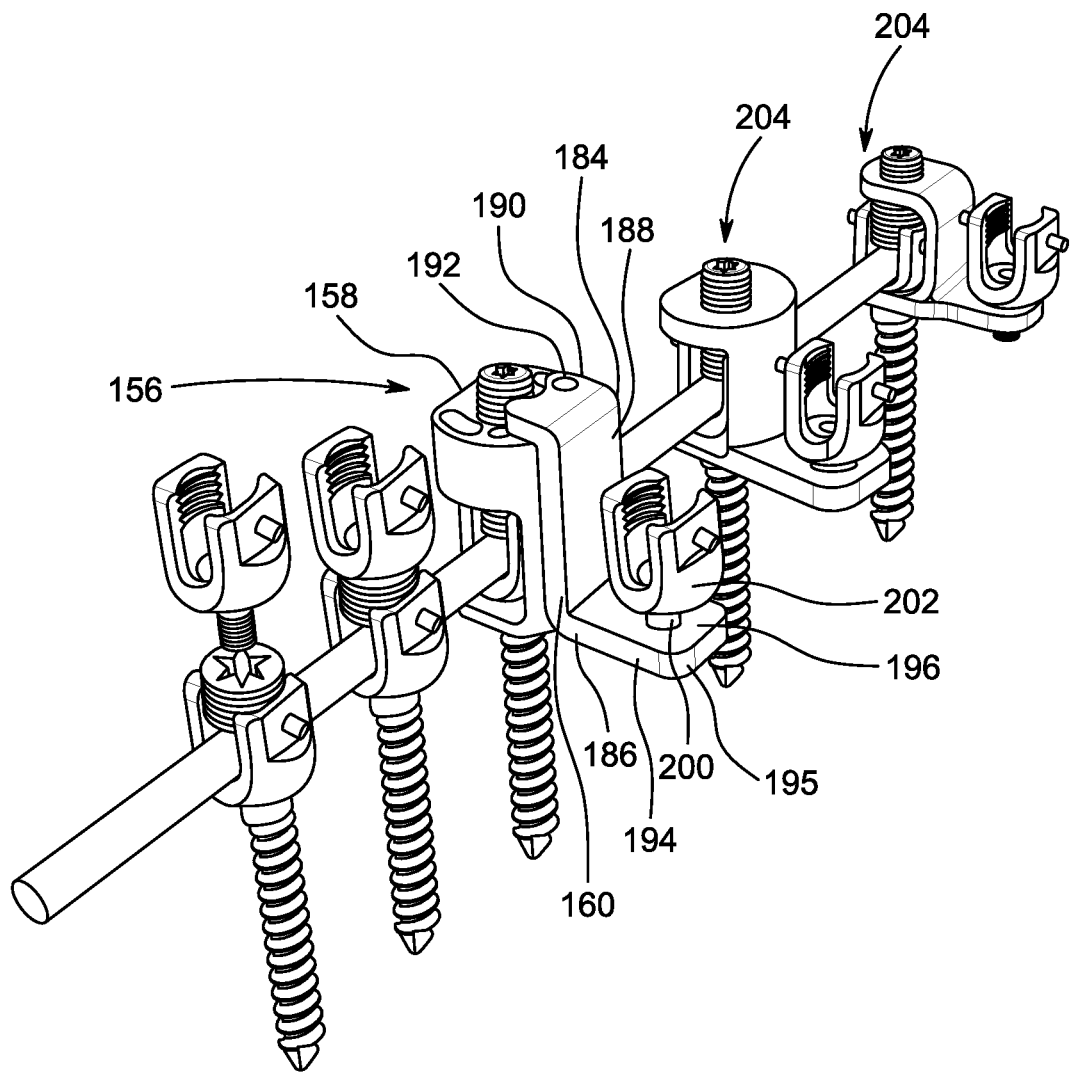
FIG. 7 illustrates a perspective view of an embodiment of an add-on screw system, utilizing a tulip to side tulip mechanism for securing the add on tulip to a preexisting tulip previously implanted into a patient.
Figure 8:
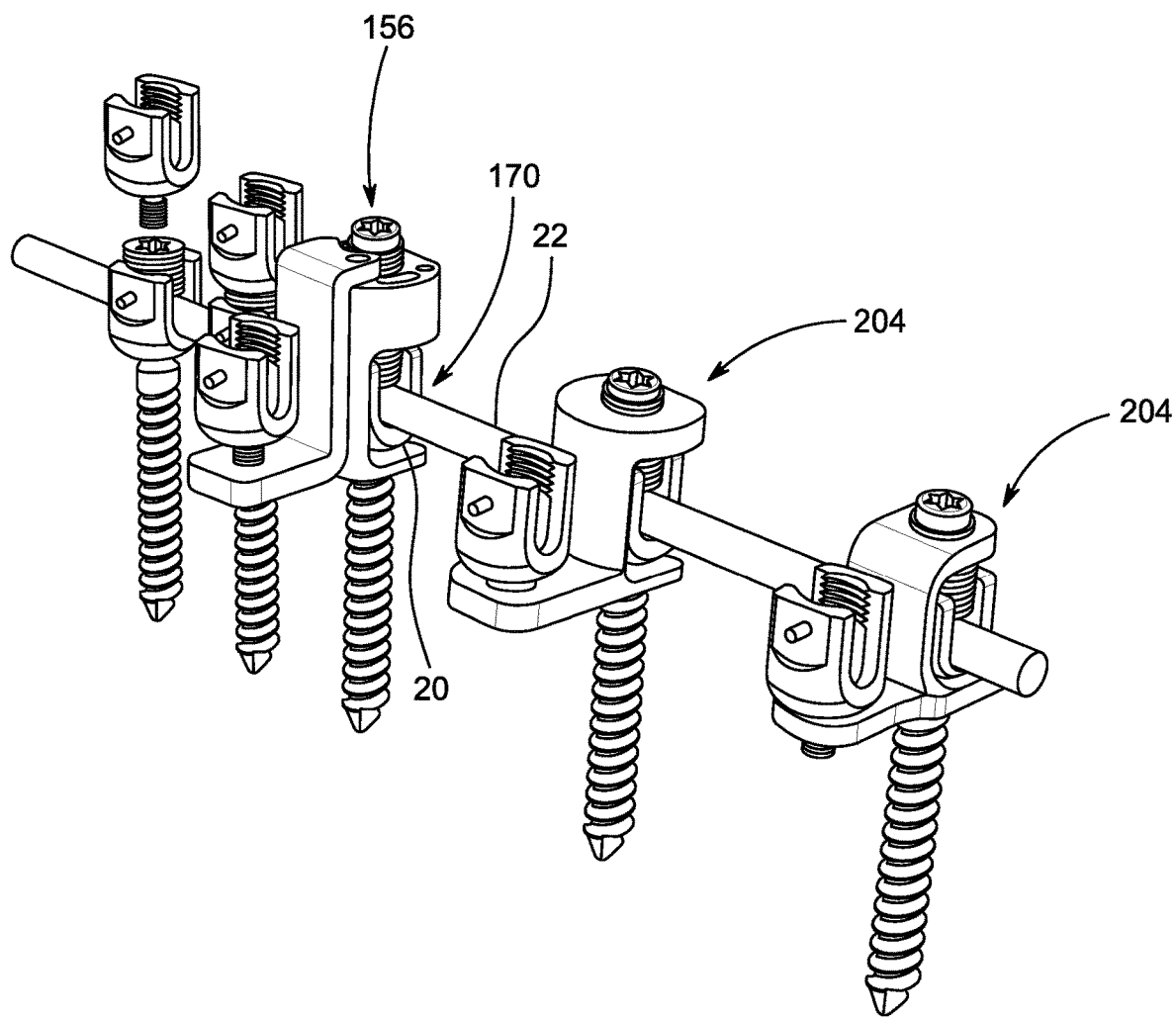
FIG. 8 is an alternative view of the add-on screw system illustrated in FIG. 7.
Figure 9:
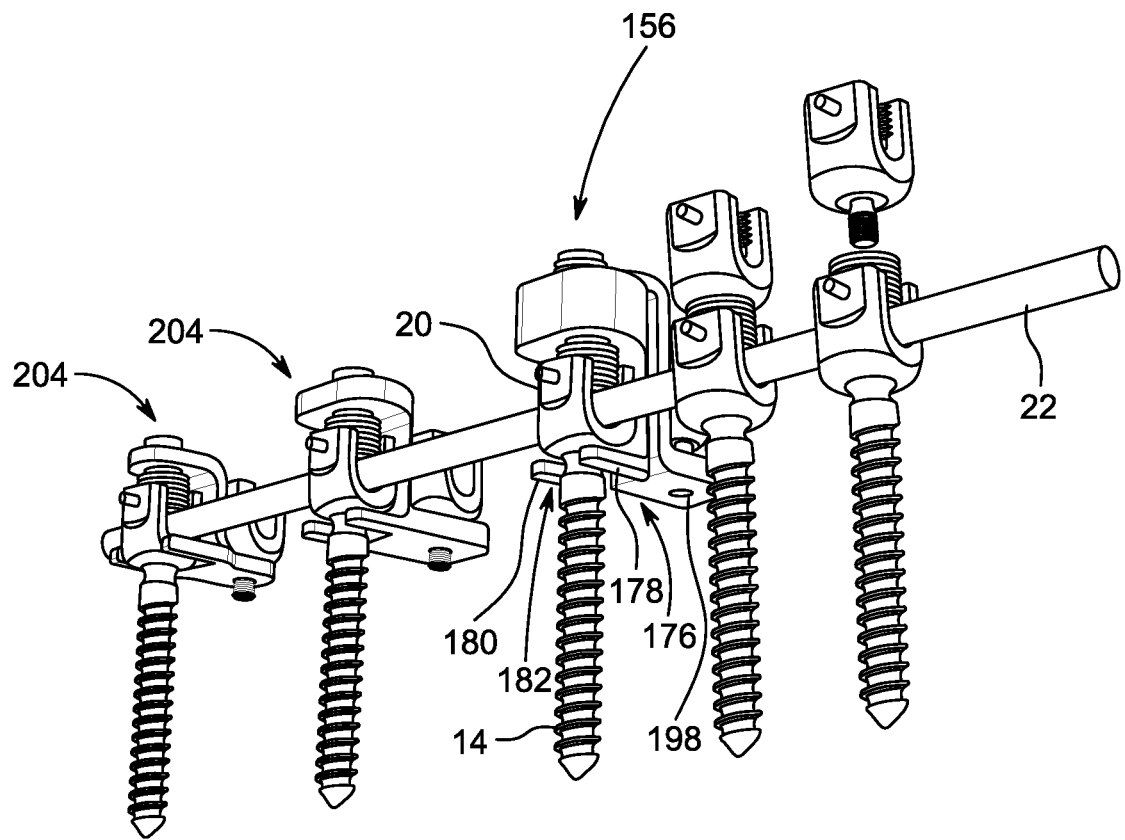
FIG. 9 is an alternative view of the add-on screw system illustrated in FIG. 7.
Figure 10:
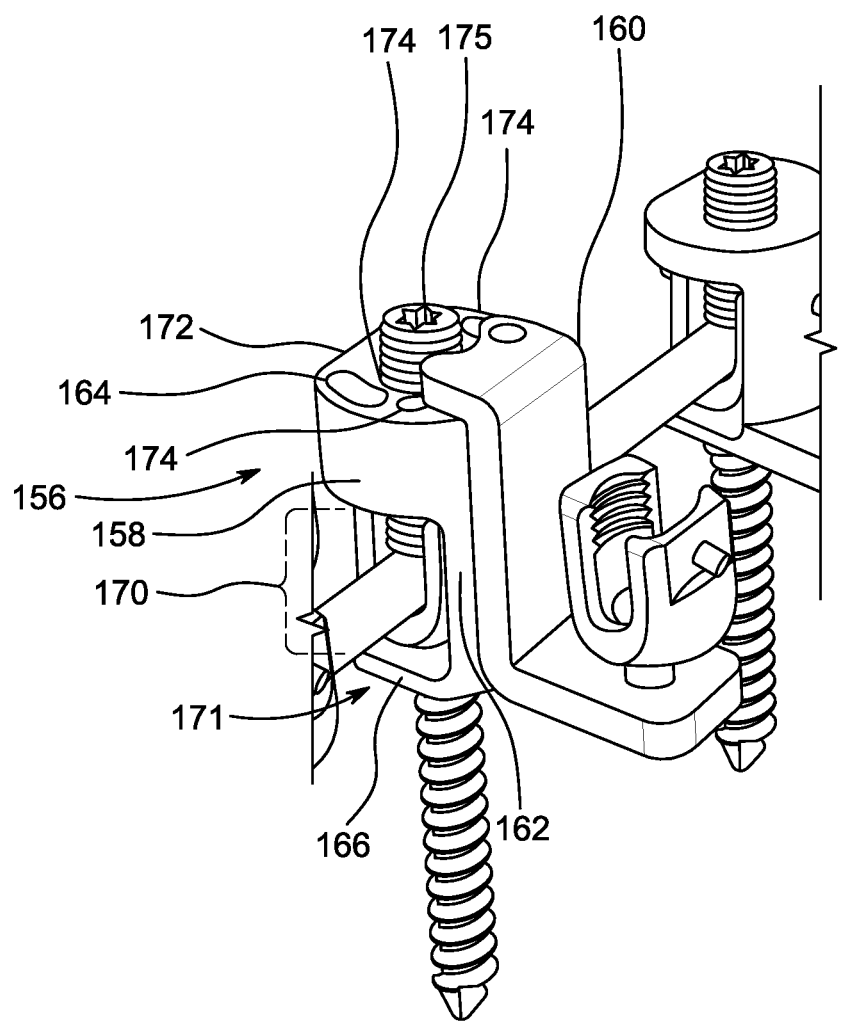
FIG. 10 is a perspective view of an embodiment of a two-component tulip to side tulip device.
Figure 11A:
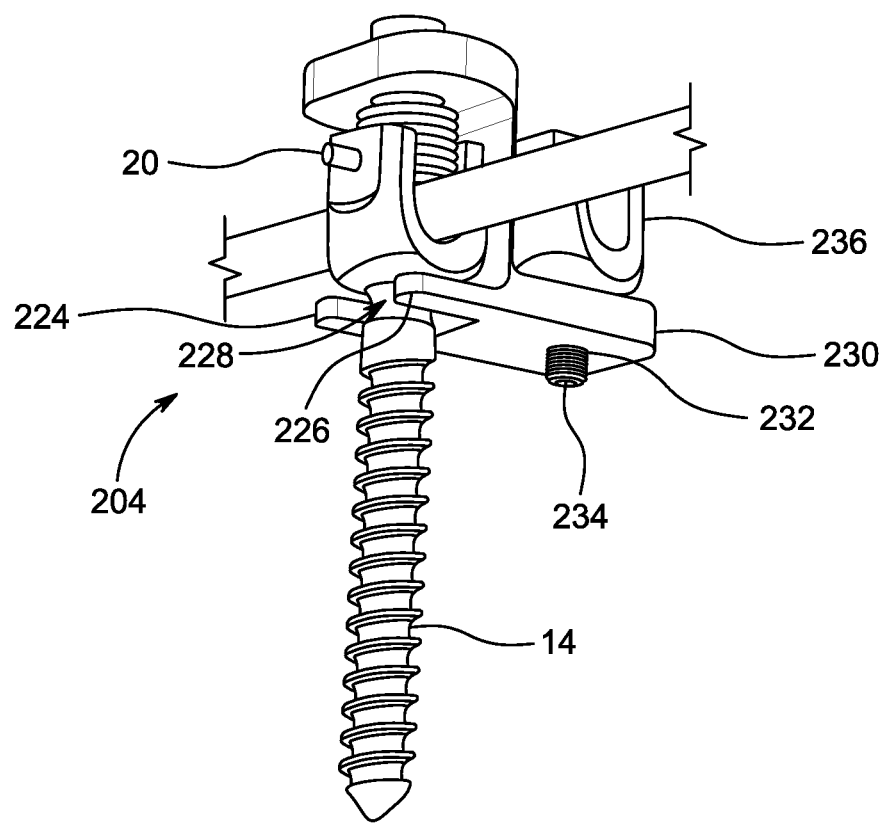
FIG. 11A is a perspective view of an embodiment of a one-component tulip to side tulip device.
Figure 11B:
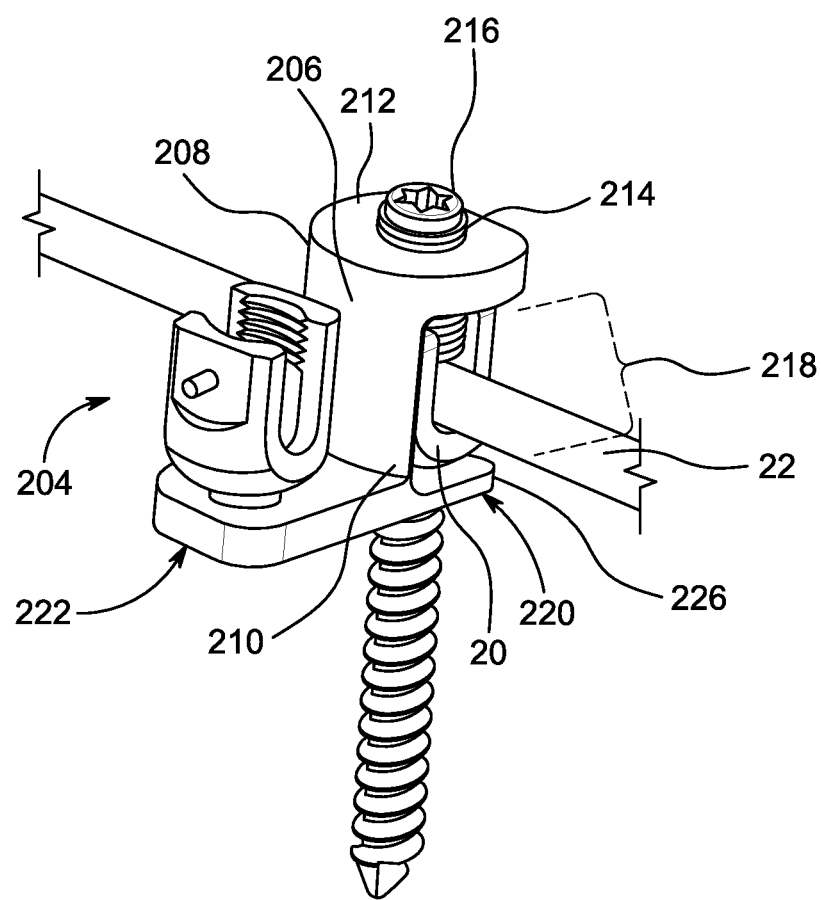
FIG. 11B is an alternative perspective view of the one-component tulip to side tulip device.

Referring to FIGS. 11A and 11B, an embodiment of the side to side tulip connecting mechanism illustrated as a one-component device, referred to herein as a one-piece side tulip connector 204, is shown. The one-piece side tulip connector 204 is configured to engage with and/or secure to a preexisting portion of a pedicle screw and with a secondary tulip. Accordingly, the one-piece side tulip connector 204 provides for a tulip head attachment with side mount add-on tulip head. The one-piece side tulip connector 204 may be adapted to fit on an existing tulip head, fixed with a top set screw. The one-piece side tulip connector 204 includes a place on the side to mount an add-on tulip head or other accessories. The one-piece side tulip connector 204 comprises a main body 206 having an upper end 208 and a bottom end 210. The upper end 208 comprises a surface 212 which extends away from the main body 206. The surface 212 may comprise an opening 214 sized and shaped to receive set screw 216. A portion of the one-piece side tulip connector main body upper end 208 is separated from the bottom end 210 via space 218, thus forming a preexisting tulip or rod receiving channel sized and shaped to receive and hold therein a preexisting tulip 20 or rod 22.

The one-piece side tulip connector bottom end 210 comprises a preexisting pedicle screw engagement member 220 and a secondary tulip engaging member 222. The preexisting pedicle screw engagement member 220 is illustrated having two arms or finger-like projections 224 and 226 extending away from the one-piece side tulip connector 204 main body 206. The arms or finger-like projections 224 and 226 are separated by a space 228 of sufficient size to accommodate at least a portion of a preexisting pedicle screw threaded body 16 to rest or be placed therein. As shown, the arms or finger-like projections 224 and 226 are placed at or near where the preexisting pedicle screw threaded body 16 exits from the preexisting tulip 20, and resting under the preexisting tulip 20.

The secondary tulip engaging member 222 is illustrated herein as an extended platform or surface 230 extending away from the one-piece side tulip connector 204 main body 206 and in the opposite direction of the preexisting pedicle screw engagement member 220. An opening 232 rests within the extended platform or surface 230 and is sized and shaped to receive a tulip securing screw 234. The extended platform or surface 230 positions the secondary tulip 236 next to and in a side by side relationship with the preexisting tulip 20. In this position, a secondary rod may be attached to the preexisting tulip 20. While the secondary tulip 236 may be attached to the preexisting pedicle screw engagement member 220 via threading and tulip securing screw 234, alternative embodiments may include the secondary tulip 236 being pre-attached (pre-assembled) or secured via other means, such as welding.

Referring to FIGS. 12A-12F, alternative embodiments of the add on screw system 100 utilizing a tulip within a tulip mechanism for securing a new tulip to an existing tulip are shown. In this embodiment, the add on screw system 100 includes a tulip to tulip connector, referred to as a tulip to tulip head attachment connector 238 or tulip to tulip head attachment connector 240. The tulip to tulip head attachment connector 238 is designed to engage with or secure to the bottom portion of the pre-existing tulip 20 which is secured to the preexisting threaded body 16 of the preexisting pedicle screw 14. The tulip to tulip head attachment connector 238 comprises an upper portion 242, a lower portion 244, and an intermediate portion 246 separating the upper portion 242 and the lower portion 244. The upper portion 242 is configured to engage with an add-on tulip head 248. The lower portion 244 is configured to engage with the pre-existing tulip 20.

Figure 12A:
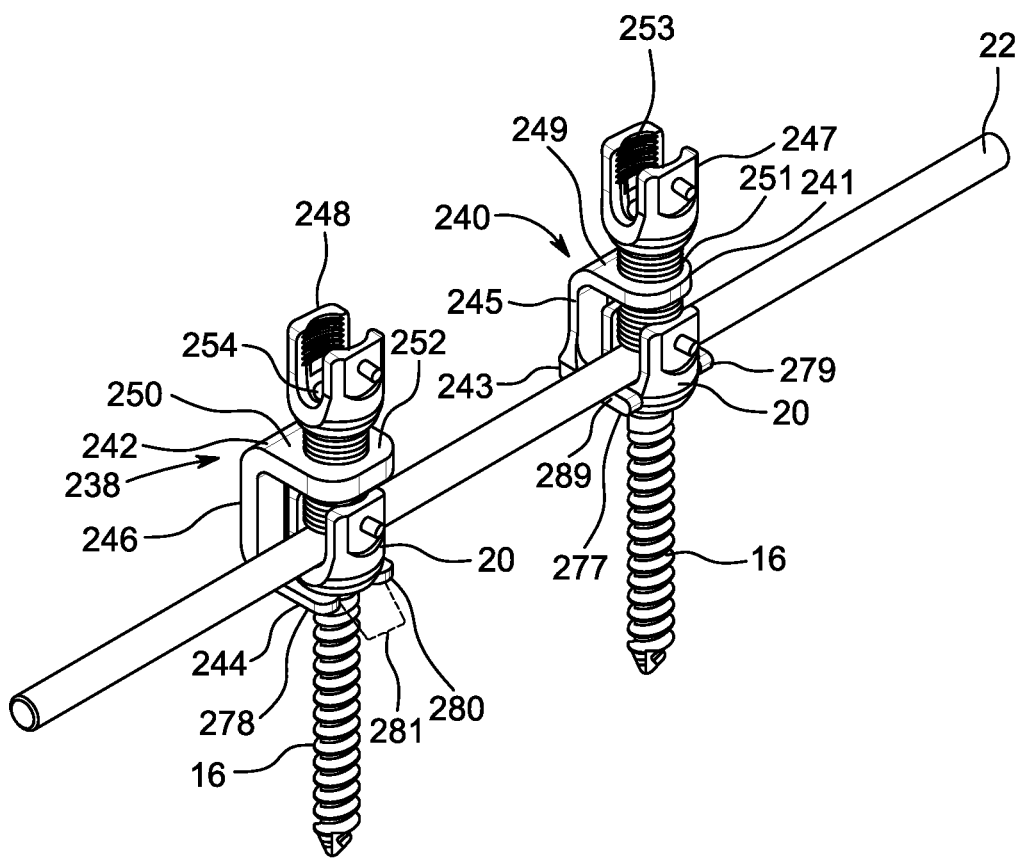
FIG. 12A is a perspective view of an alternative embodiment of the add on screw system utilizing a tulip within a tulip mechanism for securing a new tulip to an existing tulip.
Figure 12B:
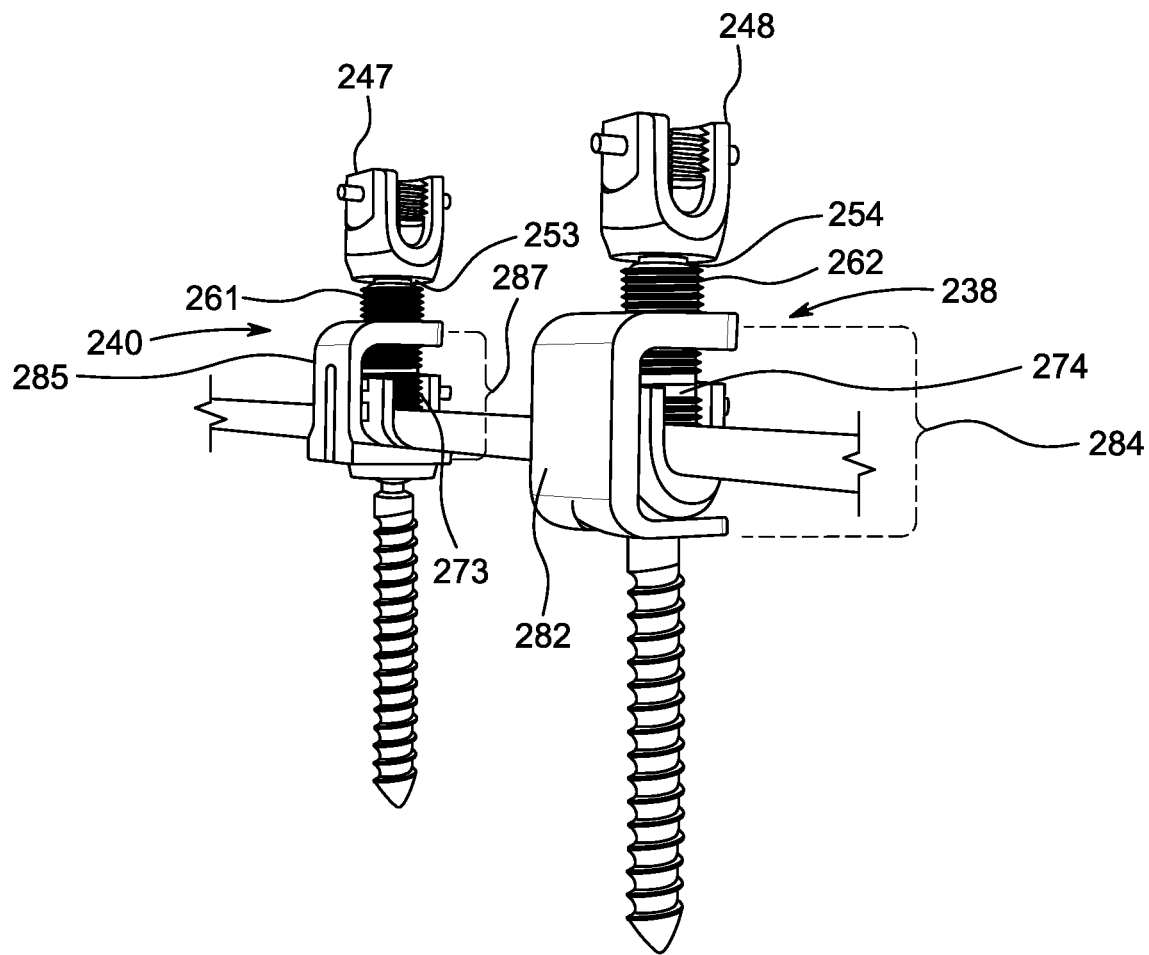
FIG. 12B is an alternative perspective view of the add on screw system illustrated in FIG. 12A.
Figure 12C:
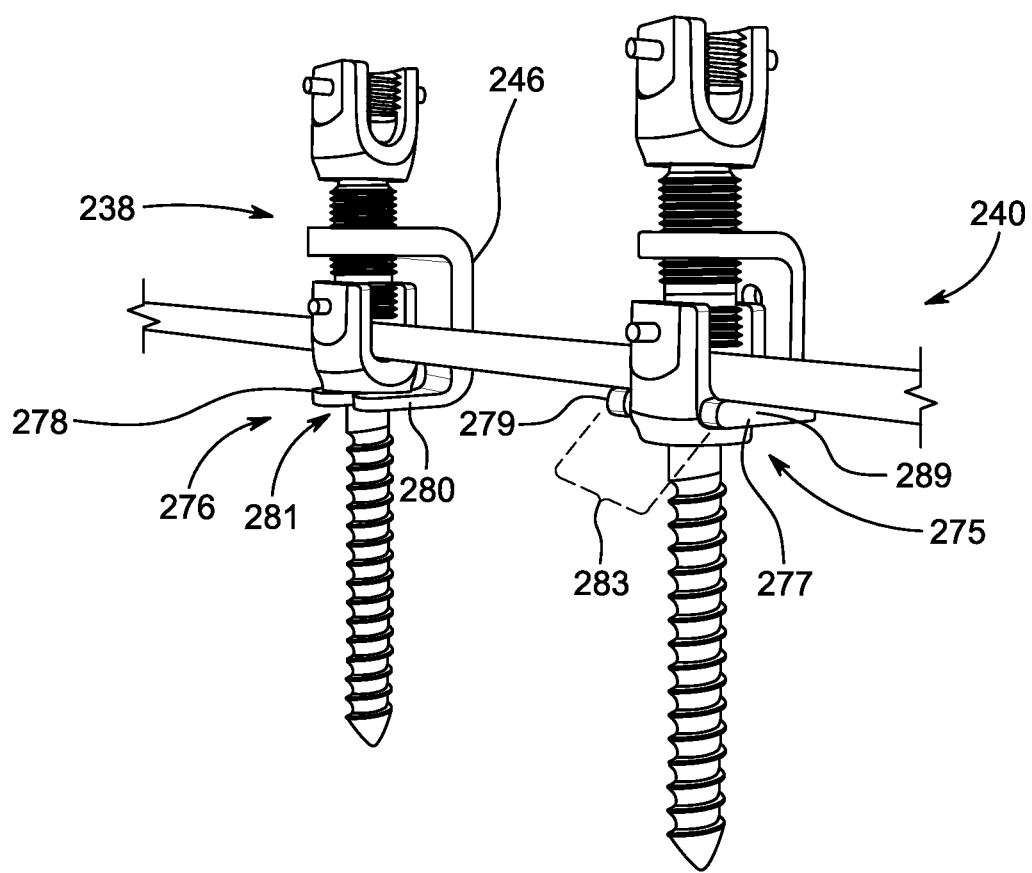
FIG. 12C is an alternative perspective view of the add on screw system illustrated in FIG. 12A.
Figure 12D:
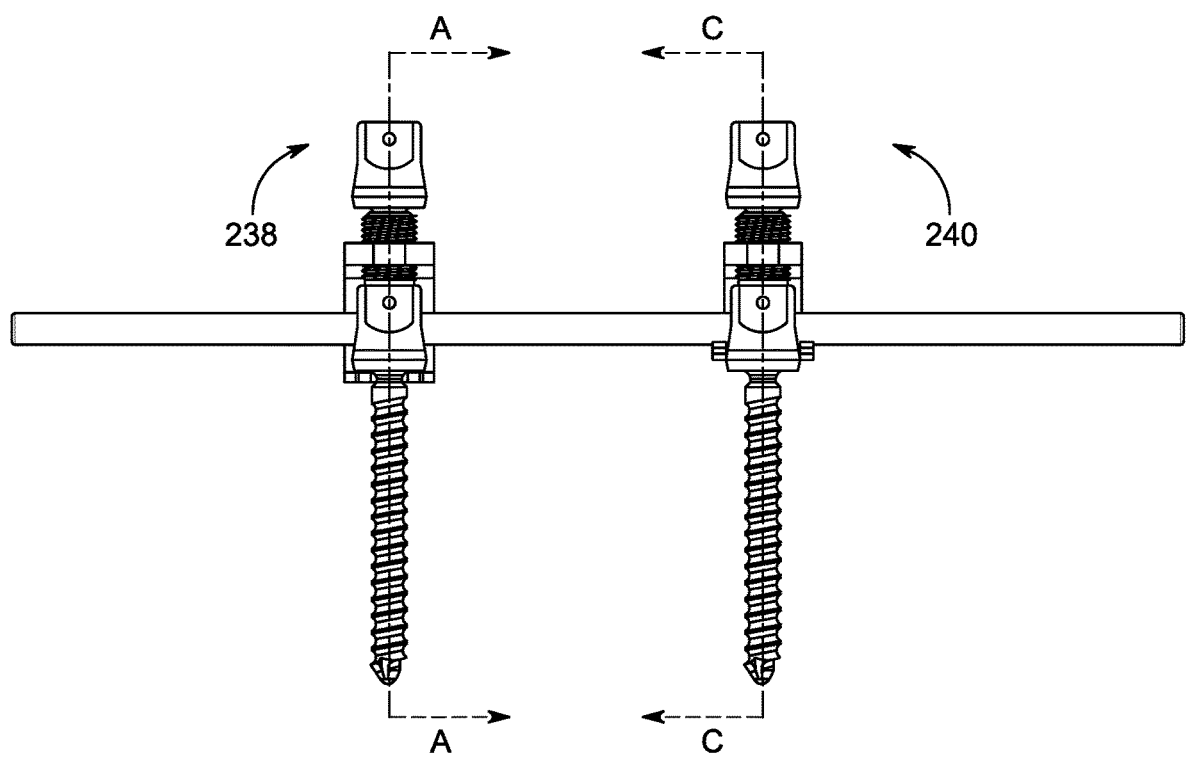
FIG. 12D is a plane view of the add on screw system illustrated in FIG. 12A.
Figure 12E:
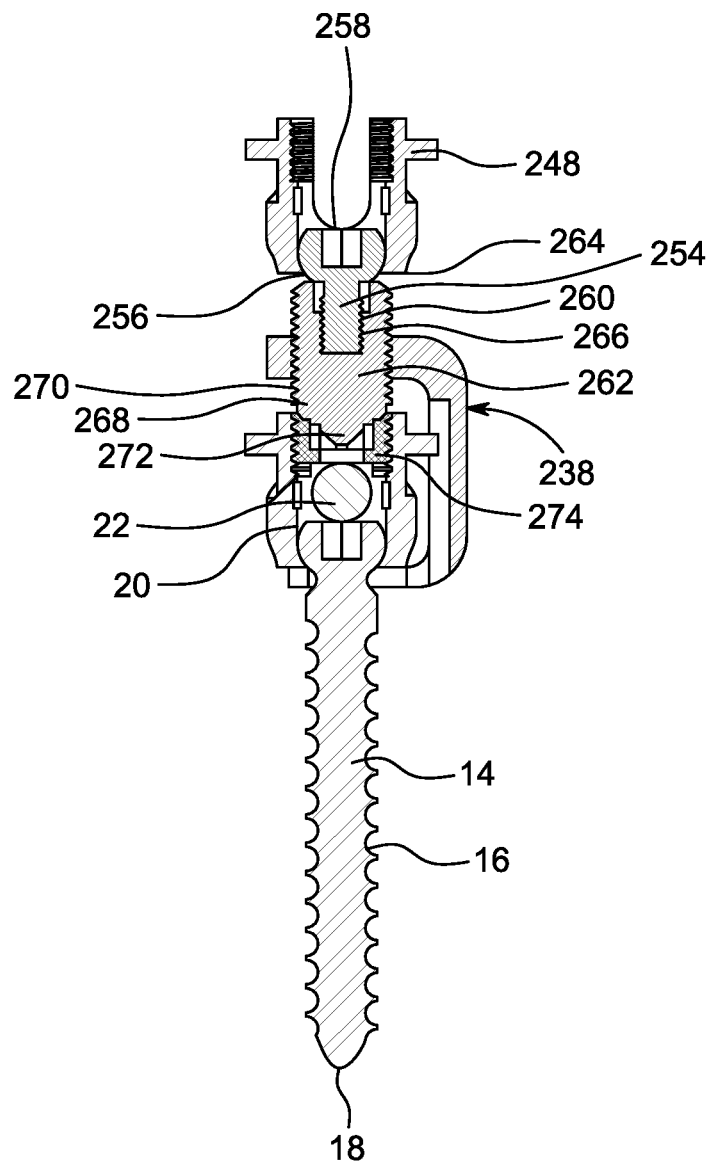
FIG. 12E is a cross section view of the add on screw system illustrated in FIG. 12A, taken along lines A-A in FIG. 12D.

The upper portion 242 comprises a surface 250 having an opening 252 sized and shaped to receive and hold therein an add-on spherical screw 254. The add-on spherical screw 254 is designed to fix the add-on tulip head 248 in place. As seen in FIGS. 12E, the add-on spherical screw 254 includes an upper spherical body 256, sized and shaped to fit within a seat 258 of the add-on tulip head 248, and a threaded body 260. While illustrated as having a spherical body 256 to provide the add-on tulip head 248 polyaxial movement, the add-on spherical screw 254 may include an upper body having a different shape. The add-on spherical screw threaded body 260 is designed to secure to an attachment fixing set screw 262; the attachment fixing set screw 262 including an opening 264 with corresponding inner threading 266. The attachment fixing set screw 262 may include a body 268 having an outer threading 270, and terminating in a conical shaped end 272, thus allowing the attachment fixing set screw 262 to tighten a pre-existing tulip head set screw 274 secured within the preexisting tulip head 20.

The tulip to tulip head attachment connector lower portion 244 comprises a pre-existing tulip head engagement member 276. The pre-existing tulip head engagement member 276 may comprise a first member 278 and a second member 280, the first member 278 being separated from the second member 280 by a space, gap, or distance 281. The first member 278 may be an elongated body, or arm, extending away from the tulip to tulip head attachment connector intermediate portion 246. The second member 280 may be an elongated body, or arm, extending away from the tulip to tulip head attachment connector intermediate portion 246, and aligned in a generally parallel orientation relative to the first member 278, thus forming a generally L-shaped or J-shaped pre-existing tulip head engagement member 276.

The tulip to tulip head attachment connector intermediate portion 246 may include an elongated body or surface 282 separating the upper portion 242 and the lower portion 244 by a space or distance 284, thus forming a channel sufficient in size to receive the preexisting tulip head 20 therein.

The tulip to tulip head attachment connector 240 is designed to engage with or secure to the pre-existing rod 22 secured to the preexisting tulip head 20. The tulip to tulip head attachment connector 240 comprises an upper portion 241, a lower portion 243, and an intermediate portion 245 separating the upper portion 241 and the lower portion 243. The upper portion 241 is configured to engage with an add-on tulip head 247. The lower portion 243 is configured to engage with the pre-existing rod 22.

Figure 12F:
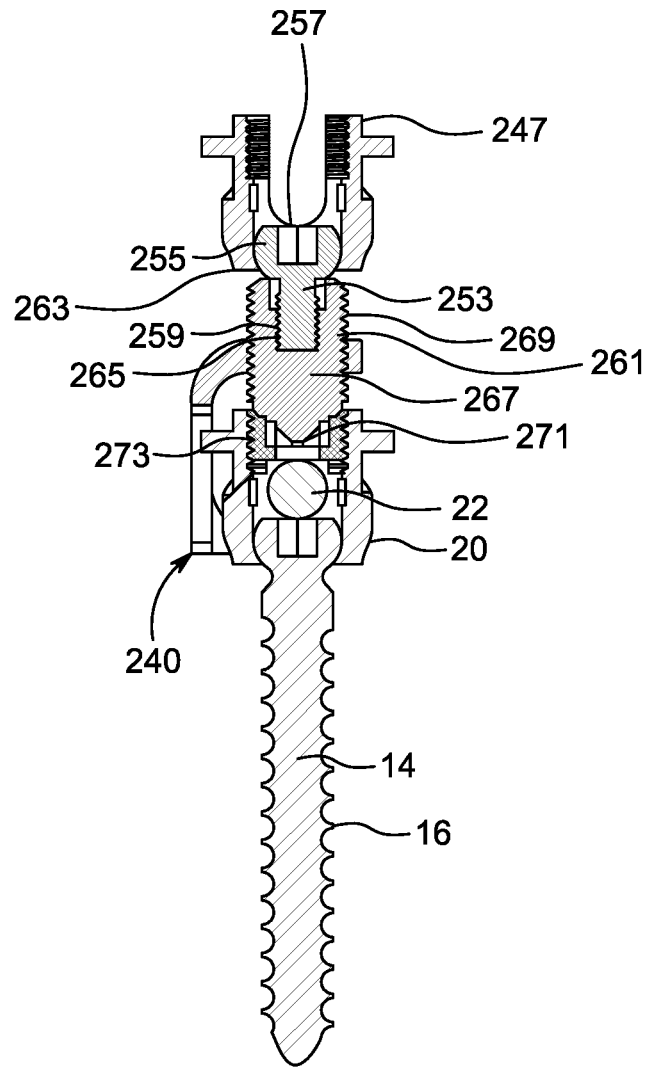
FIG. 12F is a cross section view of the add on screw system illustrated in FIG. 12A, taken along lines C-C in FIG. 12D.
Figure 13:
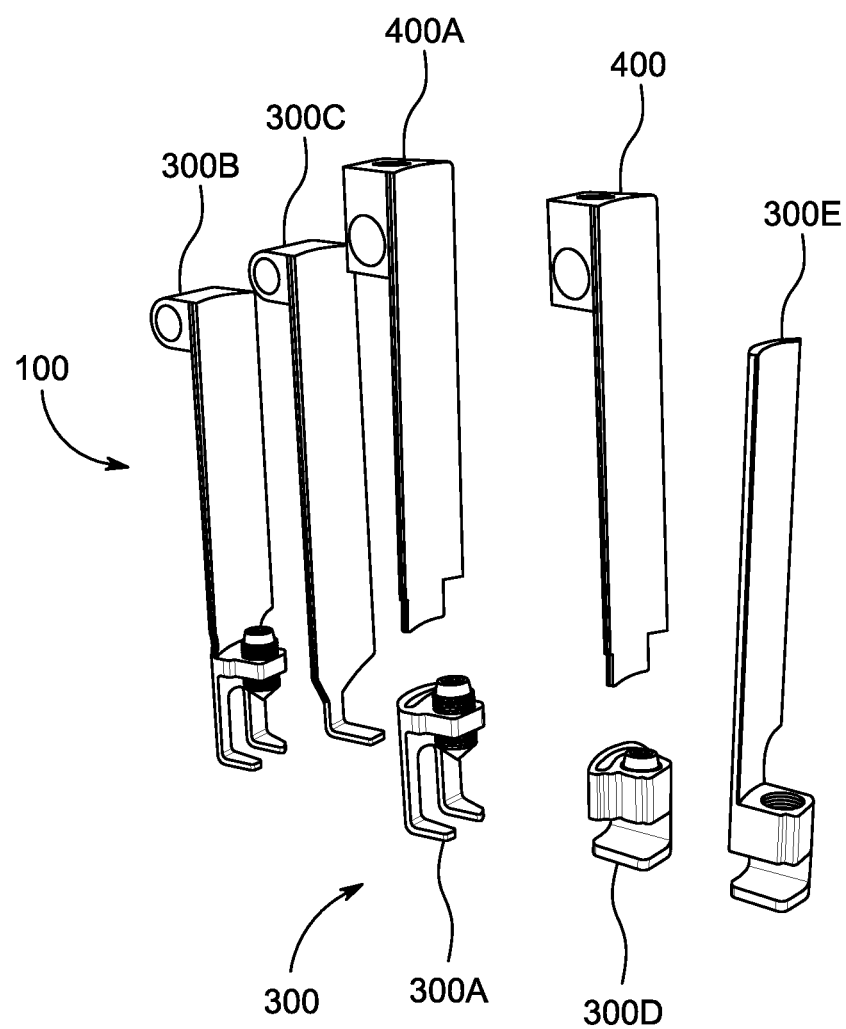
FIG. 13 is a perspective view of embodiments of the add-on screw system connectors and retractors.
Figure 14:
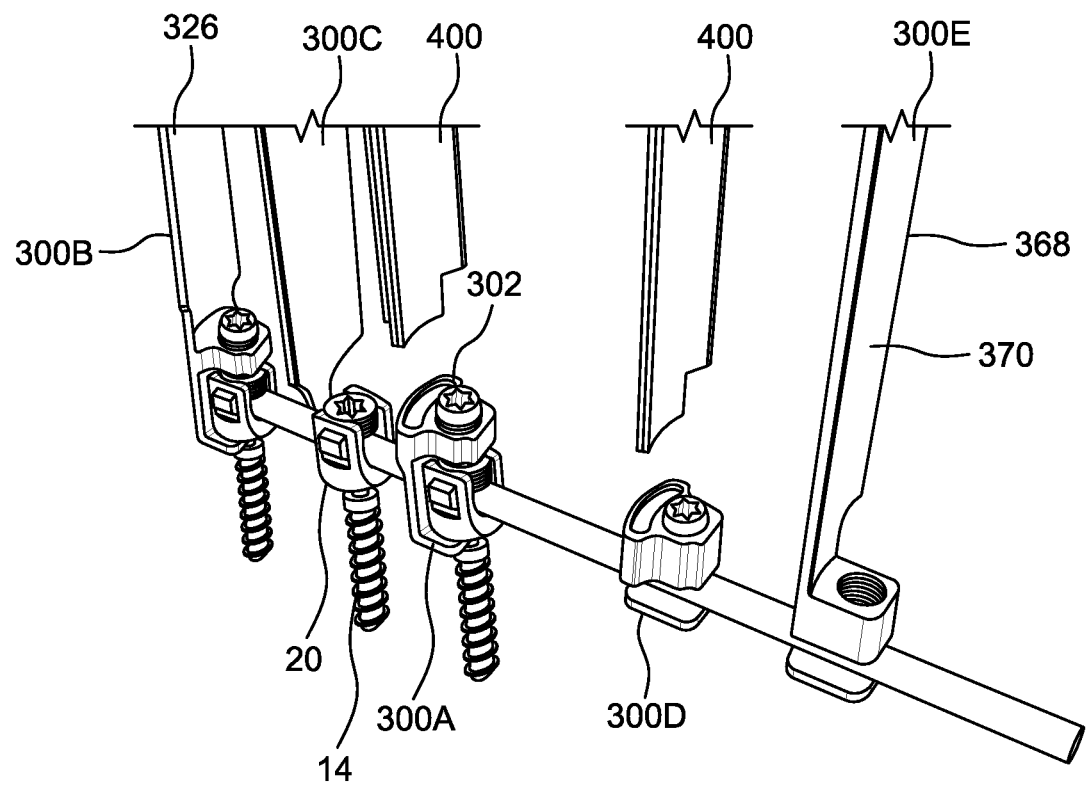
FIG. 14 is a perspective view of the embodiments of the add-on screw system connectors and retractors, shown interacting with preexisting pedicle screws or rods.
Figure 15:
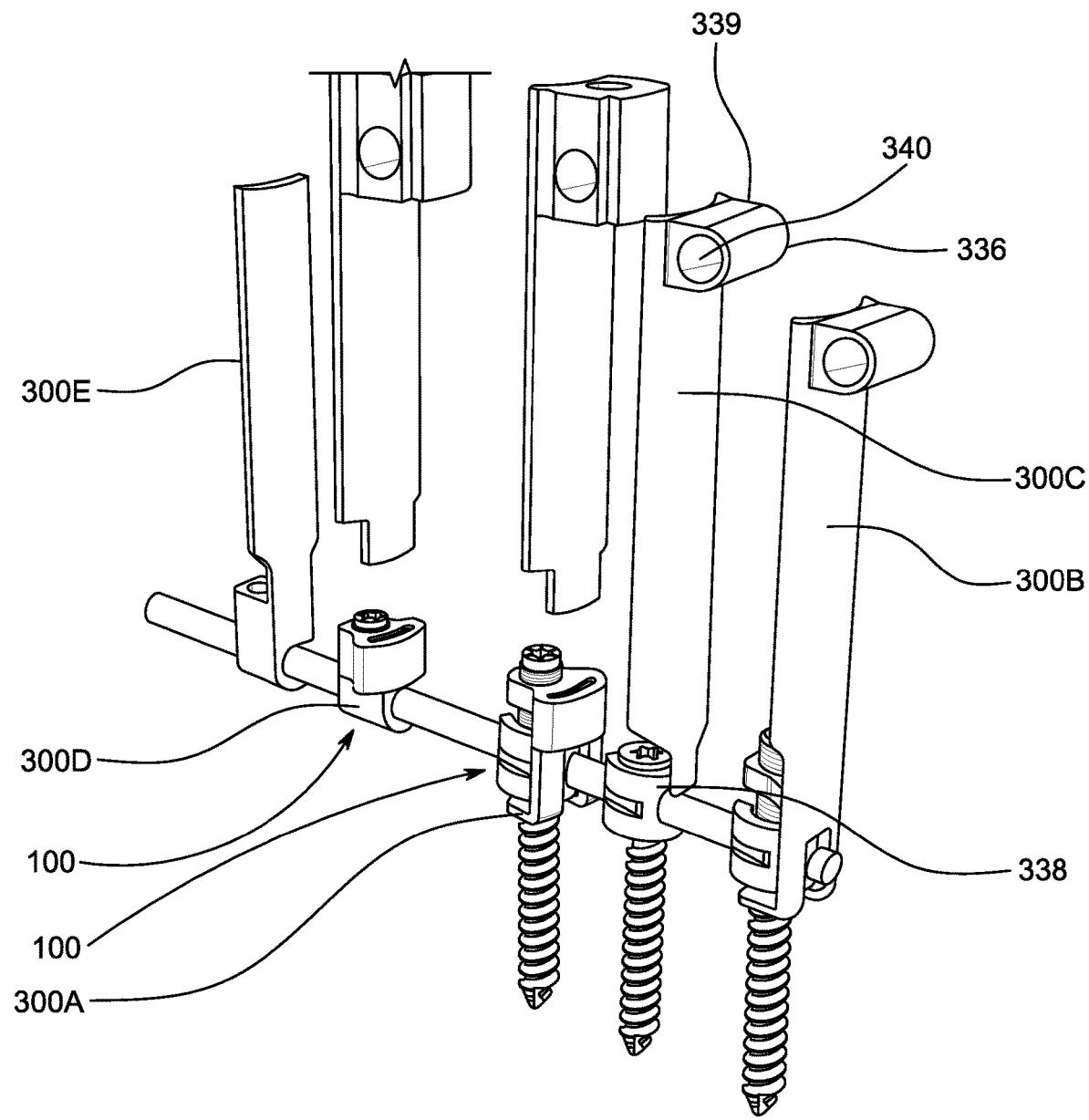
FIG. 15 is an alternative perspective view of the add-on screw system connectors and retractors illustrated in FIG. 14.
Figure 16:
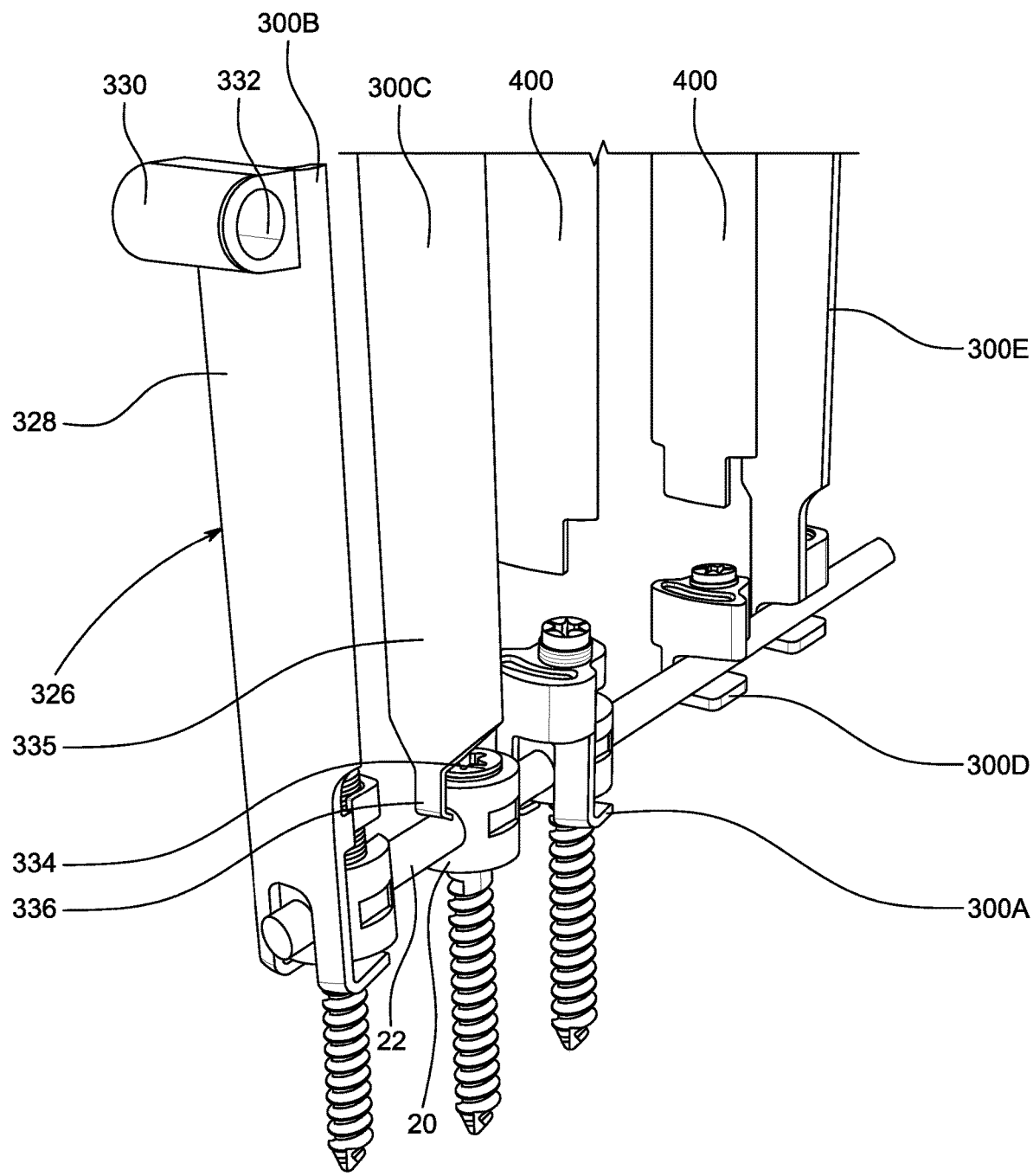
FIG. 16 is an alternative perspective view of the add-on screw system connectors and retractors illustrated in FIG. 14.
Figure 17:
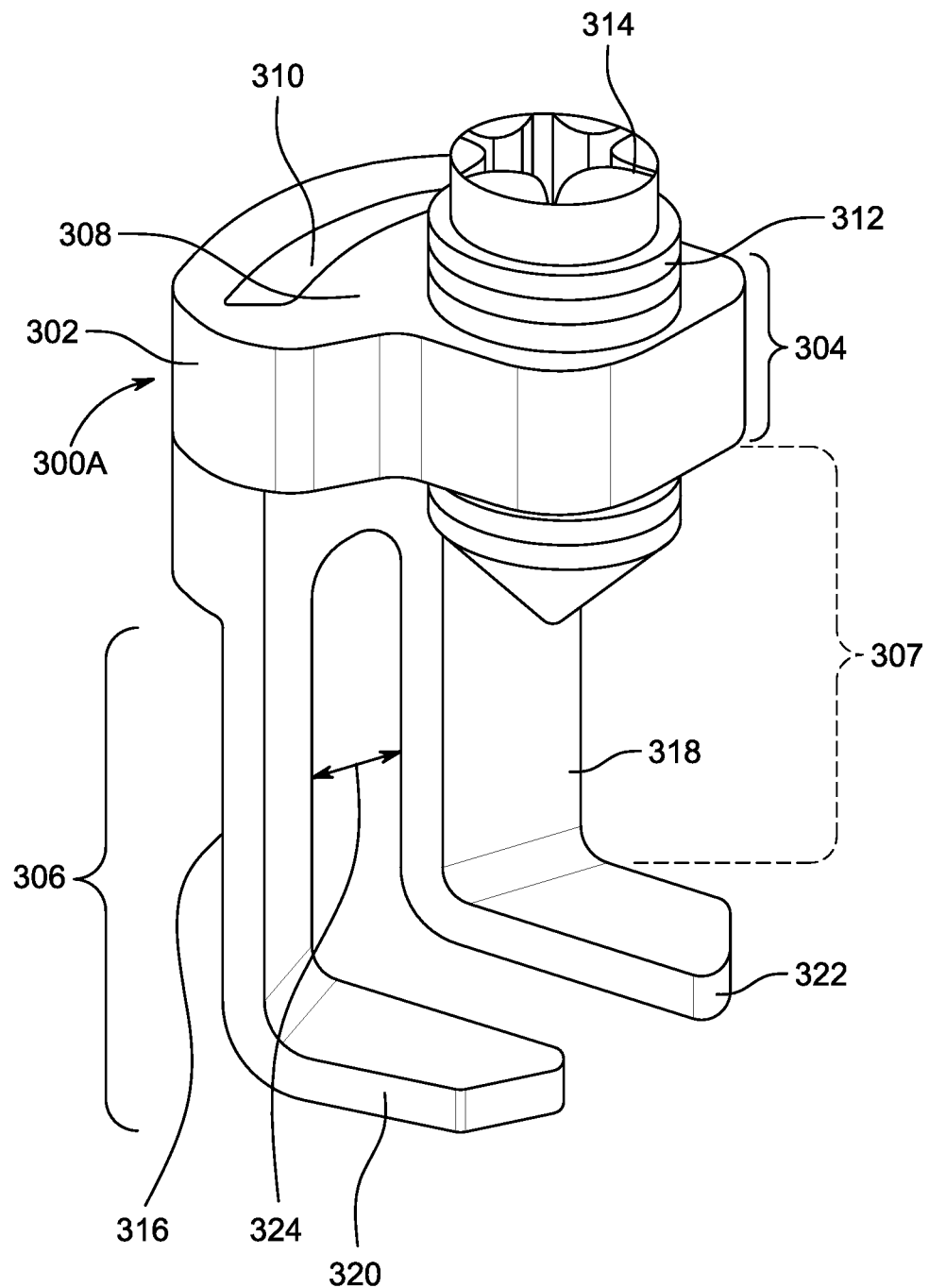
FIG. 17 is an illustrative embodiment of an add on screw system connector configured to engage with or secure to a pedicle screw tulip.
Figure 18:
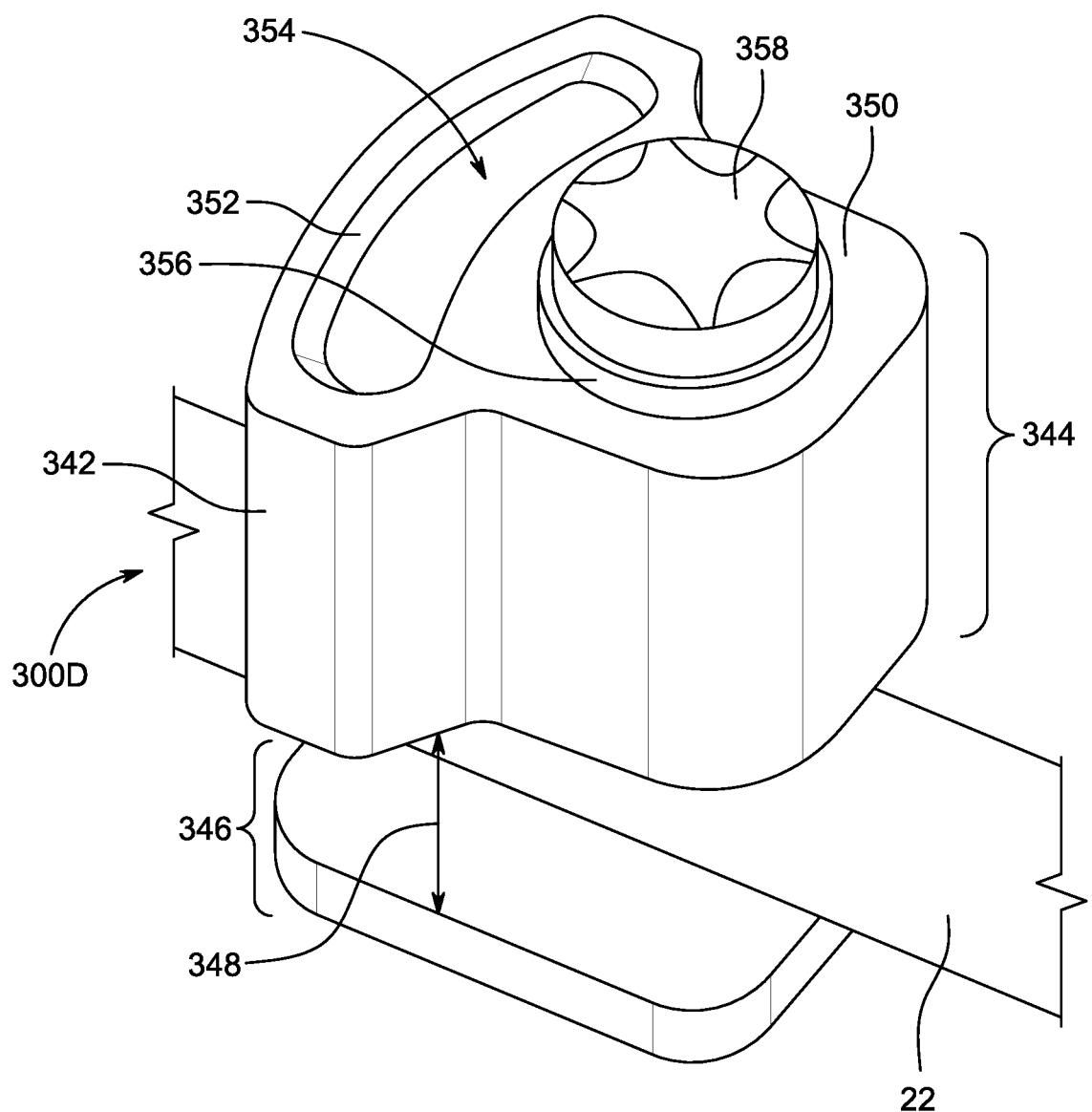
FIG. 18 is an illustrative embodiment of an add on screw system connector configured to engage with or secure to a surgical rod.
Figure 19:
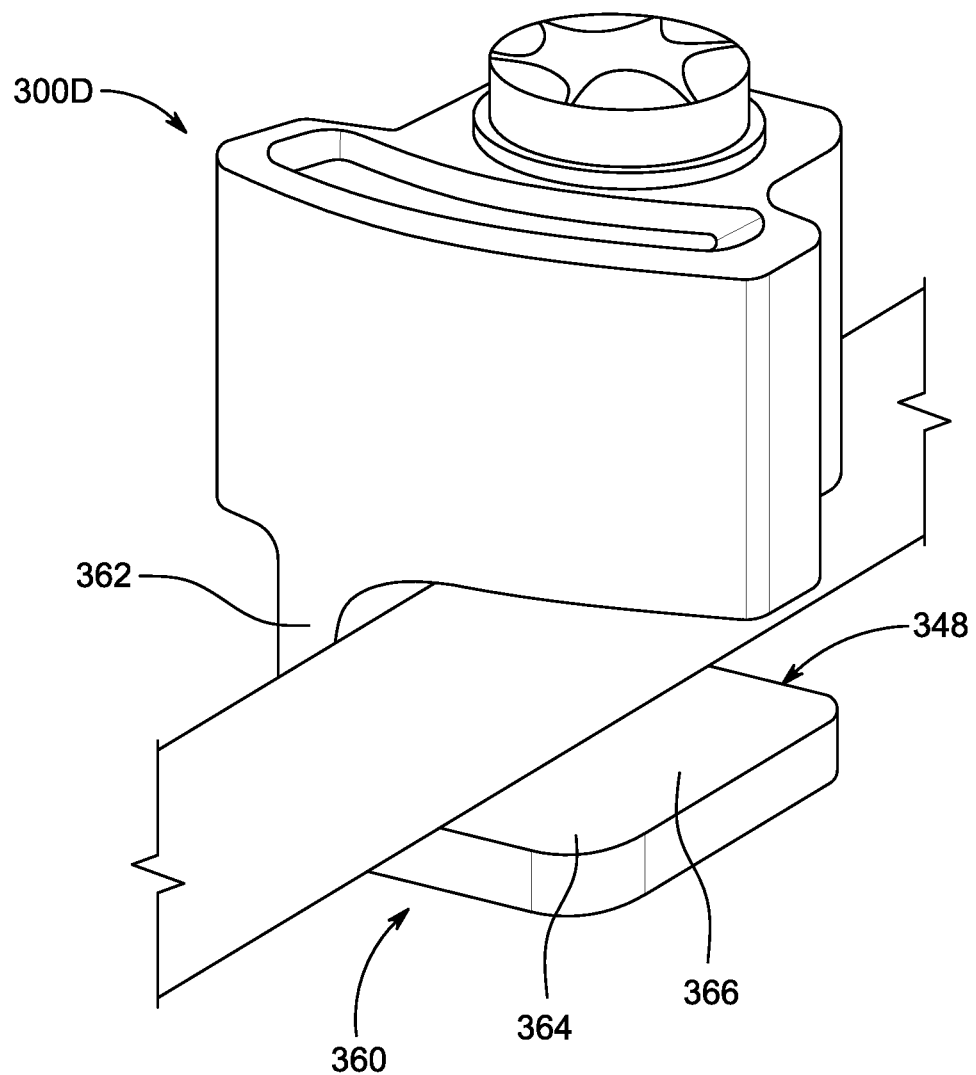
FIG. 19 is an alternative view of the add on screw system connector shown in FIG. 18.

The upper portion 241 comprises a surface 249 having an opening 251 sized and shaped to receive and hold therein an add-on spherical screw 253. The add-on spherical screw 253 is designed to fix the add-on tulip head 247 in place. As seen in FIG. 12F, the add-on spherical screw 253 includes an upper spherical body 255, sized and shaped to fit within a seat 257 of the add-on tulip head 247, and a threaded body 259. While illustrated as having a spherical body 255 to provide the add-on tulip head 247 polyaxial movement, the add-on spherical screw 253 may include a body having a different shape. The add-on spherical screw threaded body 259 is designed to secure to an attachment fixing set screw 261. The attachment fixing set screw 261 includes an opening 263 with corresponding inner threading 265. The attachment fixing set screw 261 may include a body 267 having an outer threading 269, and terminating in a conical shaped end 271, thus allowing the attachment fixing set screw 261 to tighten a pre-existing tulip head set screw 273 secured within the preexisting tulip head 20.

The tulip to tulip head attachment connector lower portion 243 comprises a pre-existing tulip head engagement member 275. The pre-existing tulip head engagement member 275 may comprise a first member 277 and a second member 279, the first member 277 being separated from the second member 279 by a space, gap, or distance 283. The first member 277 may be an elongated body, or arm, extending away from tulip to tulip head attachment connector intermediate portion 245. The second member 279 may be an elongated body, or arm, extending away from tulip to tulip head attachment connector intermediate portion 245, and aligned in a generally parallel orientation relative to the first member 277, thus forming a generally L-shaped or J-shaped pre-existing tulip head engagement member 275.

The tulip to tulip head attachment connector intermediate portion 245 may include an elongated body or surface 285 separating the upper portion 241 and the lower portion 243 by a space or distance), thus forming a channel sufficient in size to receive the preexisting tulip head 20 therein. The tulip to tulip head attachment connector intermediate portion 245 may also include a cut out section, or channel 287.

To aid in attaching to the preexisting rod 22, the pre-existing tulip head engagement member first member 277 and second member 279 may include a preexisting rod receiving member 289, illustrated herein as a dimple or indentation. The preexisting rod receiving member 289 is sized and shaped to correspond with the curvature of the preexisting rod 22, thus providing a secure, snug and level fit between the two.

Referring to FIGS. 13-16, the add on screw system 100 may also comprise one or both of a connector, referred to generally as add on screw system connector 300, or individually as add on screw or rod connectors 300A, 300B, 300C, 300D, 300E or the like, and a retractor, referred to generally as add on screw system retractor blade 400. The add on screw system connector 300 is configured to secure to an existing pedicle screw previously implanted into a patient and/or to a previously implanted rod at one end and secure to or include a retractor blade. The add on screw system connector 300A may comprise a main body 302 having an upper portion 304 configured to engage with pedicle screw set screw and/or a retractor blade, and a lower portion 306 configured to engage with a preexisting surgical device, such as a previously implanted pedicle screw tulip 20. The add on screw system connector main body upper portion 304 is separated from the add on screw system connector main body lower portion 306 by a space or channel 307. The space or channel 307 is sized and shaped to allow an existing pedicle screw tulip 20 previously implanted into a patient to fit and or rest therein.

The add on screw system connector main body 302 upper portion 304 comprises an upper surface 308 having a retractor blade receiving member 310. The retractor blade receiving member 310 is illustrated as an opening sized and shaped to receive and hold therein at least a portion of a retractor blade, such as add on screw system retractor blades 400A. A secondary opening 312 is sized and shaped to receive a set screw 314, which, when in use, allows the add on screw system connector 300 to secure to the existing pedicle screw tulip 20 previously implanted into a patient.

The add on screw system connector 300A main body lower portion 306 includes two arms or finger-like extensions 316 and 318, extending or oriented in a direction down or away from the add on screw system connector main body 302. The two arms or finger-like extensions 316 and 318 may terminate in pedicle screw system engaging members 320 and 322, illustrated herein as hook shaped ends. The two arms or finger-like extensions 316 and 318 may be arranged in a parallel manner and separated by a space or distance 324. The space or distance 324 is sufficient to allow the arms or finger-like extension pedicle screw system engaging members 320 and 322 to engage with or secure to two different positions along or to the existing pedicle screw tulip 20 previously implanted into a patient. Preferably, the two arms or finger-like extensions 316 and 318 are arranged and oriented to allow the arms or finger-like extension pedicle screw system engaging members 320 and 322 to engage with or secure to the bottom of the tulip 20 (or rod 22), or to the area where the pedicle screw threaded body 16 meets or extends out from the tulip 20 (or rod 22). While the add on screw system connector 300A is shown with two arms or finger-like extensions 316 and 318, an alternative embodiment may include a single arm or finger-like extension 316 or 318.

The add on screw system connector 300B includes all the same structural components as that described for the add on screw system connector 300A except for the inclusion of the retractor blade receiving member 310. As an alternative, the add on screw system connector 300B comprises a retractor blade 326 integrally formed therein. The retractor blade 326 includes an elongated body 328, terminating in a mounting structure 330 having an opening 332 (see FIG. 16). The mounting structure 330 allows the securing of the retractor blade 326 to a structure outside of the patient.

The add on screw system connector 300C is configured to secure to the area where the set screw 334 rests inside the tulip 20, resting above the preexisting rod 22. Accordingly, the add on screw system connector 300C includes an elongated body 335 having a pedicle screw system engaging member 336 at one end. The pedicle screw system engaging member 336 includes an L-shaped member 338 sized and shaped to fit within the area where the set screw 334 rests inside the preexisting tulip 20. At or along the opposite end of the elongated body 336, the add on screw system connector 300C may include a mounting structure 339 having an opening 340.

The add on screw system connector 300D is configured to engage with and secure to a previously implanted rod 22. The add on screw system connector 300D may comprise a main body 342 having an upper portion 344 configured to engage with pedicle screw set screw and retractor blade, and a lower portion 346 configured to engage with a preexisting surgical device, such as a previously implanted rod 22. The add on screw system connector main body upper portion 344 is separated from the add on screw system connector main body lower portion 346 by a space 348 defining a channel sized and shaped to receive a portion of the rod 22 previously implanted into a patient to fit and rest therein.

The add on screw system connector main body upper portion 344 comprises an upper surface 350 having a retractor blade receiving member 352. The retractor blade receiving member 352 is illustrated as an opening 354 sized and shaped to receive and hold therein at least a portion of a retractor blade, such as the add on screw system retractor blades 400. A secondary opening 356, preferably threaded, is sized and shaped to receive a set screw 358, which, when in use, allows the add on screw system connector 300D to secure to the rod 22. The add on screw system connector main body lower portion 346 includes a rod engagement member 360, illustrated herein as a first member 362 and a second member 364, where the first member 362 is an elongated body extending down or away from the screw system connector main body 342. The second member 364 may comprise a surface 366 aligned in a perpendicular or angled relationship to the first member 362, thus forming an L-shaped or J-shaped end.

The add on screw system connector 300E includes all the same structural components as that described for the add on screw system connector 300D except for the inclusion of the retractor blade receiving member 352. As an alternative, the add on screw system connector 300E comprises a retractor blade 368 integrally formed therein. The retractor blade 368 includes an elongated body 370. The elongated body 370 may terminate in a mounting structure, similar to mounting structure 330.

Figure 20:
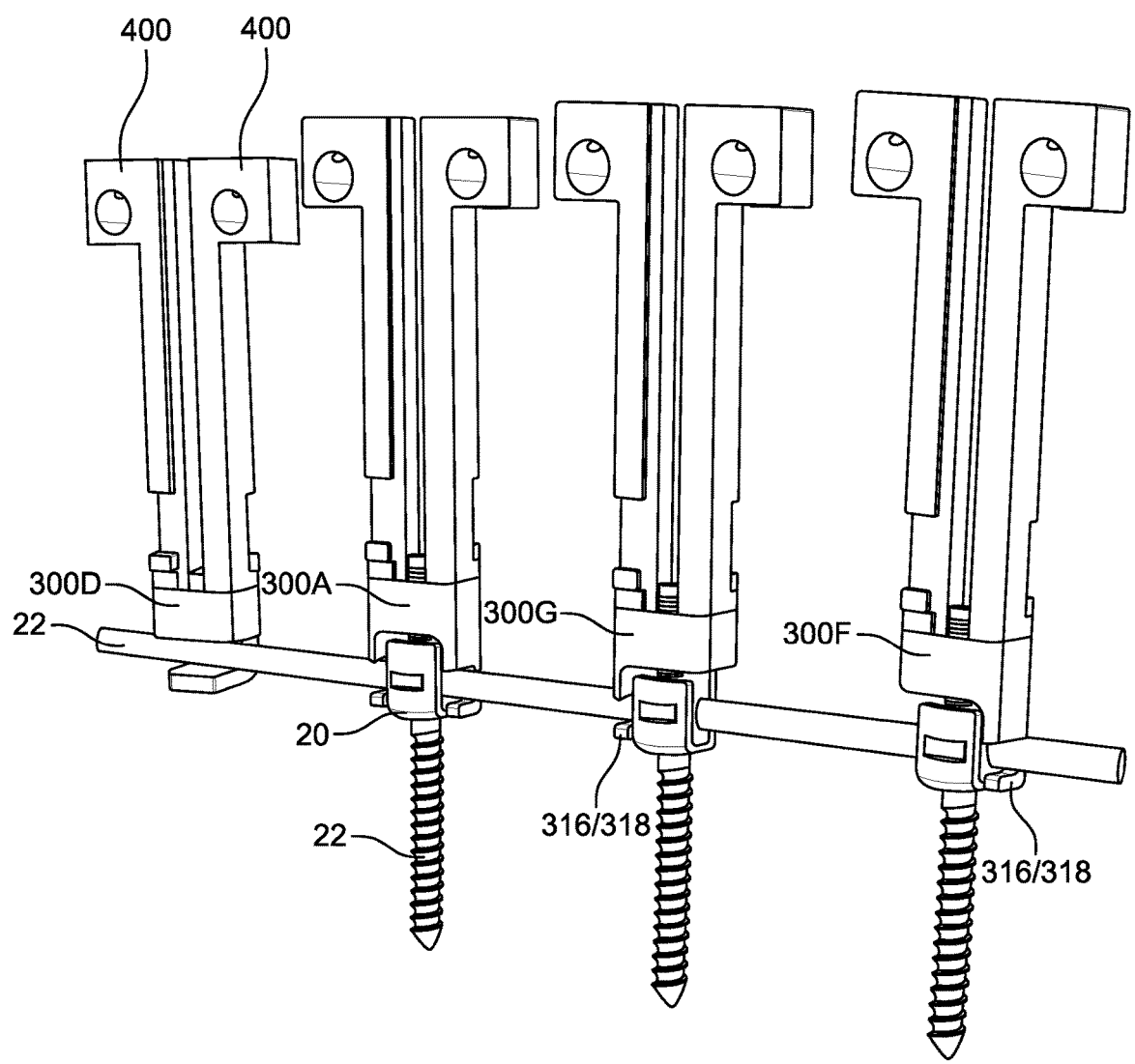
FIG. 20 illustrates the add on screw system connectors secured with multiple retractor blades.
Figure 21:
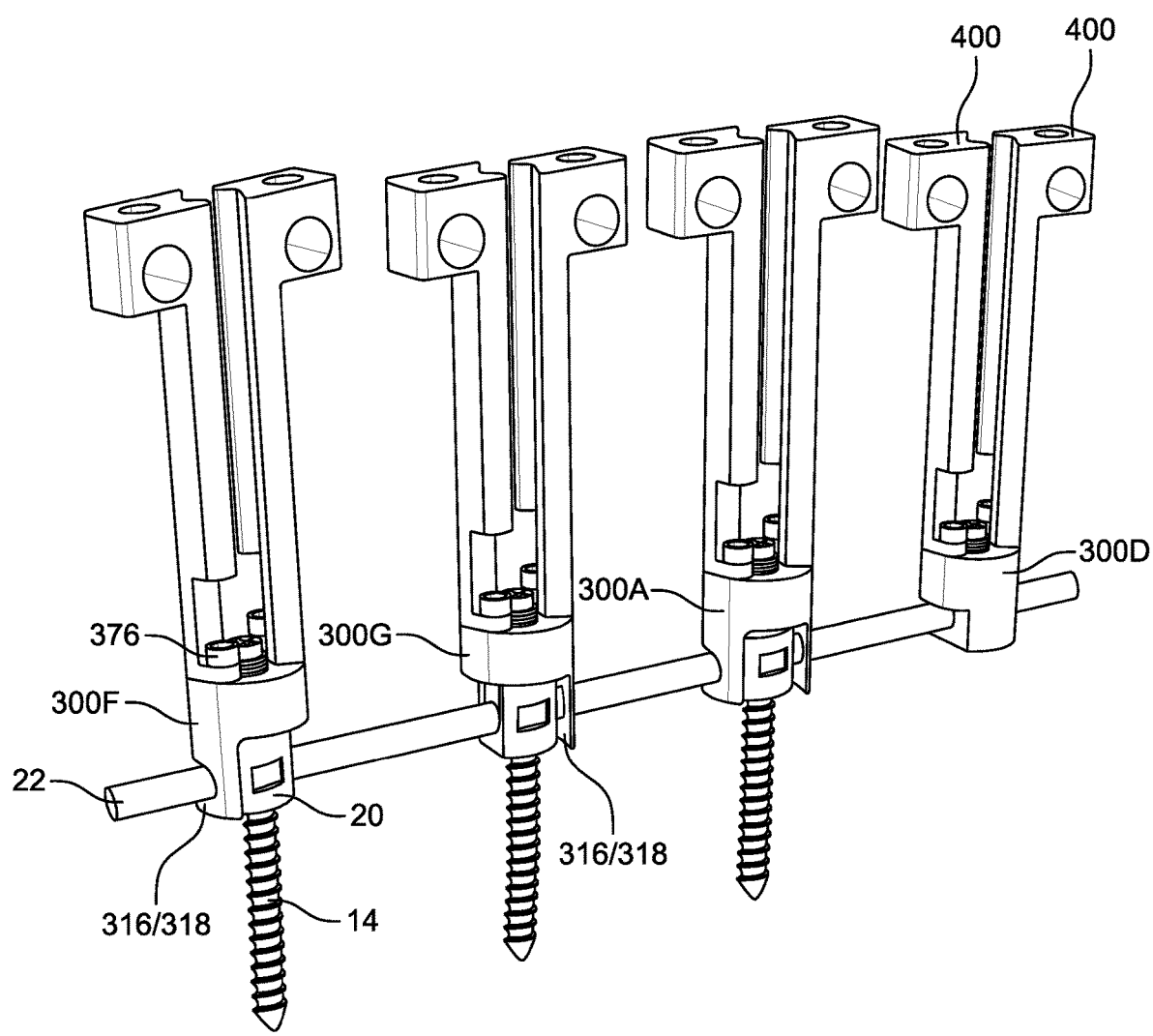
FIG. 21 is an alternative view of the add on screw system connectors secured with multiple retractor blades shown in FIG. 20.
Figure 22A:
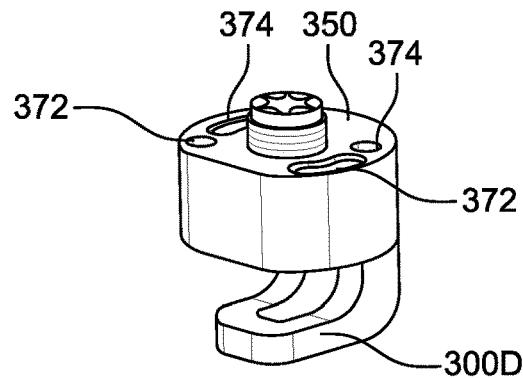
FIG. 22A illustrates an embodiment of the add on screw system connector adapted to secure with multiple retractor blades.
Figure 22B:
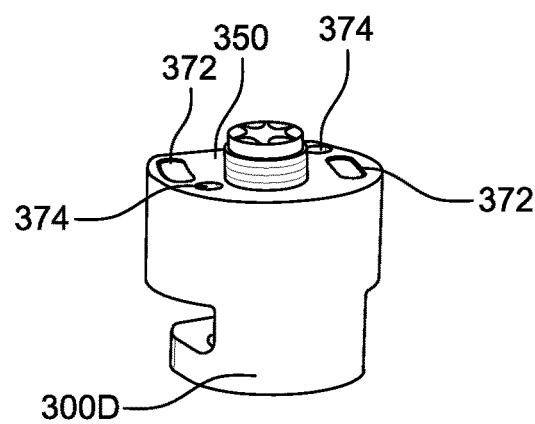
FIG. 22B illustrates an alternative view of the connector shown in FIG. 22A.
Figure 23A:
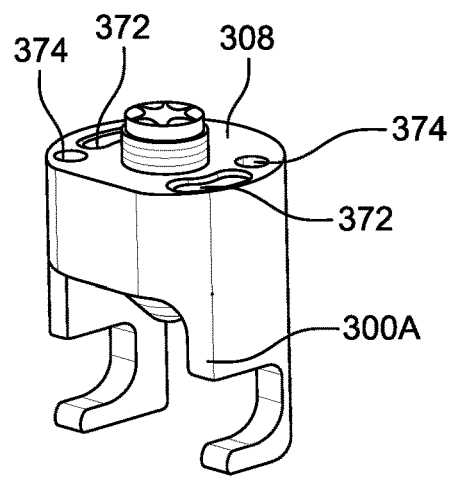
FIG. 23A illustrates an embodiment of the add on screw system connector adapted to secure with multiple retractor blades.
Figure 23B:
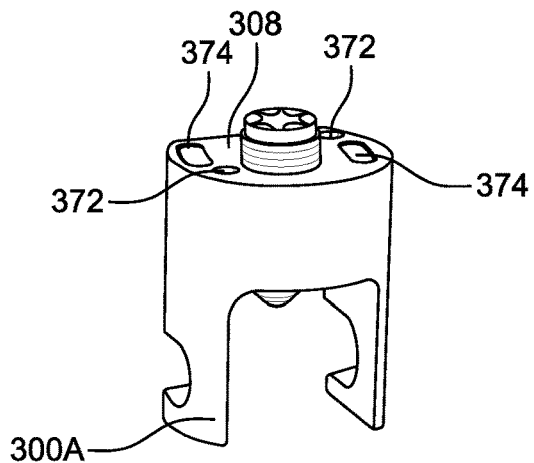
FIG. 23B illustrates an alternative view of the connector shown in FIG. 23A.
Figure 24A:
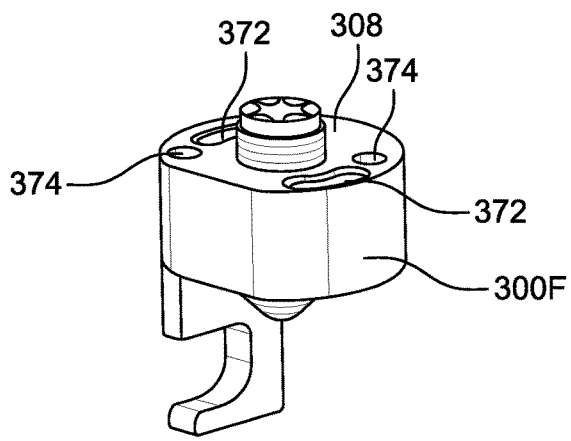
FIG. 24A illustrates an embodiment of the add on screw system connector adapted to secure with multiple retractor blades.
Figure 24B:
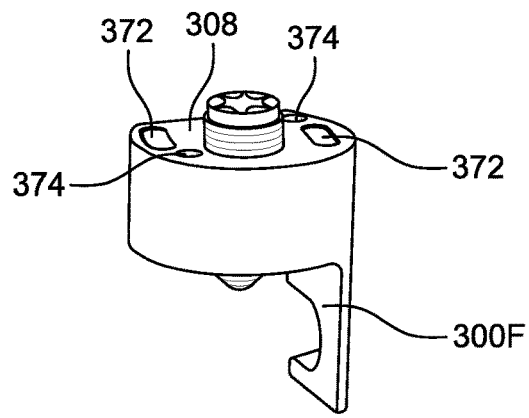
FIG. 24B illustrates an alternative view of the connector shown in FIG. 24A.
Figure 25A:
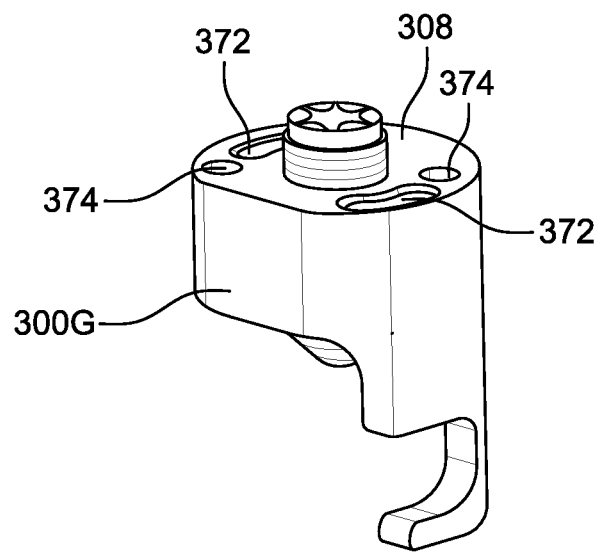
FIG. 25A illustrates an embodiment of the add on screw system connector adapted to secure with multiple retractor blades.
Figure 25B:
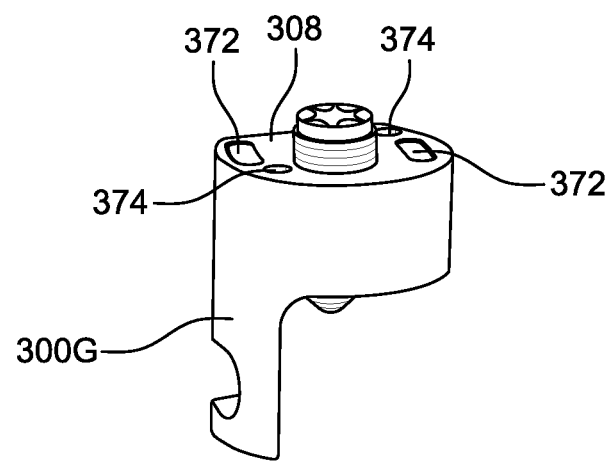
FIG. 25B illustrates an alternative view of the connector shown in FIG. 25A.

The add on screw system connectors 300 illustrated in FIGS. 13-19 are shown to include attachment with single retractor blade 400. However, the add on screw system connectors 300 may be adapted to secure with two retractor blades 400. FIGS. 20 and 21 illustrate embodiments of the add on screw system connectors 300A and 300D confirmed for multiple retractors. In addition, the figures include the add on screw system connectors 300A having a single left (300F) or right (300G) arms or finger-like extensions 316 or 318. FIGS. 22A-25B illustrate the add on screw system connectors 300 with the retractor blades 400 attached thereto. As shown, the upper surfaces (308 or 350) comprise multiple openings, two openings 372 for engagement (receiving) with a portion of the retractor blade 400 and two smaller openings for receiving screws 376, see FIG. 21. Use of the receiving screw 376 provides a mechanism to lock the retractor blade (400) down to the add on screw system connectors 300.

Figure 26B:
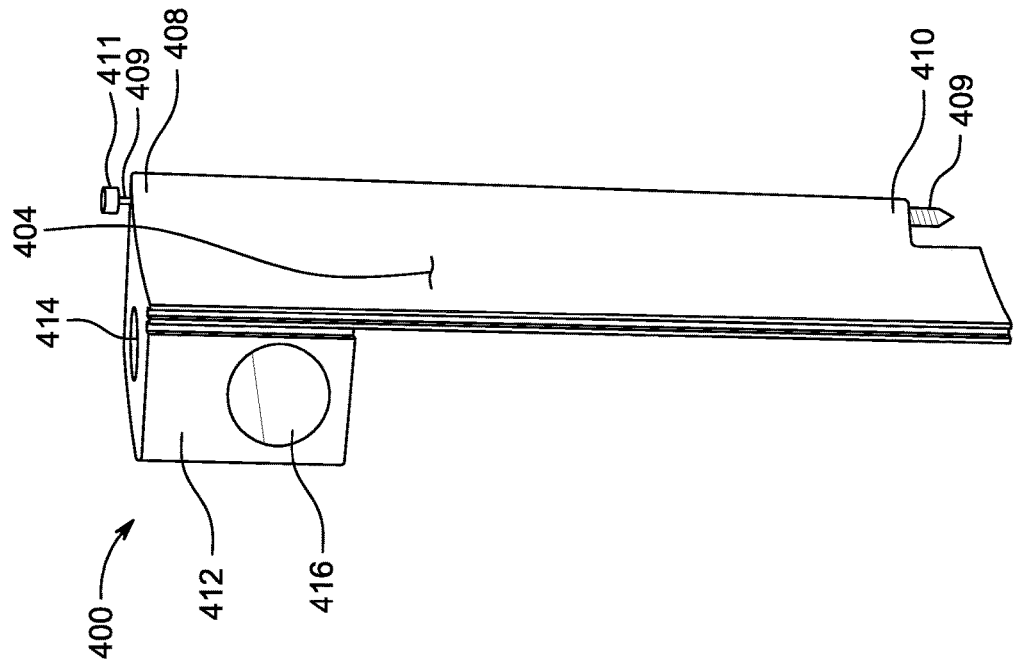
FIG. 26B illustrates the retractor blade shown with a screw for locking to a connector.
Figure 26A:
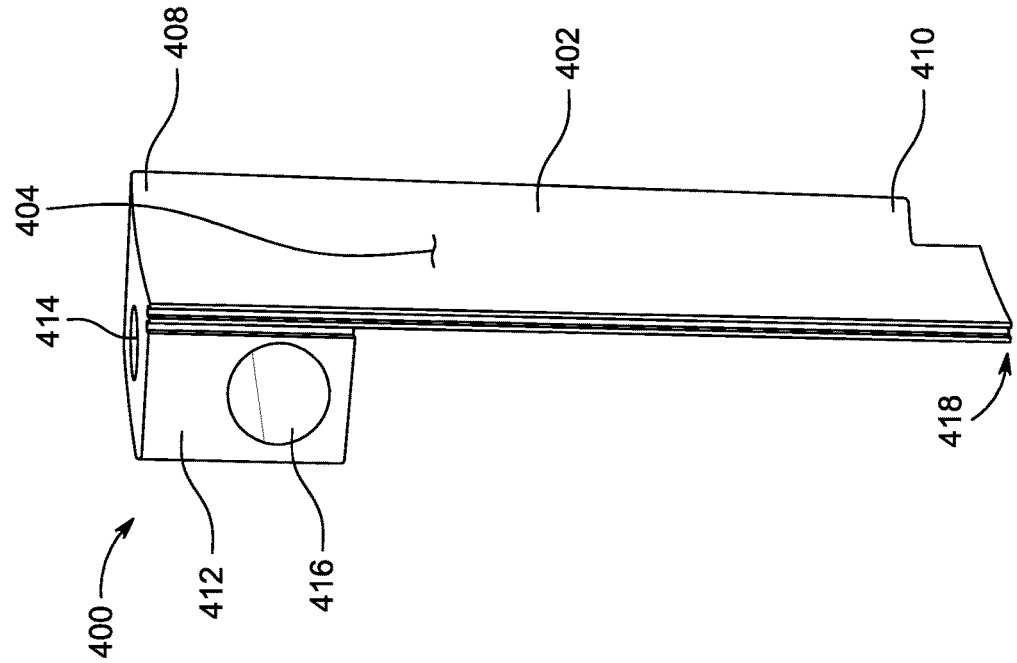
FIG. 26A is a perspective view of an illustrative embodiment of a retractor blade.
Figure 27:
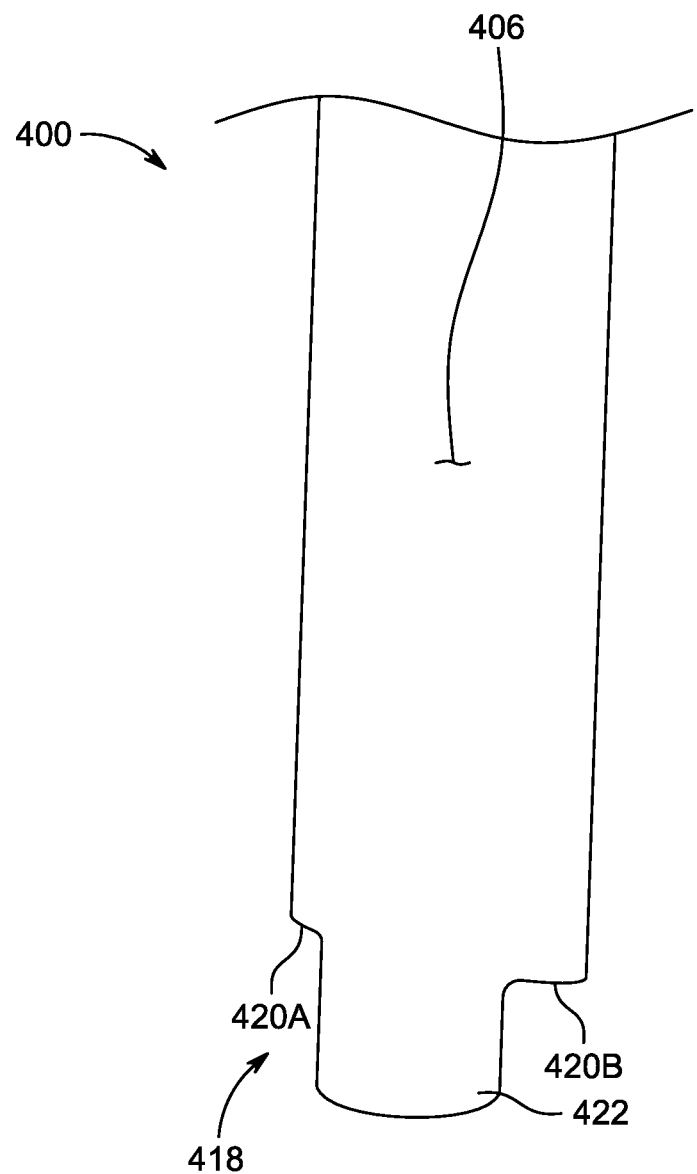
FIG. 27 is an alternative partial view of the retractor blade shown in FIG. 26.
Figure 28A:
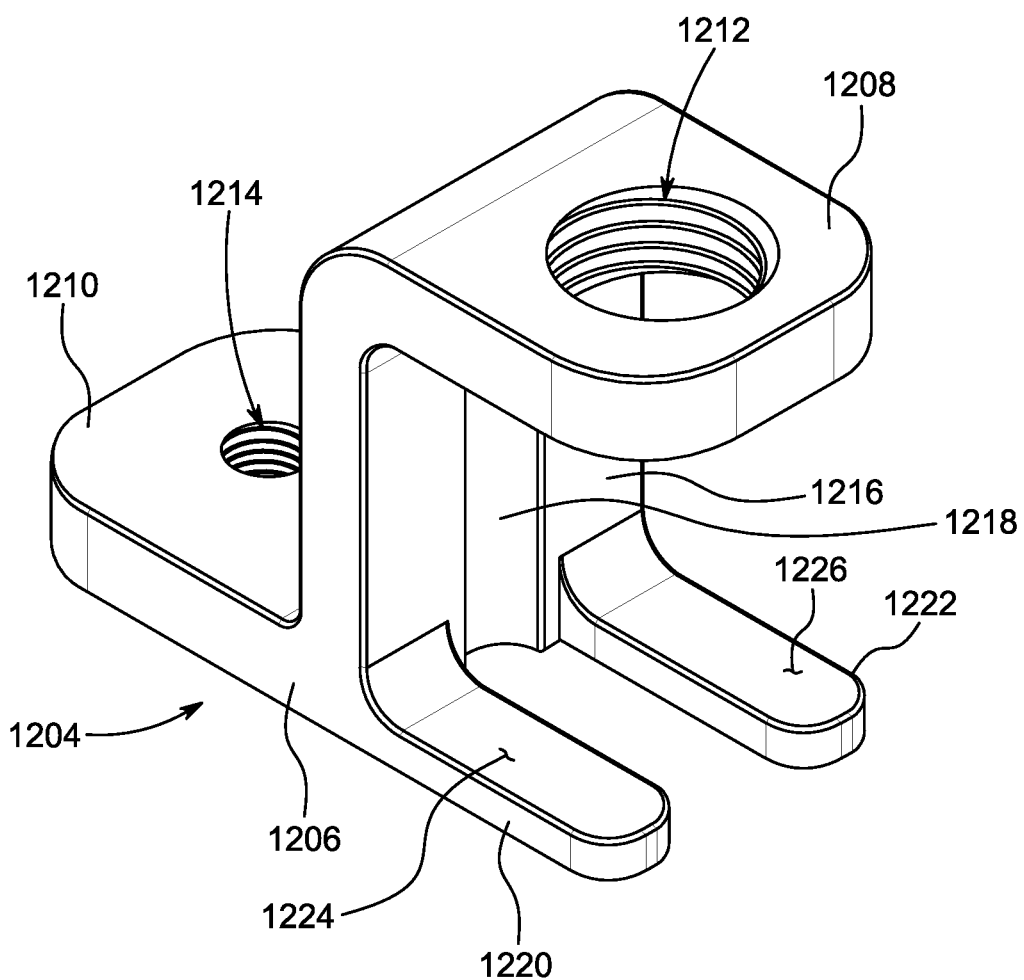
FIG. 28A is a perspective view of an illustrative embodiment of the one-piece side tulip connector.
Figure 28B:
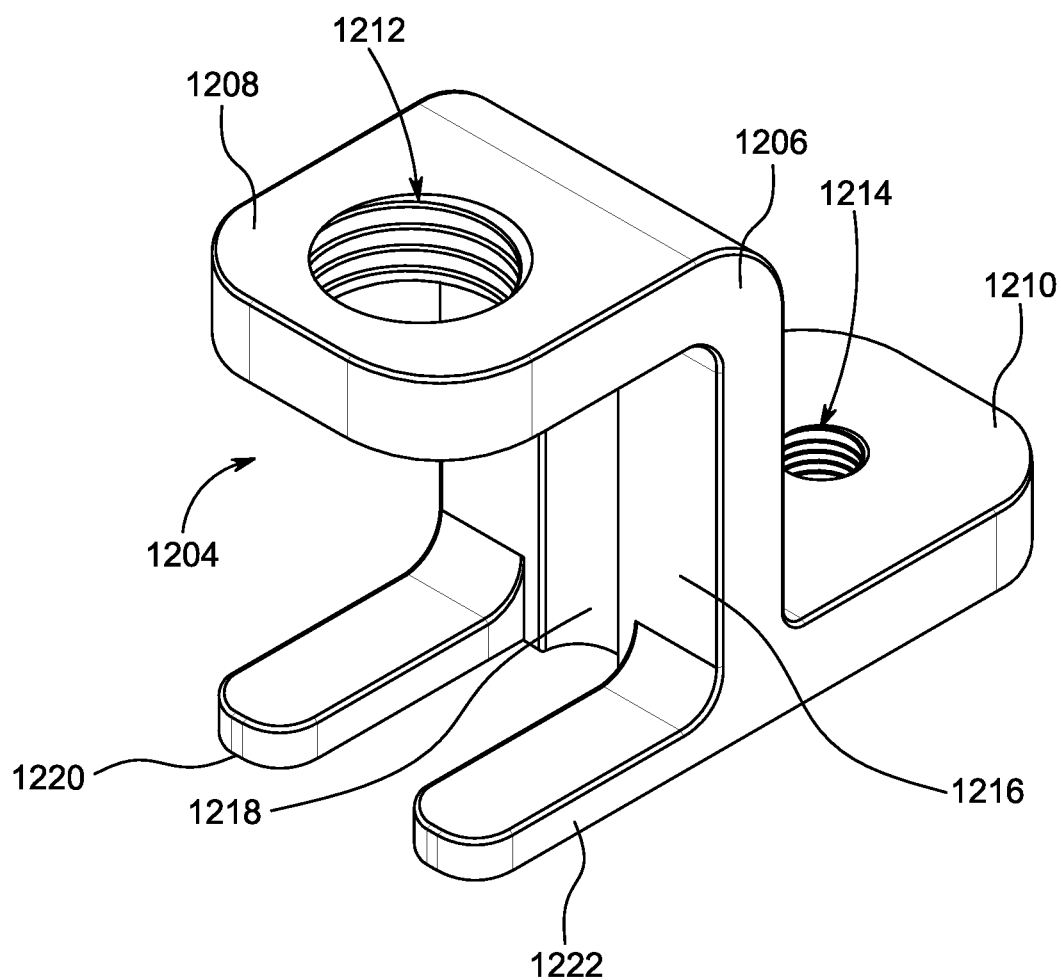
FIG. 28B is an alternative perspective view of the one-piece side tulip connector embodiment shown in FIG. 28A.
Figure 28C:
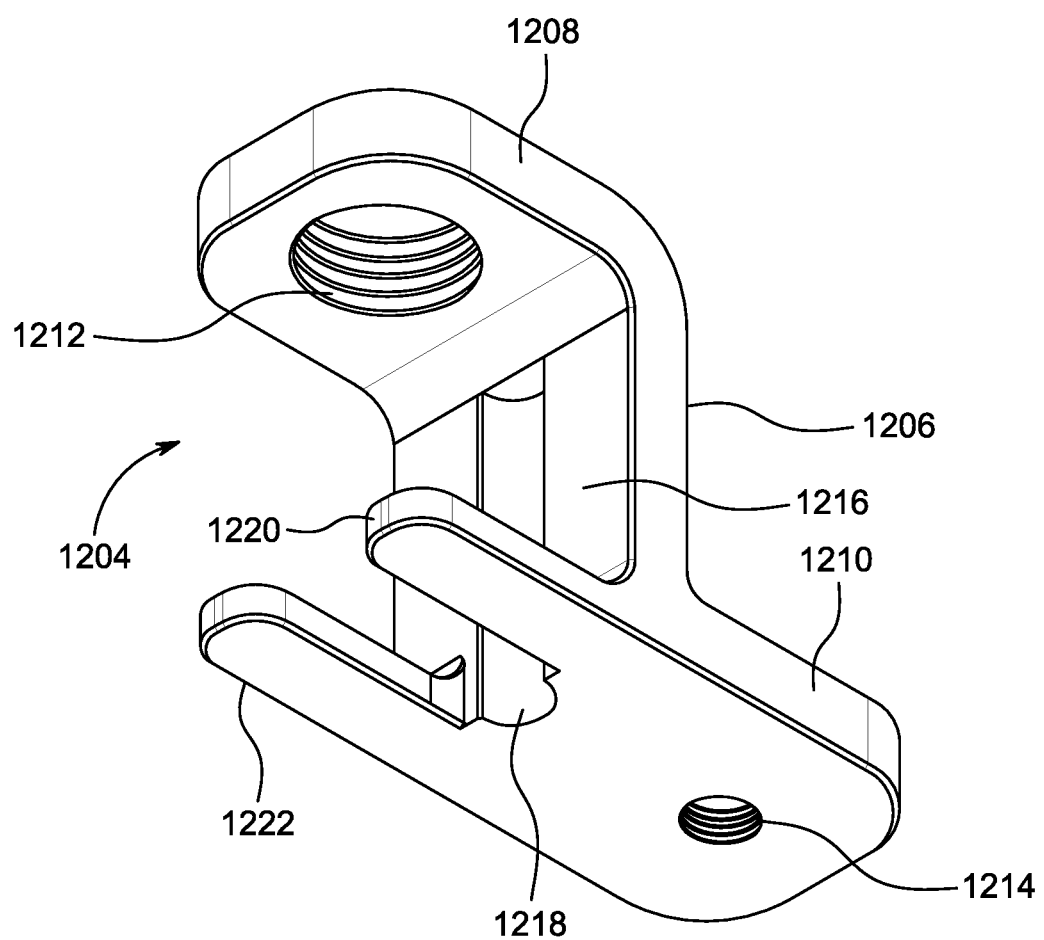
FIG. 28C is a bottom perspective view of the one-piece side tulip connector embodiment shown in FIG. 28A.
Figure 28D:
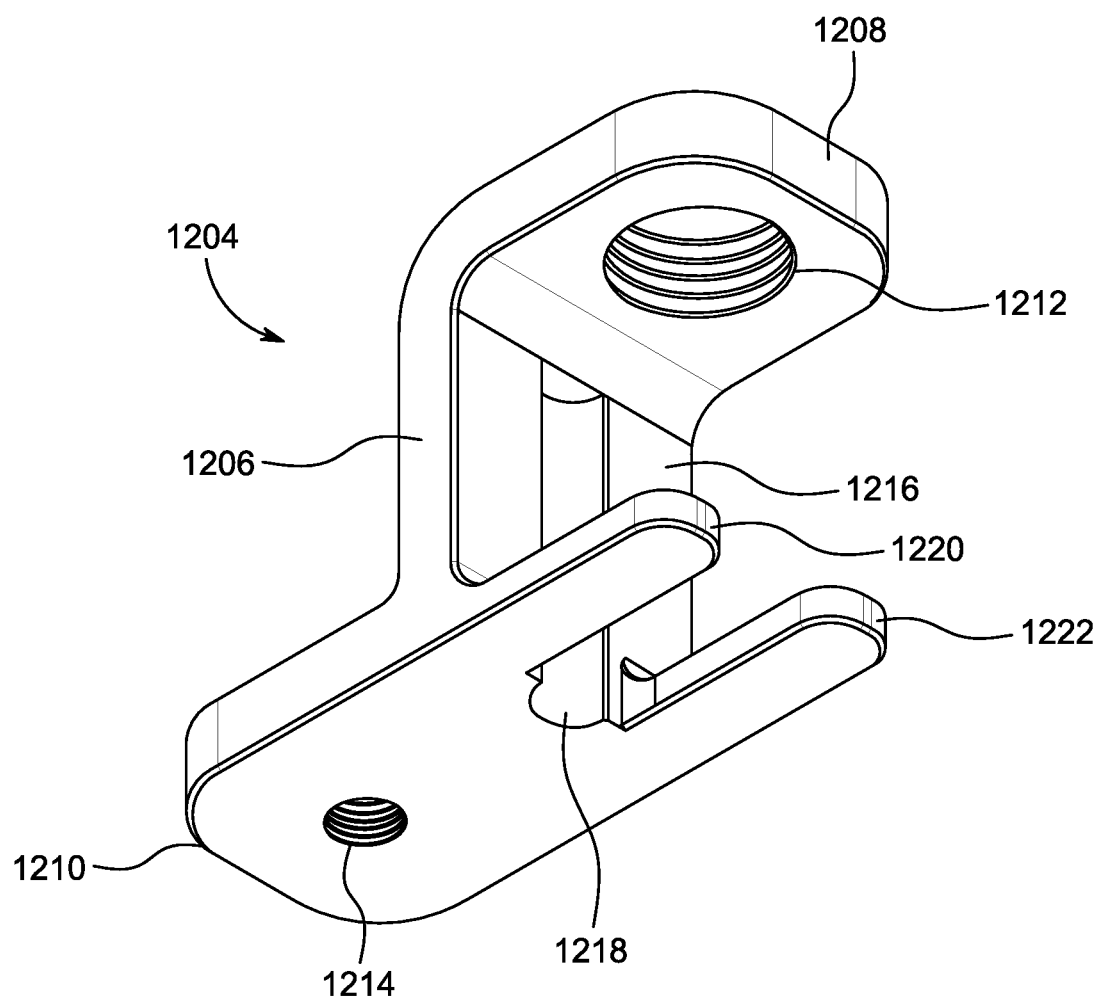
FIG. 28D is an alternative bottom perspective view of the one-piece side tulip connector embodiment shown in FIG. 28A.
Figure 28E:
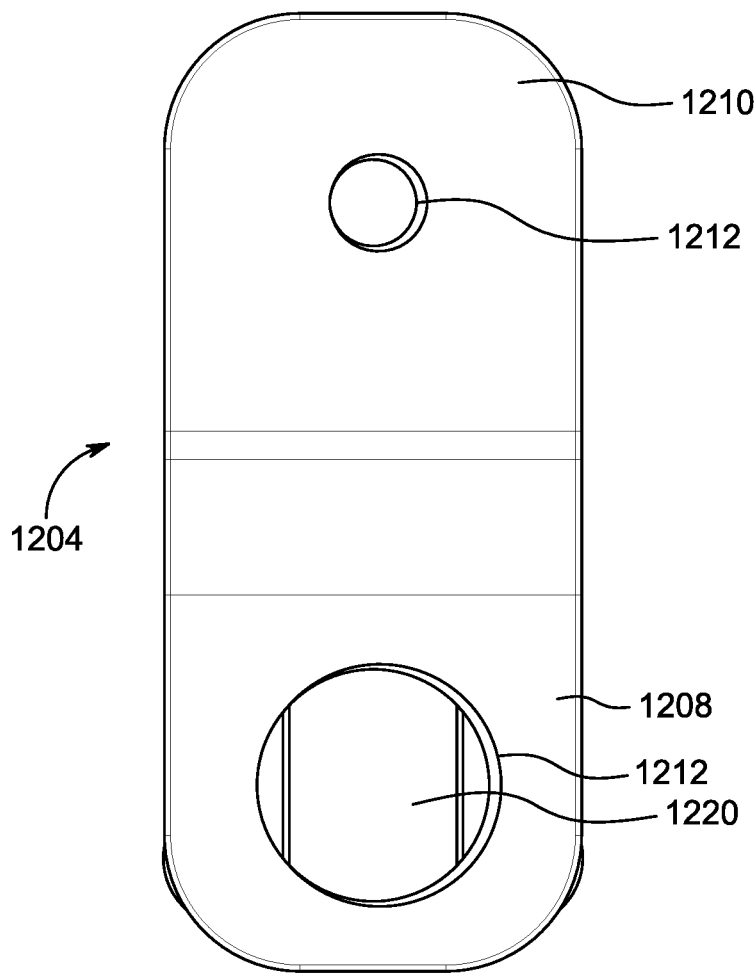
FIG. 28E is a top view of the one-piece side tulip connector embodiment shown in FIG. 28A.
Figure 28F:
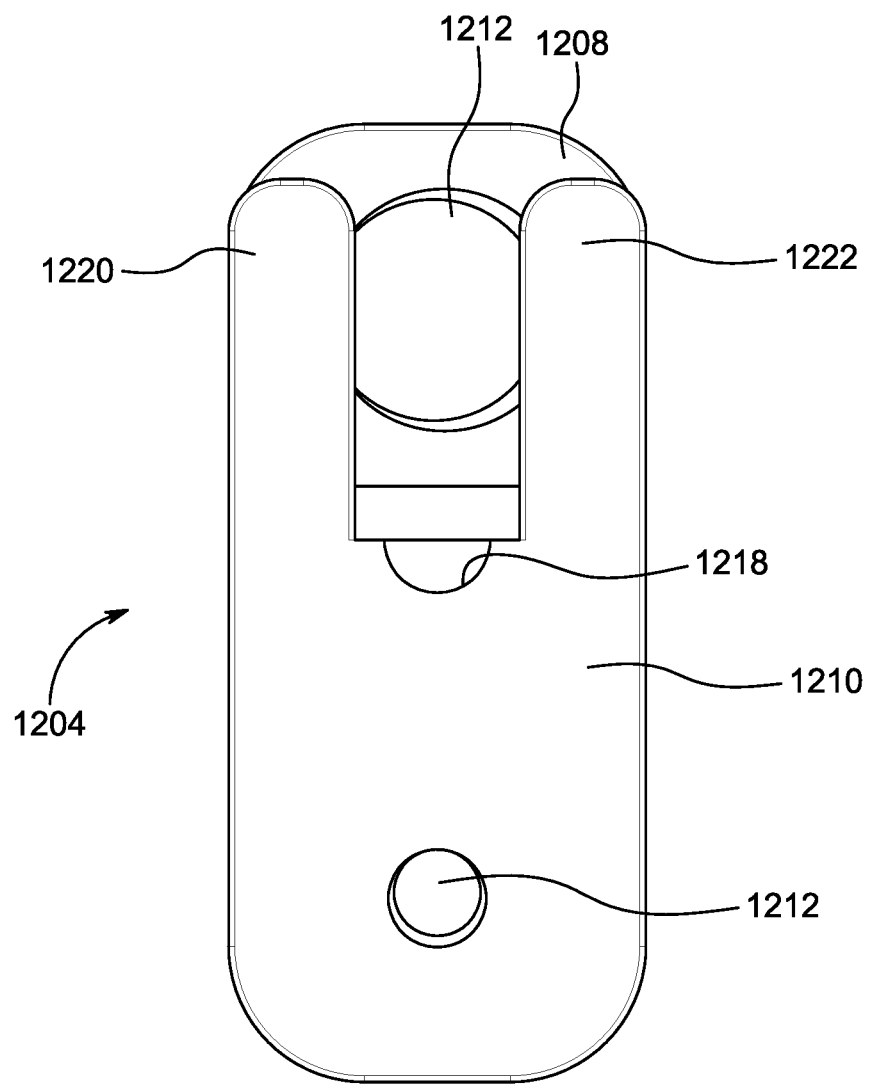
FIG. 28F is a bottom view of the one-piece side tulip connector embodiment shown in FIG. 28A.
Figure 28G:
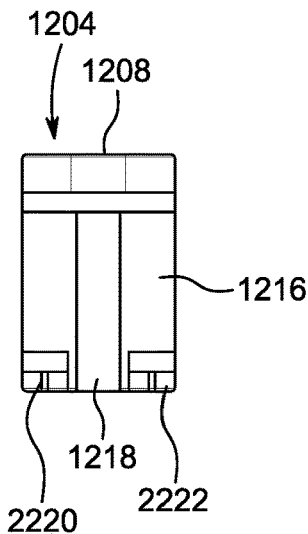
FIG. 28G is a front view of the one-piece side tulip connector embodiment shown in FIG. 28A.
Figure 28H:
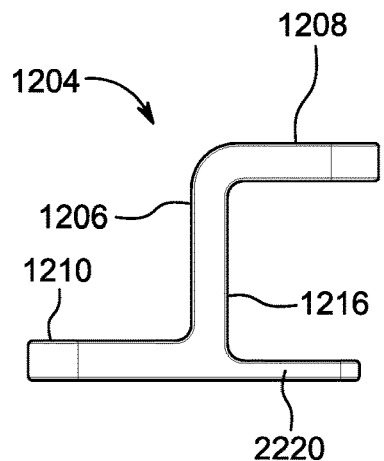
FIG. 28H is a right side of the one-piece side tulip connector embodiment shown in FIG. 28A.
Figure 28I:
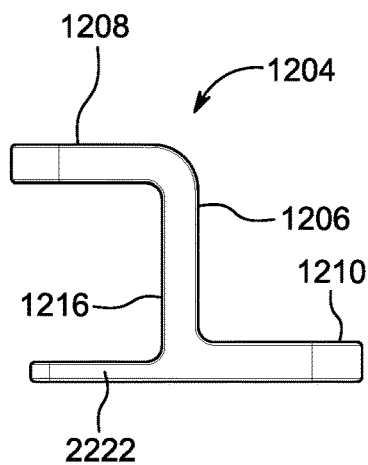
FIG. 28I is a left side of the one-piece side tulip connector embodiment shown in FIG. 28A.
Figure 29A:
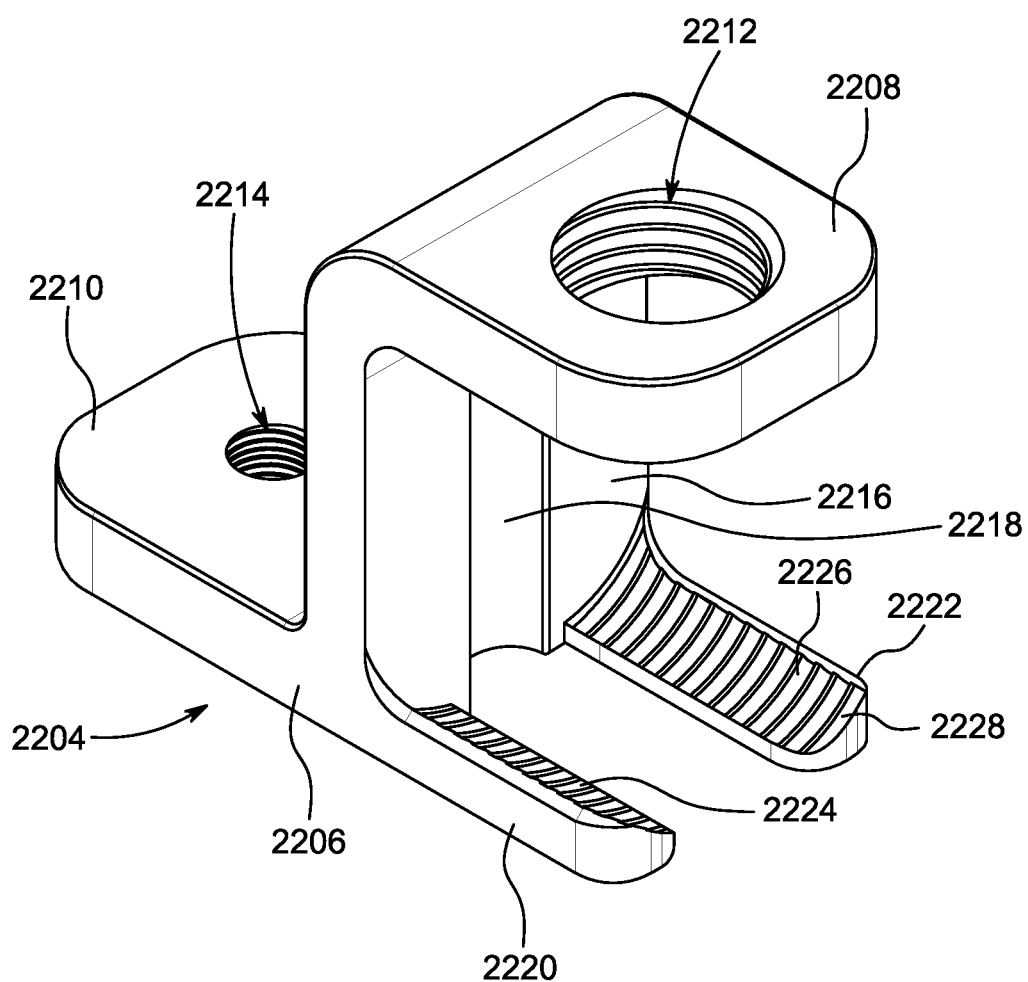
FIG. 29A is a perspective view of an illustrative embodiment of the one-piece side tulip connector.
Figure 29B:
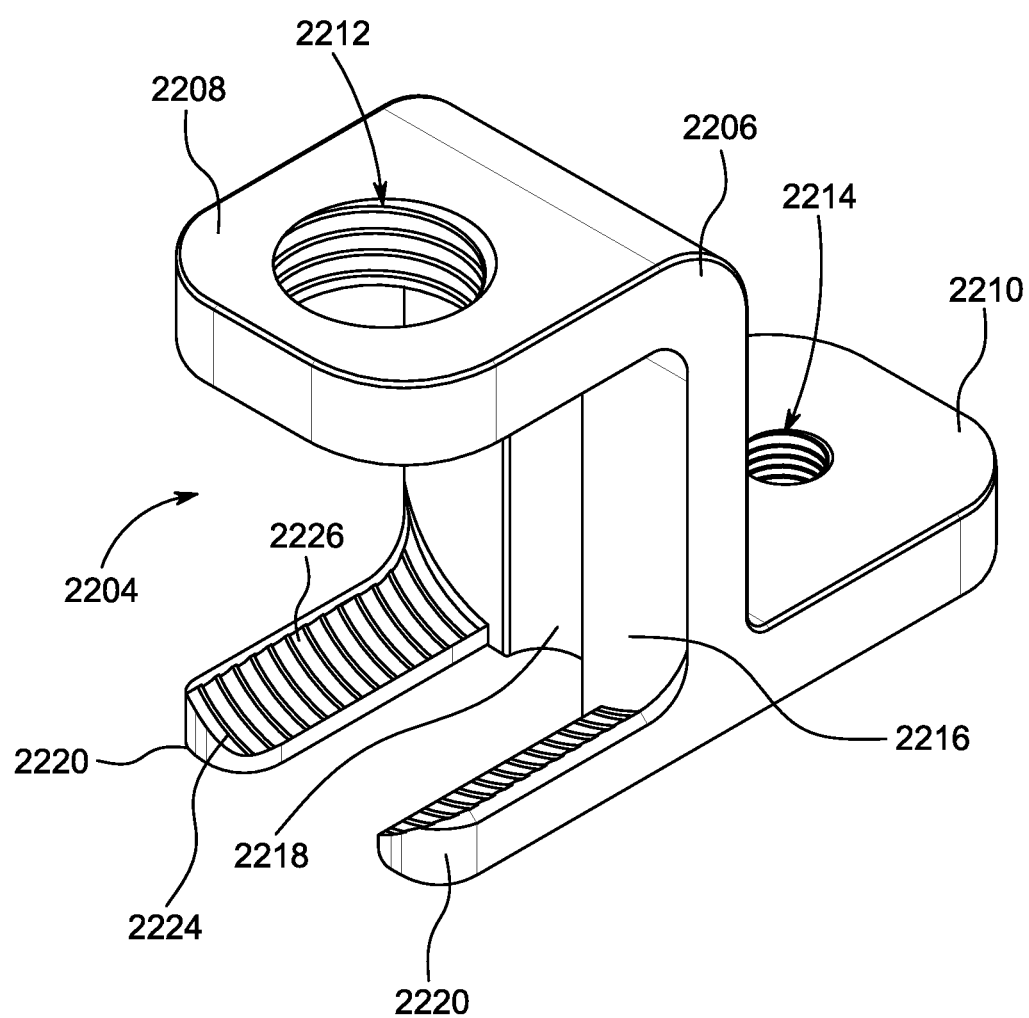
FIG. 29B is an alternative perspective view of the one-piece side tulip connector embodiment shown in FIG. 29A.
Figure 29C:
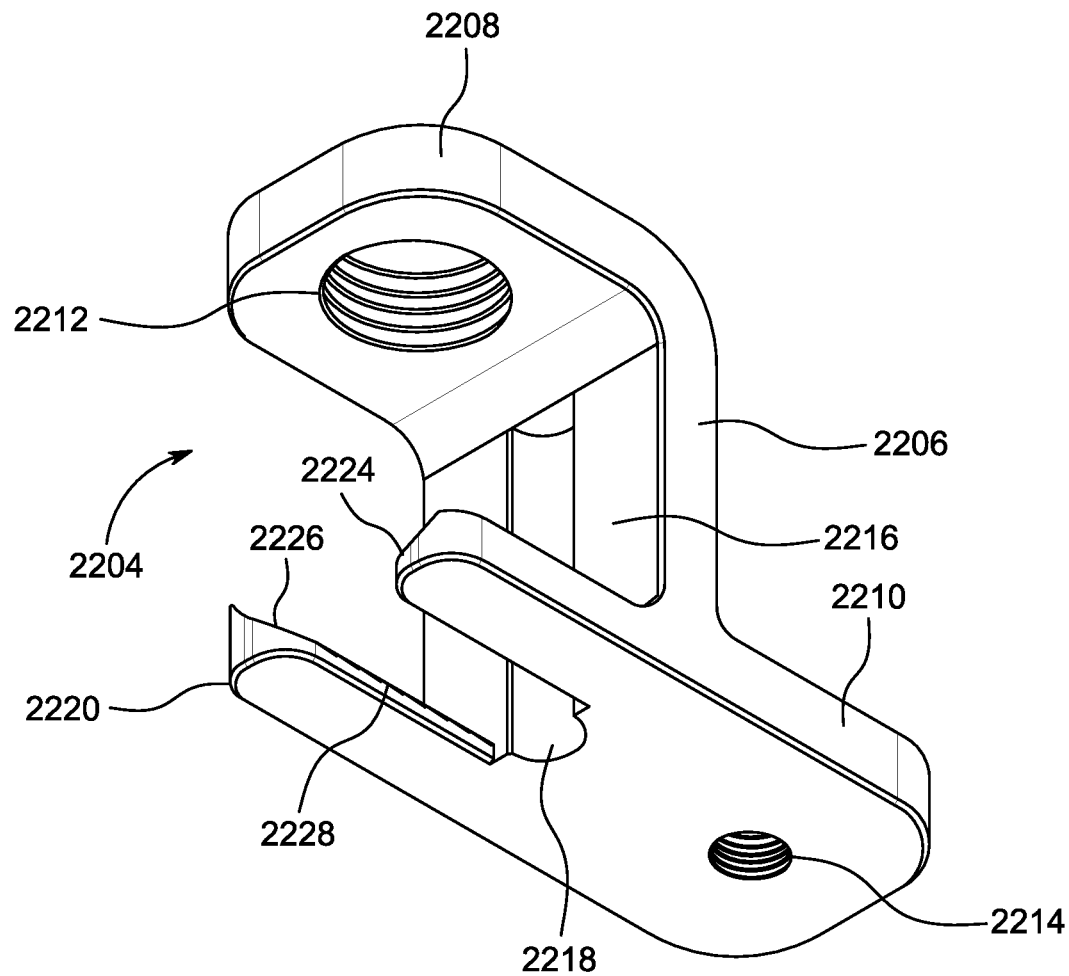
FIG. 29C is a bottom perspective view of the one-piece side tulip connector embodiment shown in FIG. 29A.
Figure 29D:
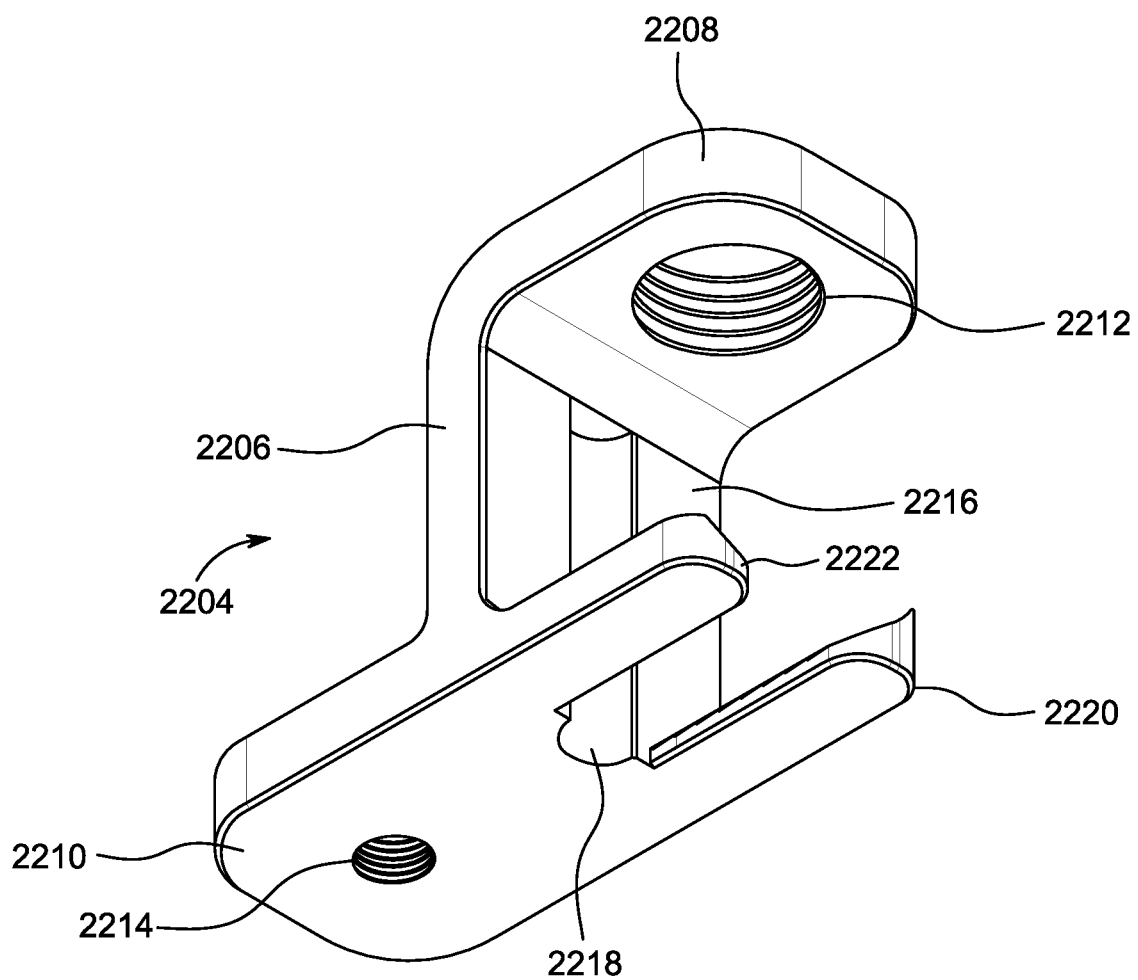
FIG. 29D is an alternative bottom perspective view of the one-piece side tulip connector embodiment shown in FIG. 29A.
Figure 29E:
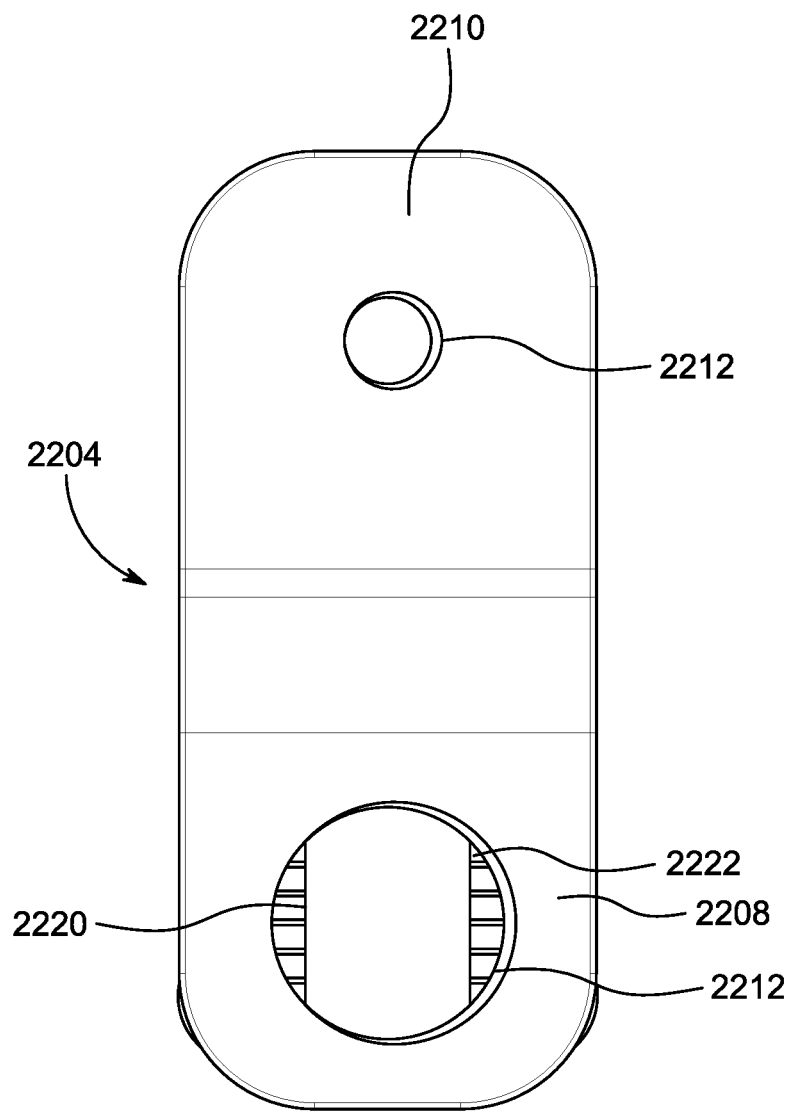
FIG. 29E is a top view of the one-piece side tulip connector embodiment shown in FIG. 29A.
Figure 29F:
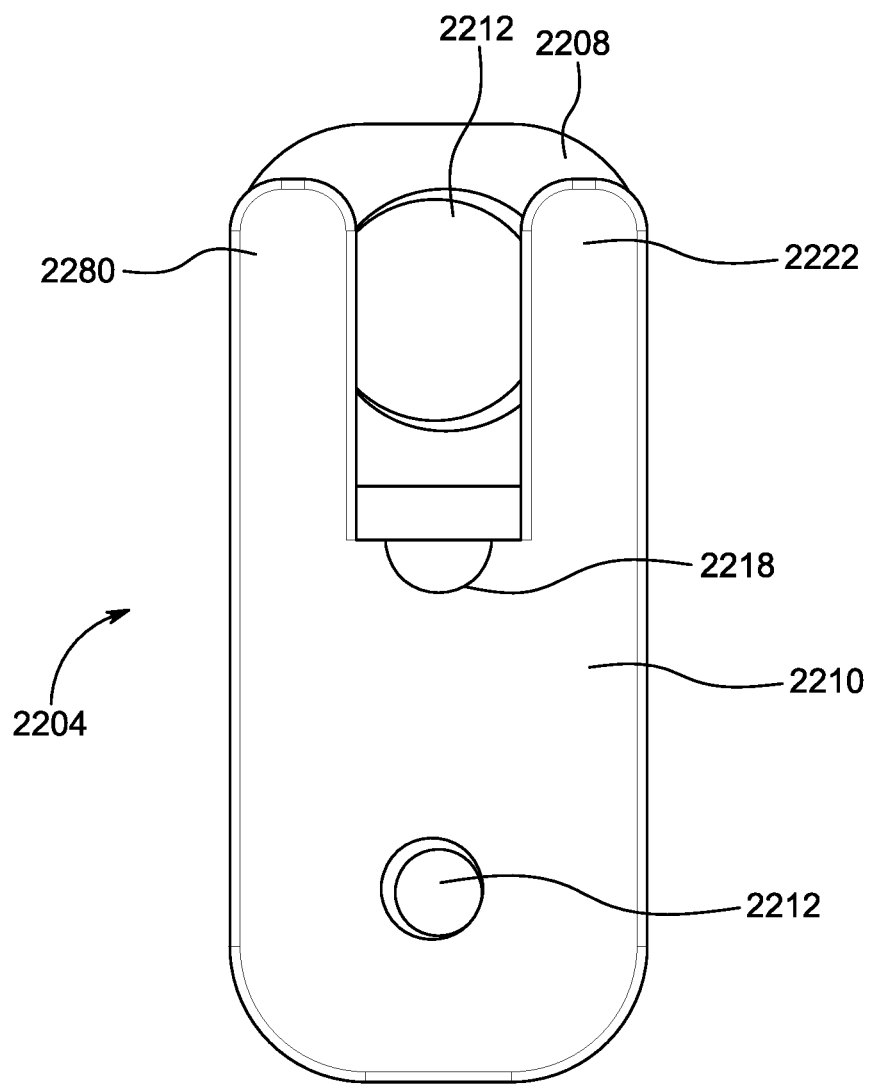
FIG. 29F is a bottom view of the one-piece side tulip connector embodiment shown in FIG. 29A.
Figure 29G:
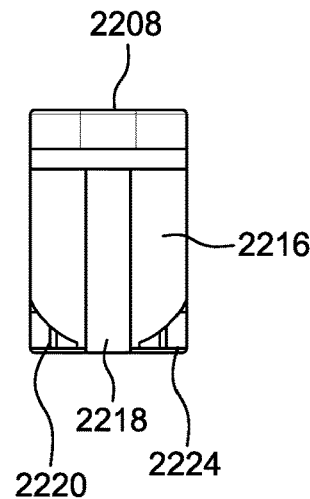
FIG. 29G is a front view of the one-piece side tulip connector embodiment shown in FIG. 29A.
Figure 29H:
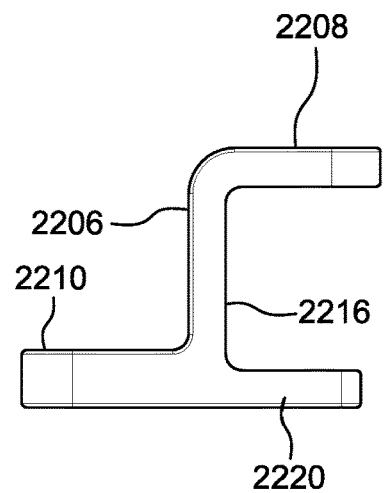
FIG. 29H is a right side of the one-piece side tulip connector embodiment shown in FIG. 29A.
Figure 29I:
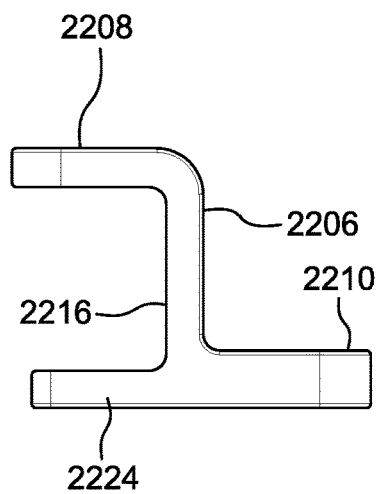
FIG. 29I is a left side of the one-piece side tulip connector embodiment shown in FIG. 29A.
Figure 30A:
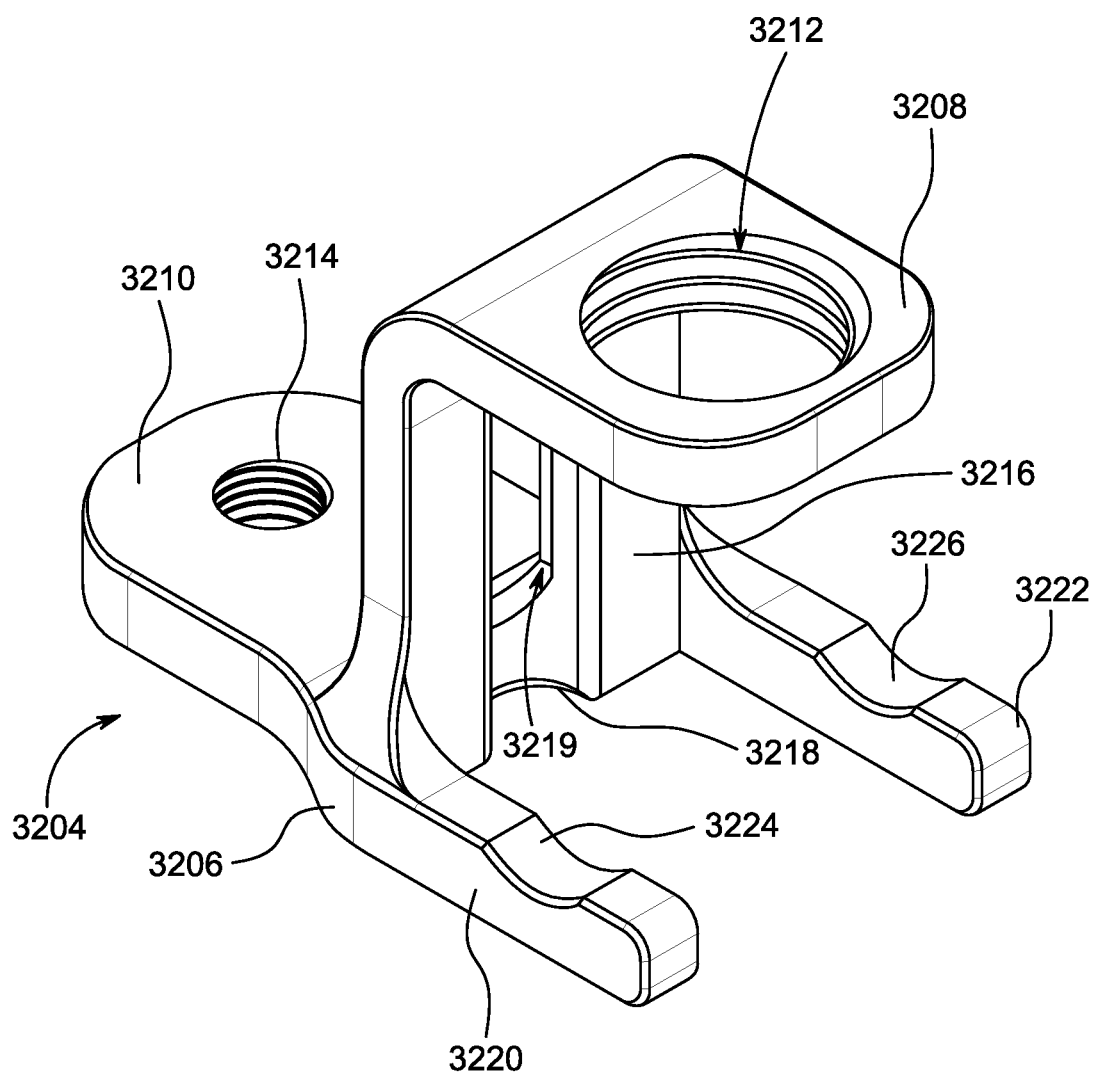
FIG. 30A is a perspective view of an illustrative embodiment of the one-piece side tulip connector.
Figure 30B:
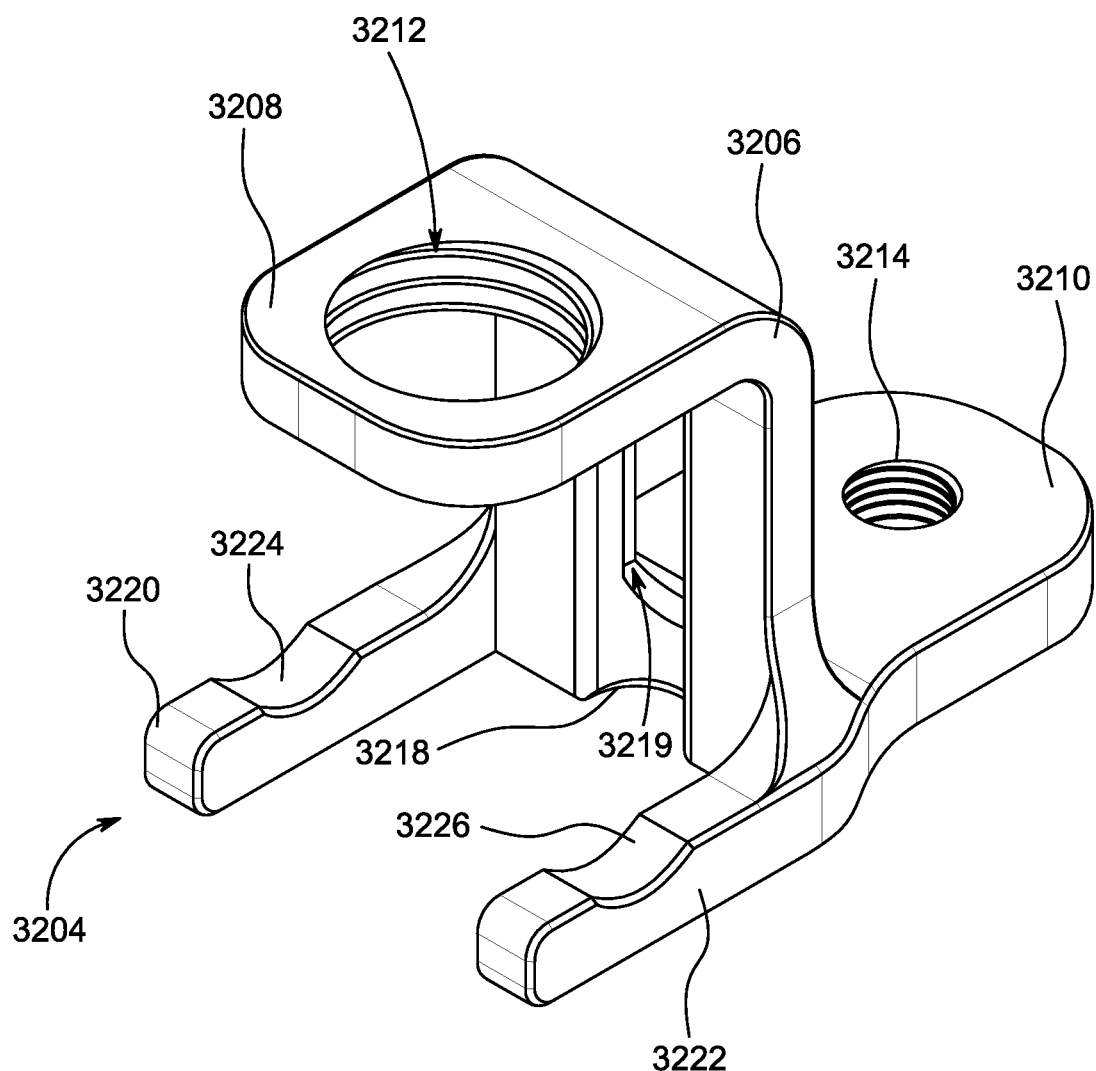
FIG. 30B is an alternative perspective view of the one-piece side tulip connector embodiment shown in FIG. 30A.
Figure 30C:
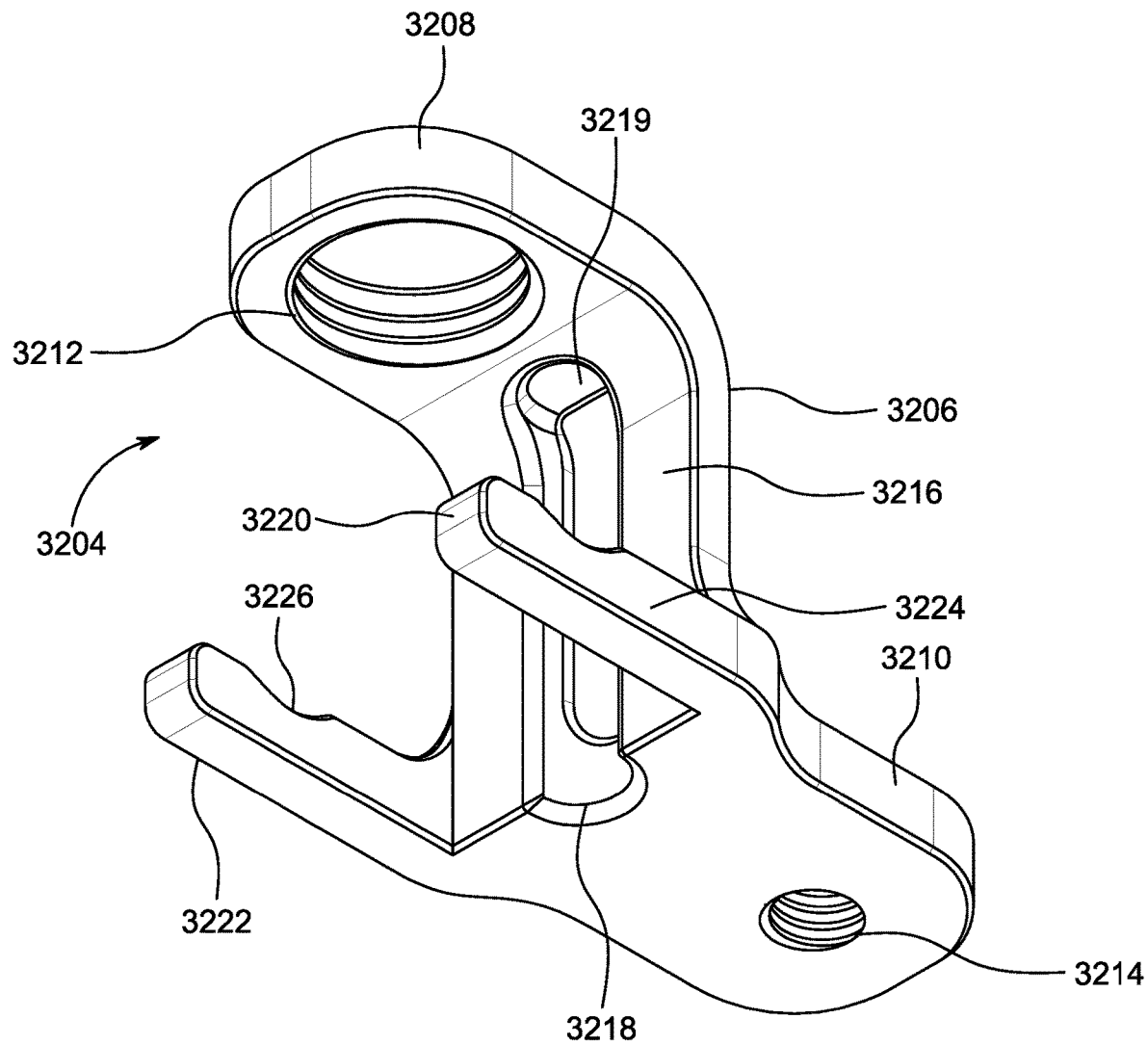
FIG. 30C is a bottom perspective view of the one-piece side tulip connector embodiment shown in FIG. 30A.
Figure 30D:
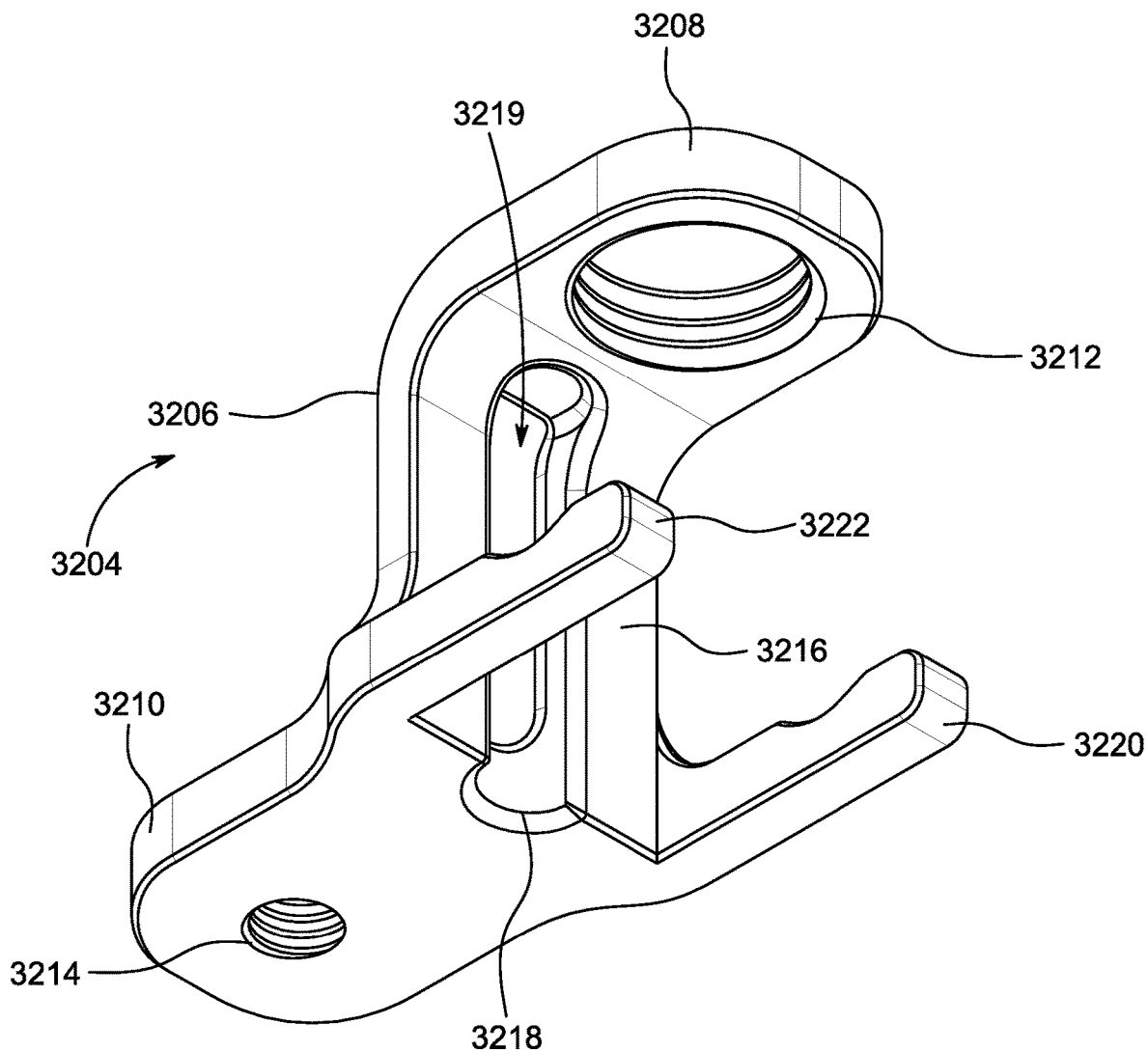
FIG. 30D is an alternative bottom perspective view of the one-piece side tulip connector embodiment shown in FIG. 30A.
Figure 30E:
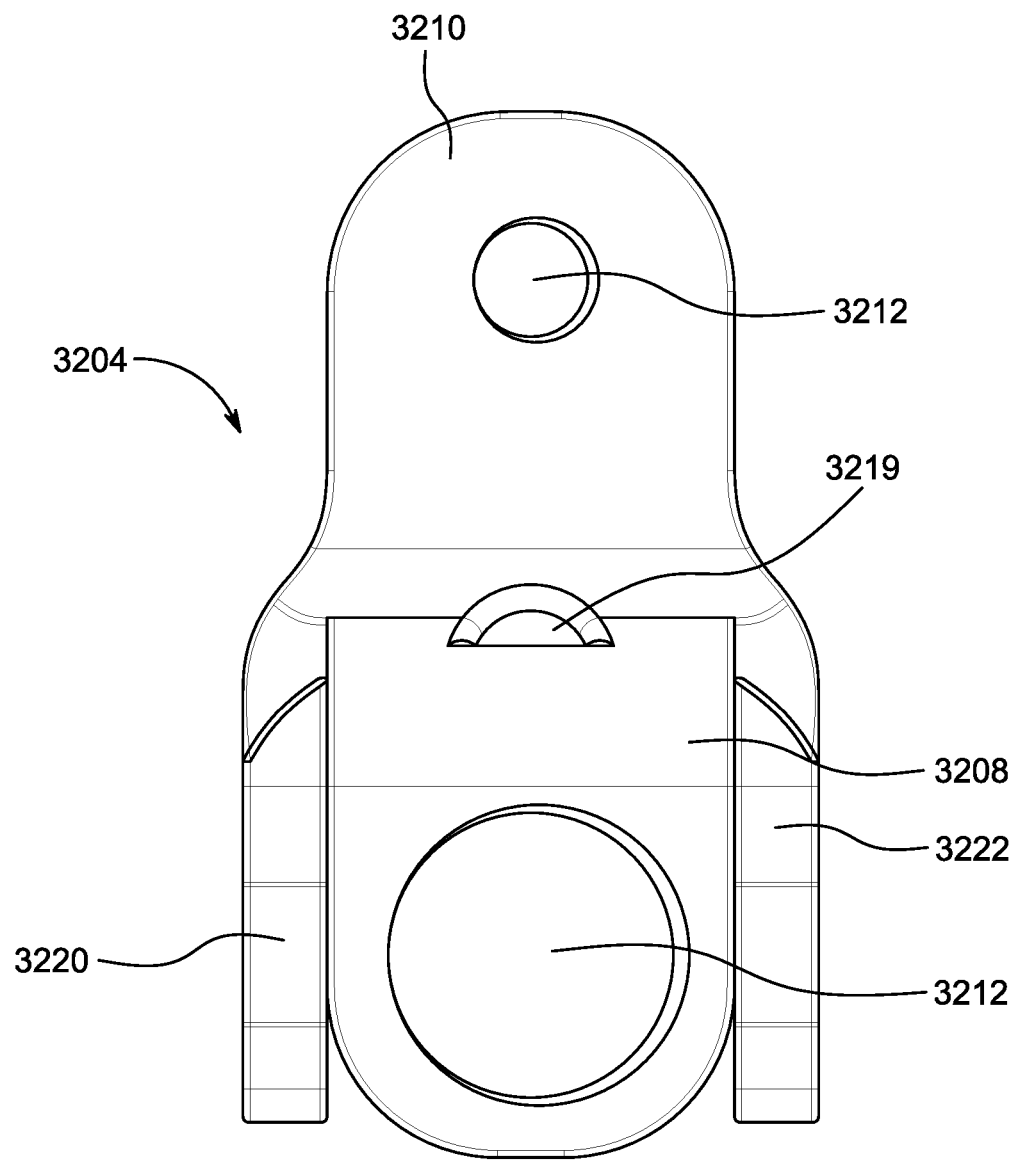
FIG. 30E is a top view of the one-piece side tulip connector embodiment shown in FIG. 30A.
Figure 30F:
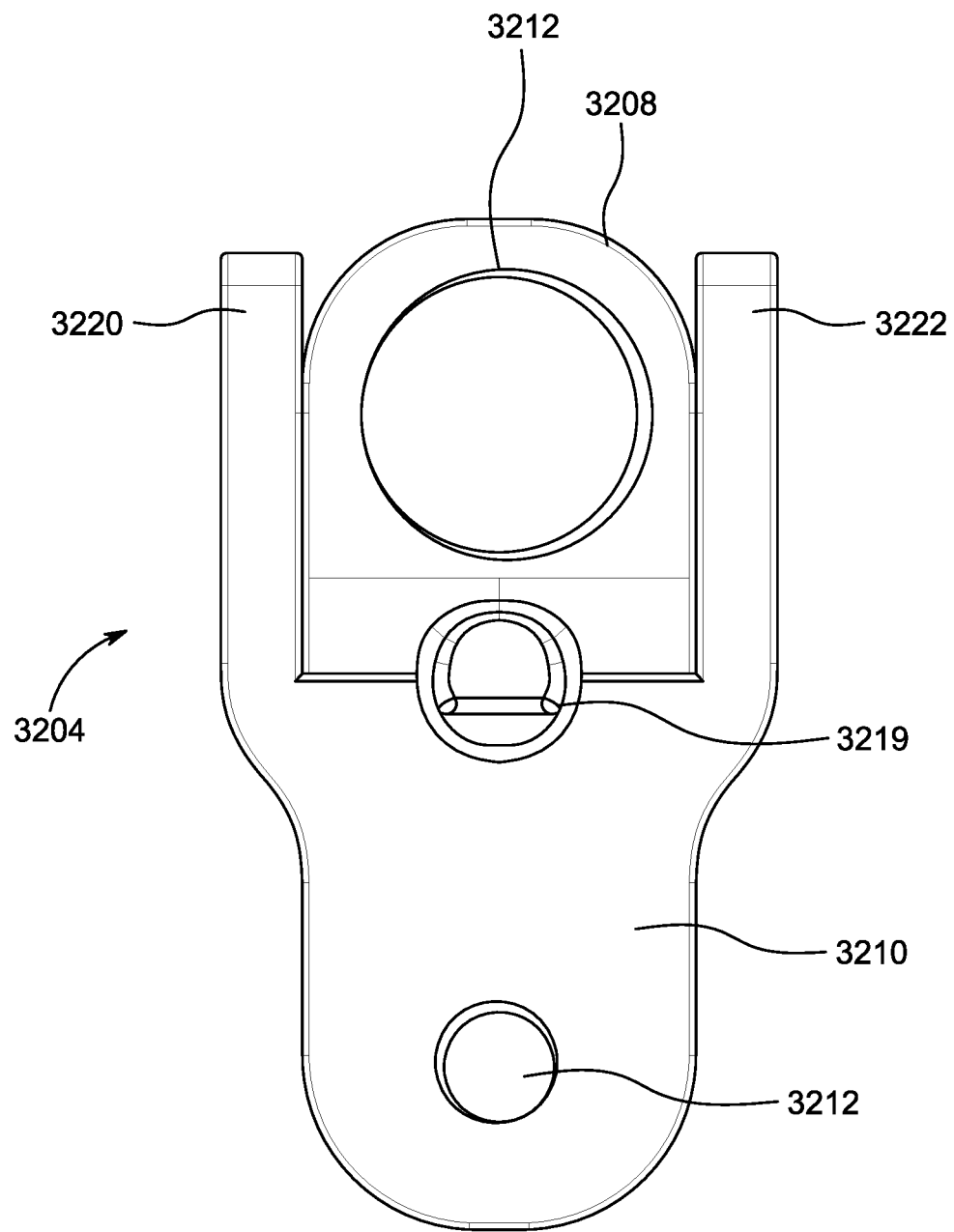
FIG. 30F is a bottom view of the one-piece side tulip connector embodiment shown in FIG. 30A.
Figure 30G:
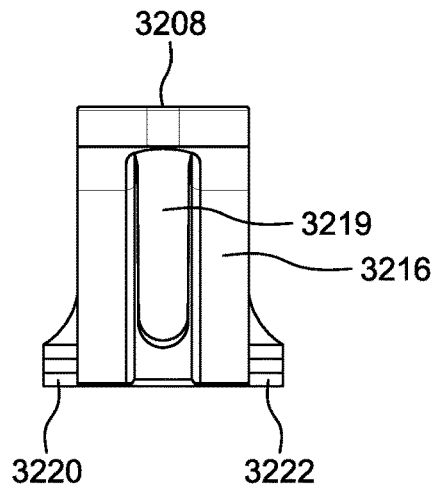
FIG. 30G is a front view of the one-piece side tulip connector embodiment shown in FIG. 30A.
Figure 30H:
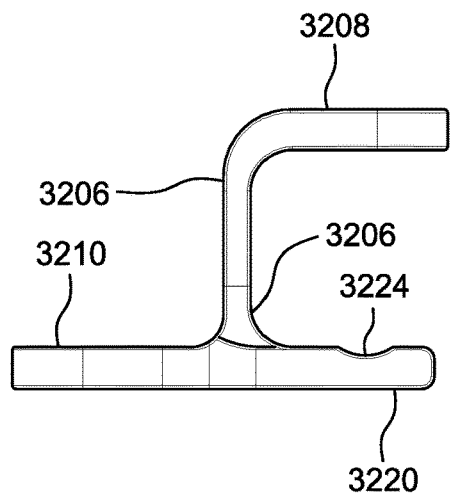
FIG. 30H is a right side of the one-piece side tulip connector embodiment shown in FIG. 30A.
Figure 30I:
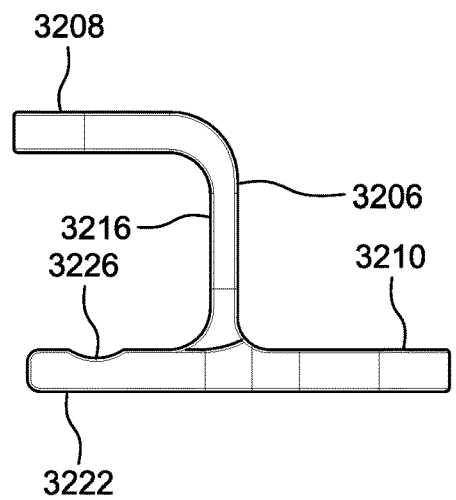
FIG. 30I is a left side of the one-piece side tulip connector embodiment shown in FIG. 30A.

Referring to FIGS. 26A and 27, an embodiment of the retractor blade 400 is shown. The retractor blade 400 may include a main body 402 having an inner surface 404 and an outer surface 406. The retractor blade main body 402 includes a first upper end 408, and an opposing, second or lower end 410. At or along the upper end, the retractor blade 400 may include a mounting structure 412 having a top opening 414 and side opening 416. The lower end 410 includes a connector engaging member 418, sized and shaped to fit within and secure to connector add on screw system connector, i.e., fitting into the add on screw system connector main body retractor blade receiving member 310, or similar structures. The connector engaging member 418 may have shoulders 420A and 420B and tab 420. When the tab 420 is inserted into the add on screw system connector main body retractor blade receiving member 310, shoulders 420A and 420B rest on the upper surface (i.e. 308 or 350) of the add on screw system connector 300. The retractor blade 400 may include a mechanism to allow for locking down to any of the add on screw system connectors 300. A threaded screw 409 with knob 411 (optionally), running the length of the body, from at or above the upper end 408m extending through the lower end 410 engages (via a turning knob 411) with the add on screw system connector 300 to lock in place, see FIG. 26B. Alternatively, the screw 409 may simply be turned using a key or screwdriver.

In use, generally, as an add-on surgical procedure to add additional surgical hardware, i.e., a surgical rod to existing implants, during exposure, the existing bone screw and rod at the surgical site will be exposed. The add on screw system connector 300 will be placed either around the rod or screw head, allowing the surgeon to attach a retractor plate or blade (such as retractor blade 400) to it for surgical exposure. During the surgery, the surgeon will then be able to distract off the add on screw system 100 to an adjacent bone screw at the level above and/or below that does not have a pre-existing screw and will be part of the new fusion site. Once the add on screw system connector 300 is attached to the pre-existing screw head and/or rod, a retractor blade (such as retractor blade 400) can be attached to aid in exposure. Once the exposure is performed, this attachment is removed. A tulip, polyaxial, or monoaxial, or any type of screw head or connector, will be inserted either attached directly to the pre-existing bone screw head and/or rod connection or with an add on screw system connector 300 attached to the pre-existing screw head or attached rod with a screw head attached to it, allowing connection to an adjacent vertebral screw by rod insertion above and/or below that vertebrae.

Referring to FIGS. 28A-30I, alternative embodiments of the one-piece side tulip connector are shown. The embodiments illustrated in these figures are similar to the one-piece side tulip connectors described above. The one-piece side tulip connectors illustrated in FIGS. 28A-30I can be adapted to include any one or more structures or components and/or structural configurations as described for the one-piece side tulip connector previously, but not shown in the alternative embodiments. In all cases, the alternative embodiments of the one-piece side tulip connector provide for a tulip head attachment with a side mount add-on tulip head.

Referring to FIGS. 28A-28I, the one-piece side tulip connector 1204 comprises a main body 1206 having a preexisting pedicle screw engagement member 1208 and a secondary tulip engaging member 1210. The one-piece side tulip connector 1204 is configured to fit on an existing tulip head with a flat bottom, fixed with a top set screw via threaded opening 1212. The one-piece side tulip connector 1204 includes a place on the side to mount an add-on tulip head (or secondary tulip) or other accessories via threaded opening 1214. A main body wall 1216 may include a curved portion 1218 sized and shaped to engage with a portion of the screw 14 or tulip 20. Arms 1220 and 1222 may include generally flat or planar surfaces 1224 and 1226. The one-piece side tulip connector 1204 may be designed to engage with a pre-existing rod in the same manner as, using the same structures, as described for the one-piece side tulip connector 204. While the add-on tulip head (or secondary tulip) via screws in opening 1214, alternative embodiments may include the secondary add-on tulip head (or secondary tulip) being pre-pre-attached (pre-assembled) or secured via other means, such as welding.

Referring to FIGS. 29A-29I, the one-piece side tulip connector 2204 comprises a main body 2206 having a preexisting pedicle screw engagement member 2208 and a secondary tulip engaging member 2210. The one-piece side tulip connector 2204 is configured to fit on an existing tulip head with a curved bottom, fixed with a top set screw via threaded opening 2212. The one-piece side tulip connector 2204 includes a place on the side to mount an add-on tulip head or other accessories via threaded opening 2214. A main body wall 1216 may include a curved portion 2218 sized and shaped to engage with a portion of the screw 14. Arms 2220 and 2222 may include curved and/or angled surfaces 2224 and 2226 (correspond to the curvature of the tulip head). Arms 2220 and 2222 may include a knurled surface 2228 for use in gripping. The one-piece side tulip connector 2204 may be designed to engage with a pre-existing rod in the same manner as, using the same structures, as described for the one-piece side tulip connector 204. While the add-on tulip head (or secondary tulip) via screws in opening 2214, alternative embodiments may include the secondary add-on tulip head (or secondary tulip) being pre-attached (pre-assembled) or secured via other means, such as welding Referring to FIGS. 30A-30I, the one-piece side tulip connector 3204 comprises a main body 3206 having a preexisting pedicle screw engagement member 3208 and a secondary tulip engaging member 3210. The main body is shown with a preexisting pedicle screw engagement member 3208 having a different size (larger than) the secondary tulip engaging member 3210. The one-piece side tulip connector 3204 is configured to fit to a rod having an existing tulip head, fixed with a top set screw via threaded opening 3212. The one-piece side tulip connector 3204 includes a place on the side to mount an add-on tulip head or other accessories via threaded opening 3214. A main body wall 3216 may include a curved portion 3218 sized and shaped to engage with a portion of the screw 14 or tulip 20. The main body wall 3216 also includes an opening or cut-out section 3219. Arms 3220 and 3222 may include a rod engaging portion 3224 and 3226, illustrated herein as a curved section (correspond to the curvature of the tulip head). While the add-on tulip head (or secondary tulip) via screws in opening 3214, alternative embodiments may include the secondary add-on tulip head (or secondary tulip) being pre-attached (pre-assembled) or secured via other means, such as welding.

Figure 31A:
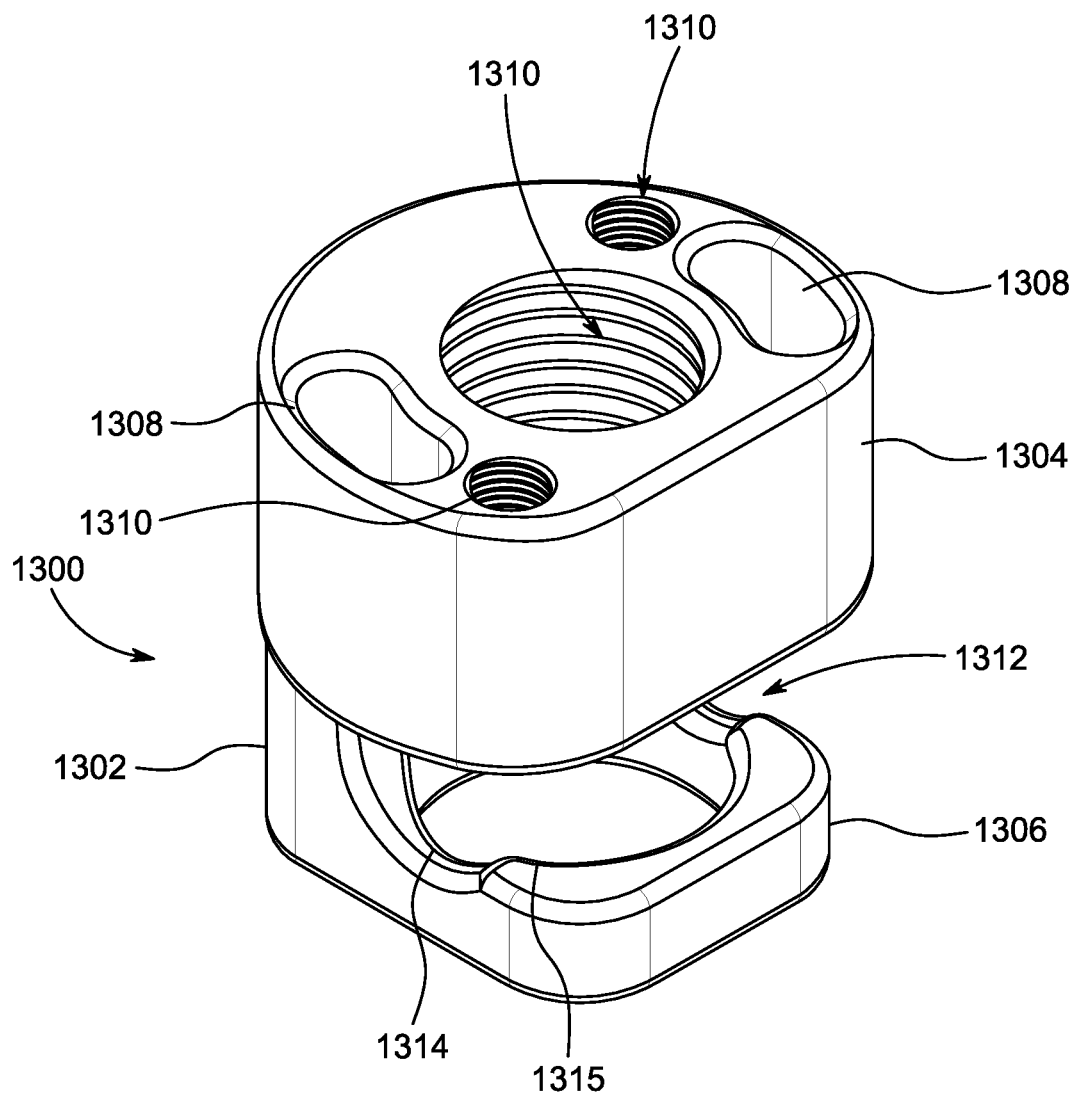
FIG. 31A is a perspective view of an illustrative embodiment of a rod fit blade connector.
Figure 31B:
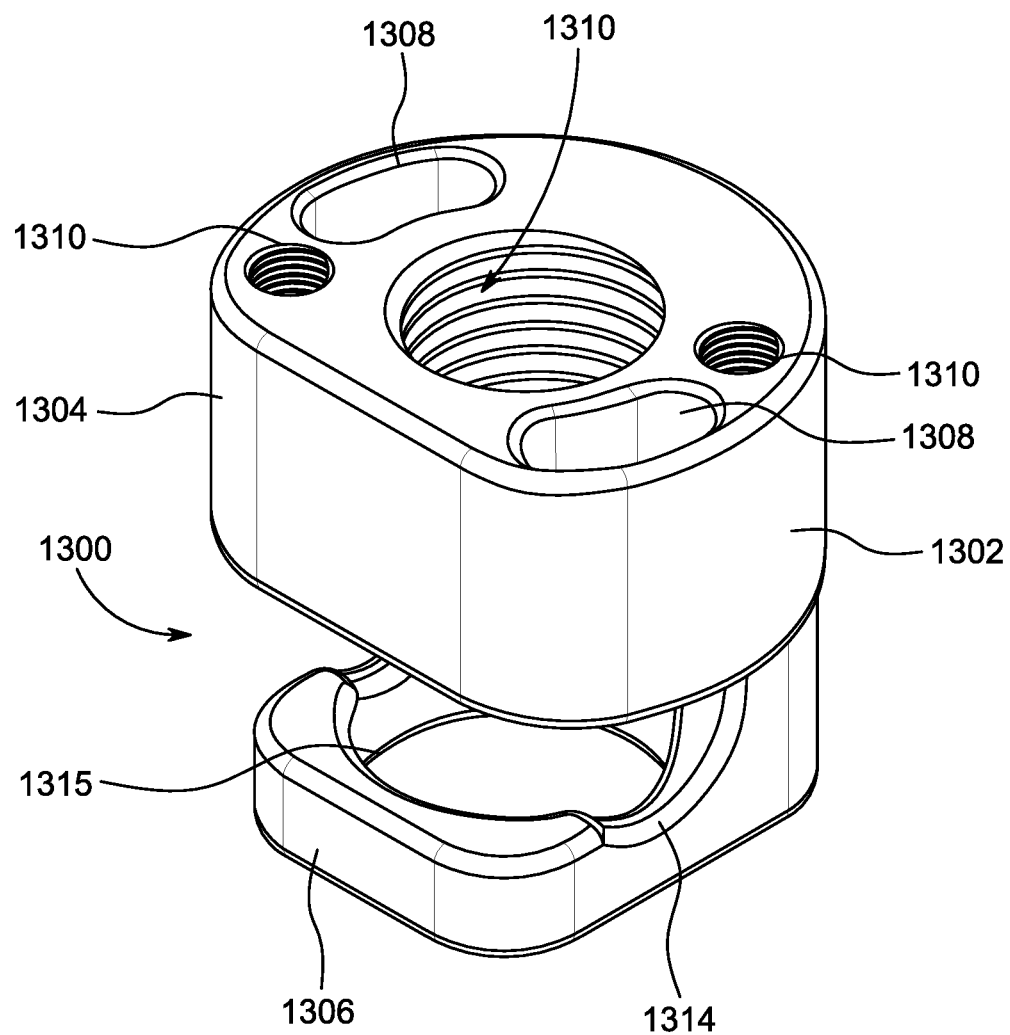
FIG. 31B is an alternative perspective view of the rod fit blade connector shown in FIG. 31A.
Figure 31C:
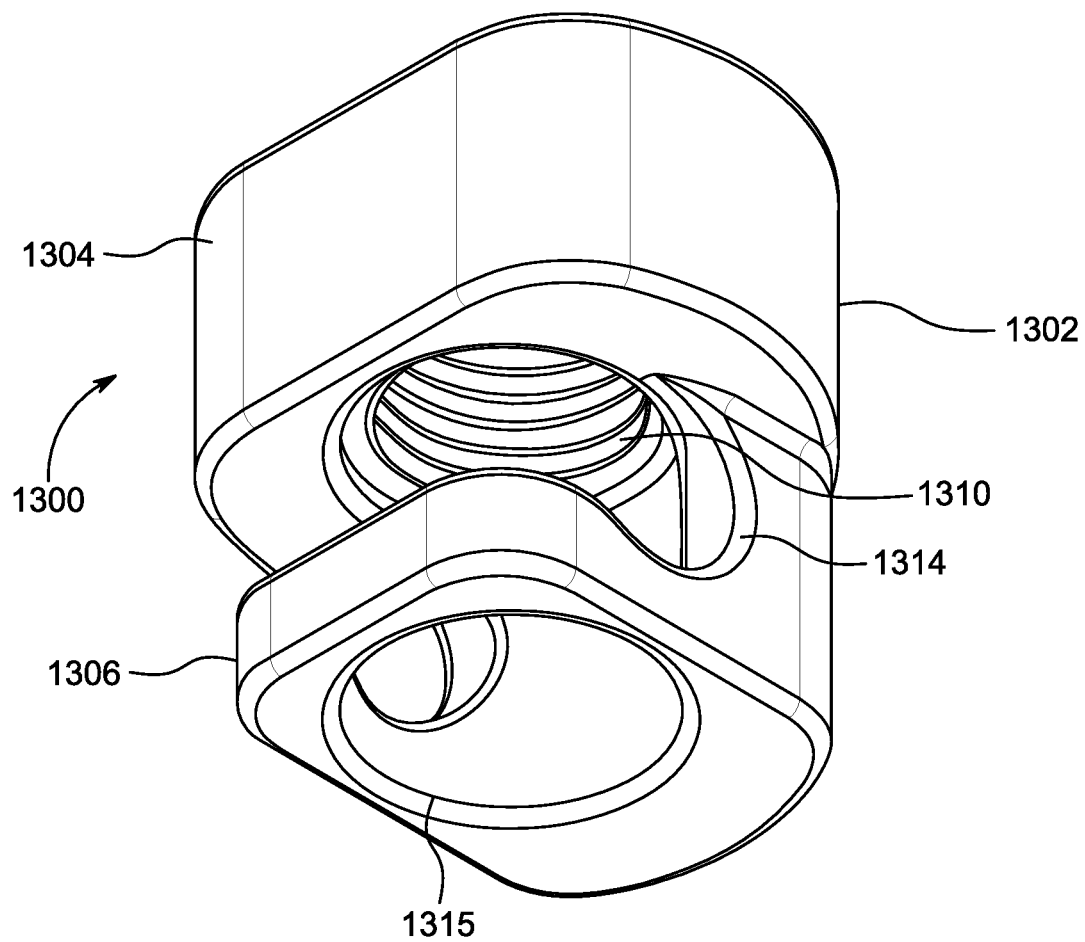
FIG. 31C is a bottom perspective view of the rod fit blade connector shown in FIG. 31A.
Figure 31D:
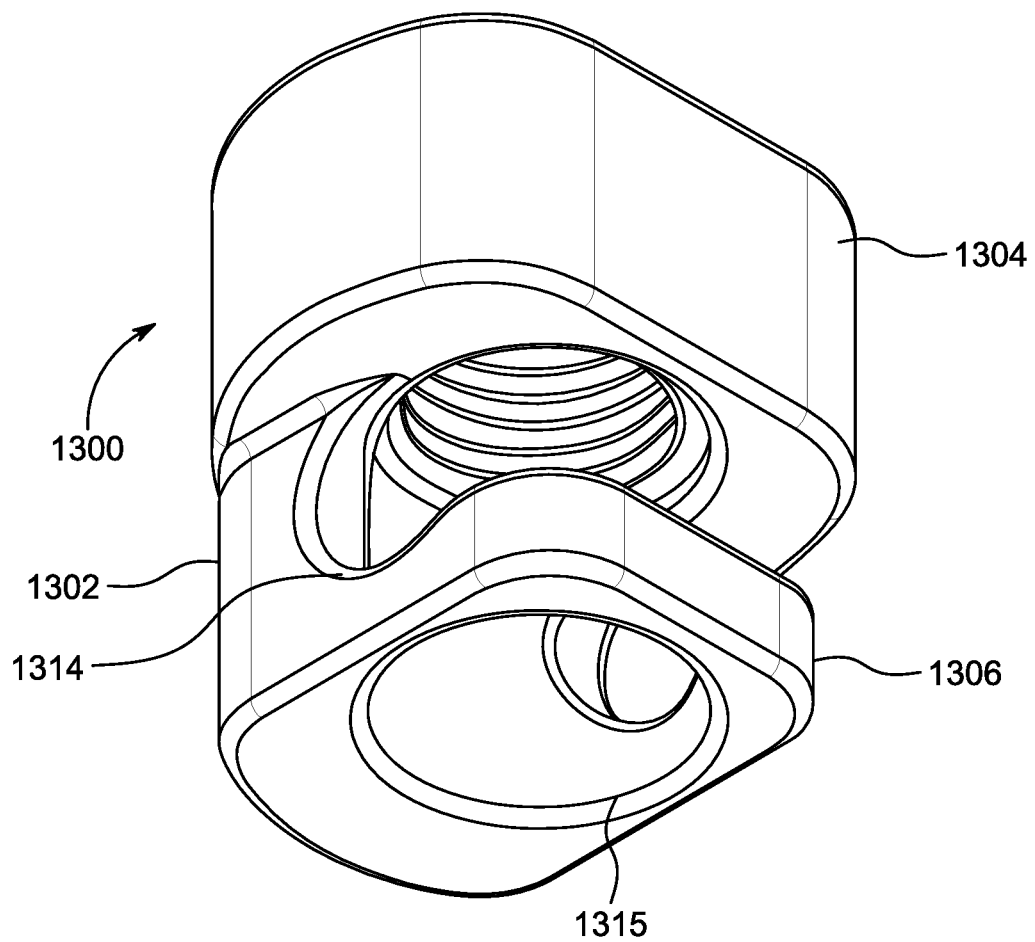
FIG. 31D is an alternative bottom perspective view of the rod fit blade connector shown in FIG. 31A.
Figure 31E:
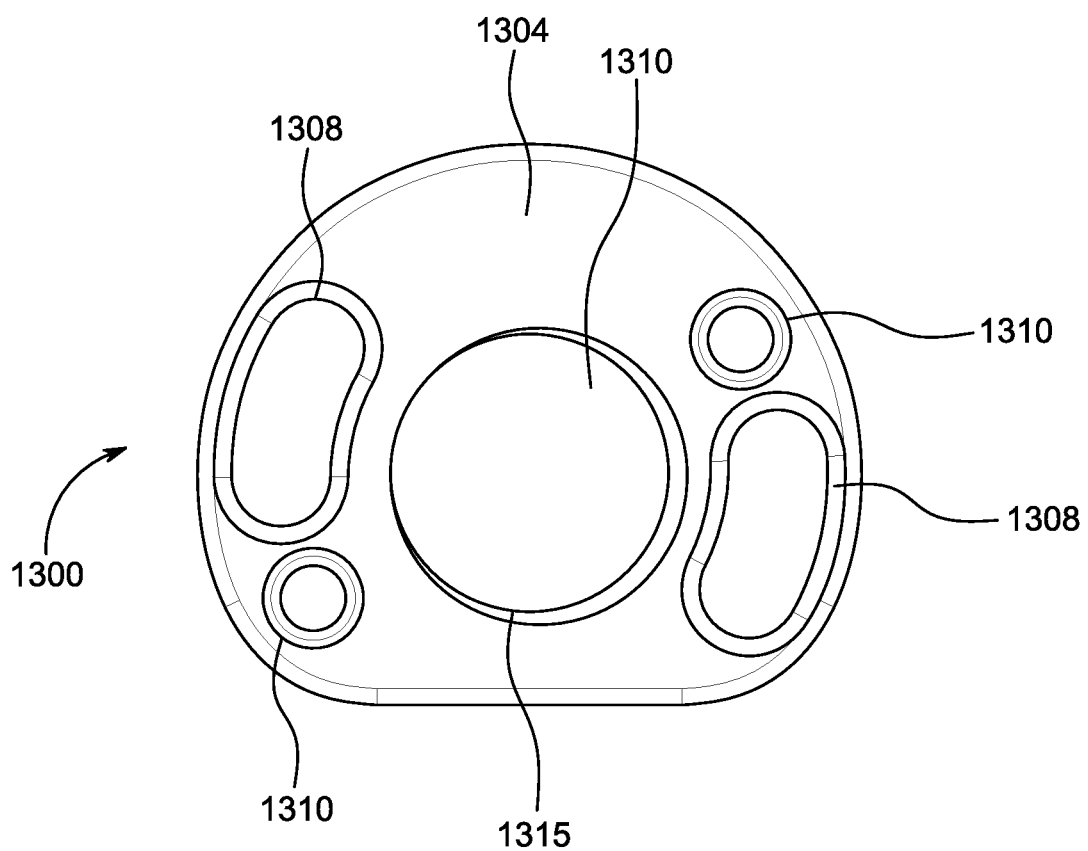
FIG. 31E is a top view of the rod fit blade connector shown in FIG. 31A.
Figure 31F:
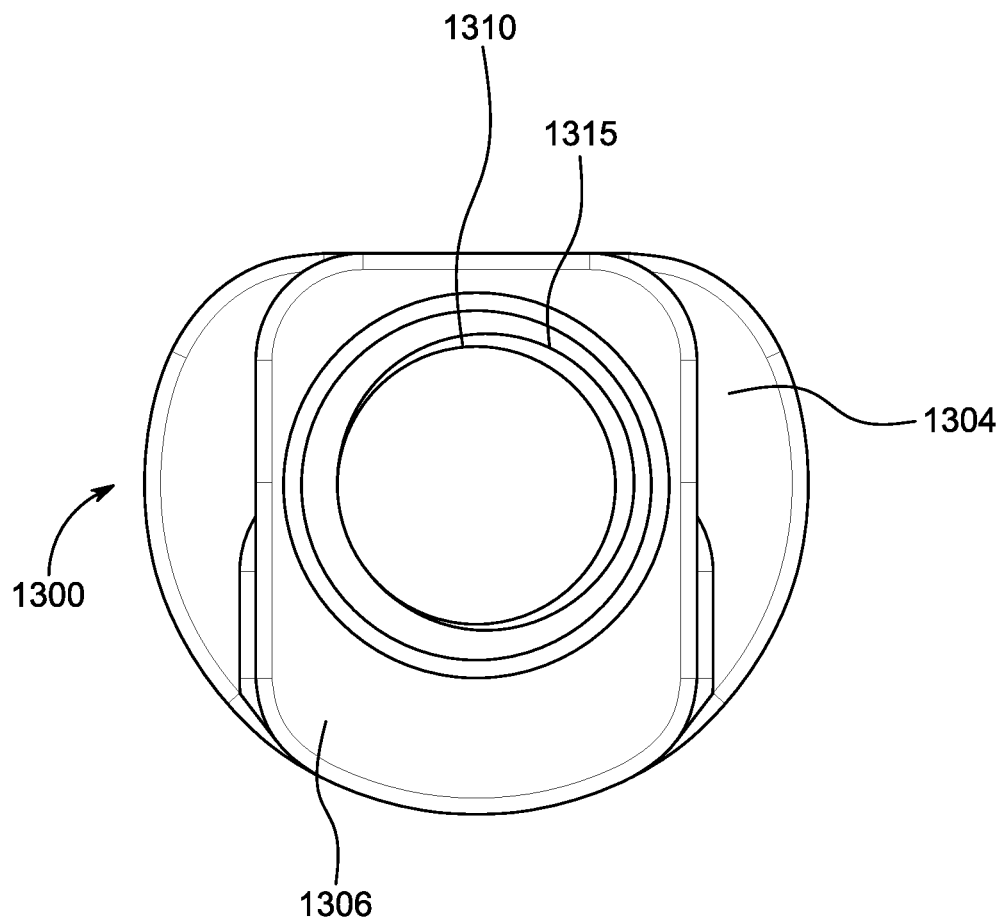
FIG. 31F is a bottom view of the rod fit blade connector shown in FIG. 31A.
Figure 31G:
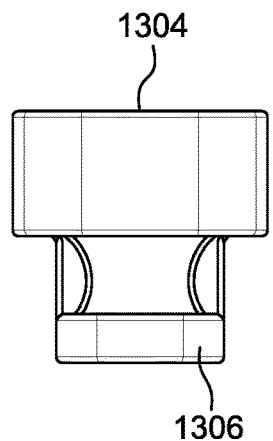
FIG. 31G is a front view of the rod fit blade connector shown in FIG. 31A.
Figure 31H:
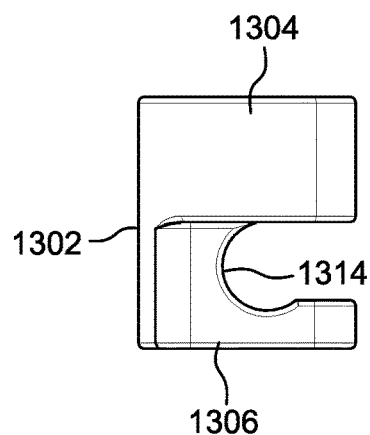
FIG. 31H is a right side of the rod fit blade connector shown in FIG. 31A.
Figure 31I:
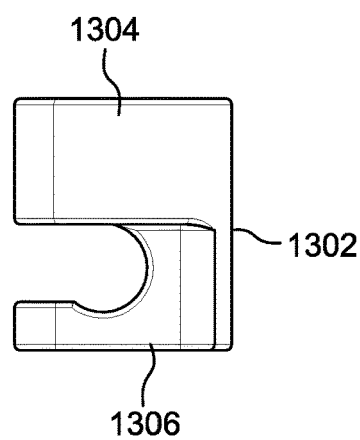
FIG. 31I is a left side of the rod fit blade connector shown in FIG. 31A.
Figure 32A:
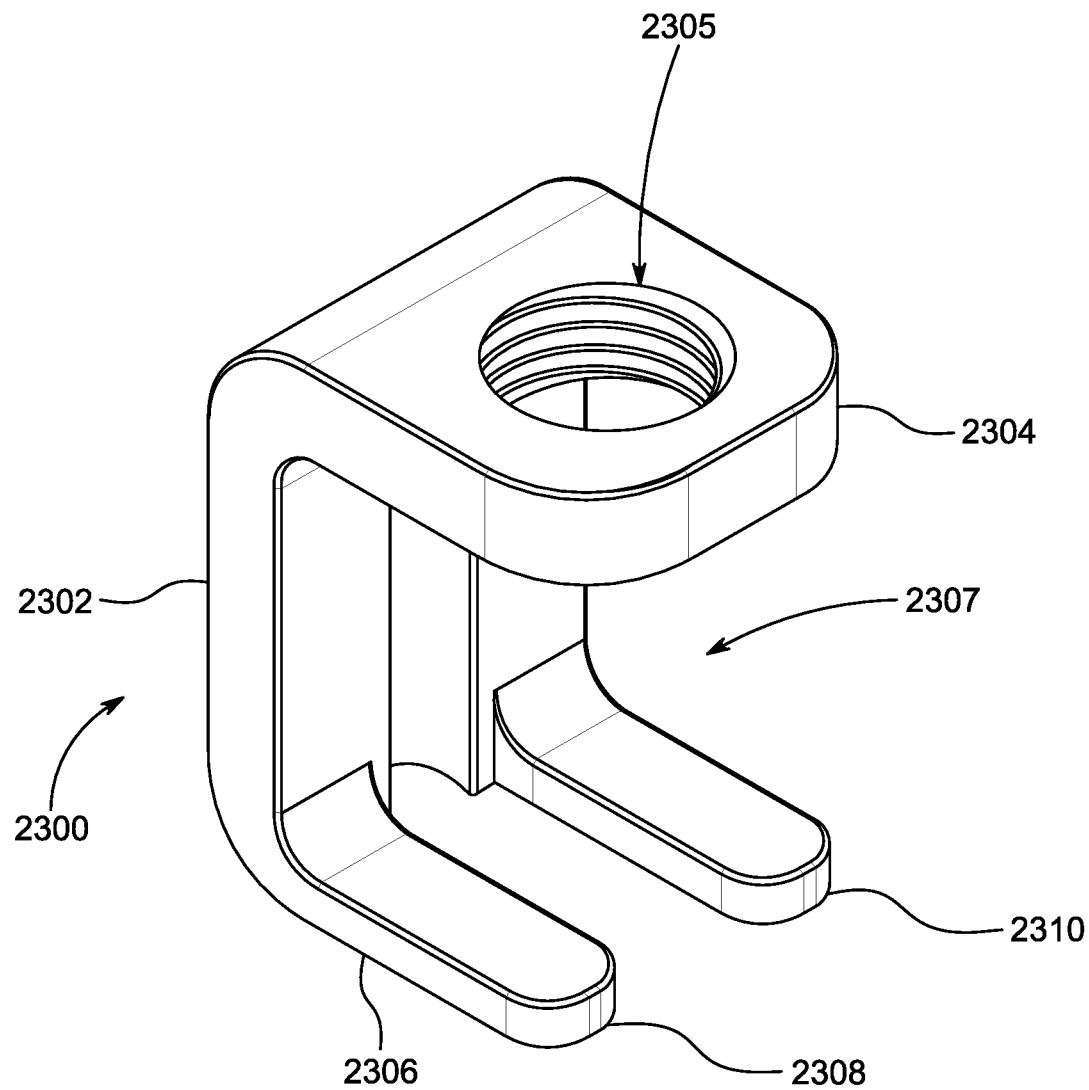
FIG. 32A is a perspective view of an illustrative embodiment of a tulip head attachment connector.
Figure 32B:
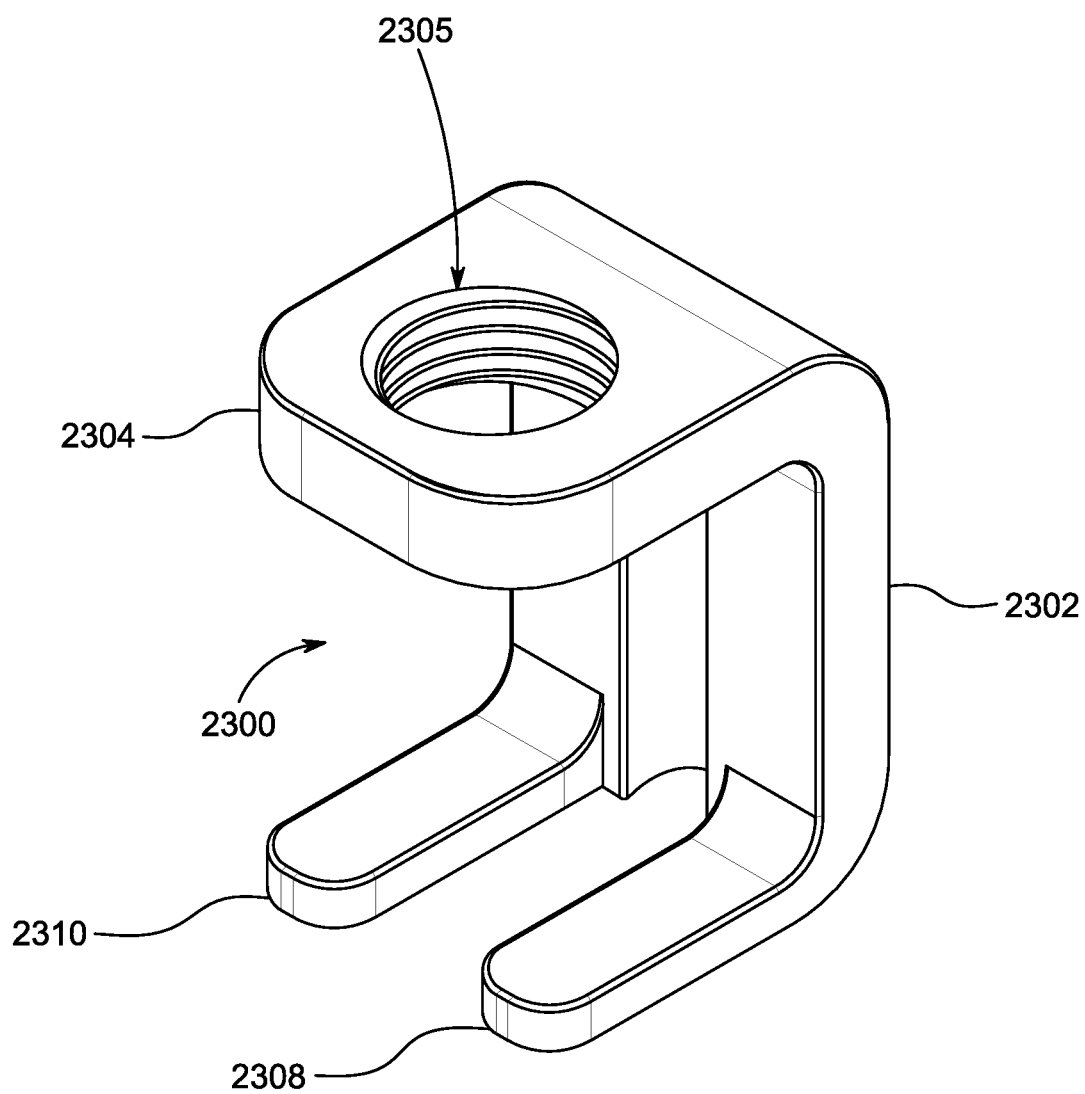
FIG. 32B is an alternative perspective view of the tulip head connector shown in FIG. 32A.
Figure 32C:
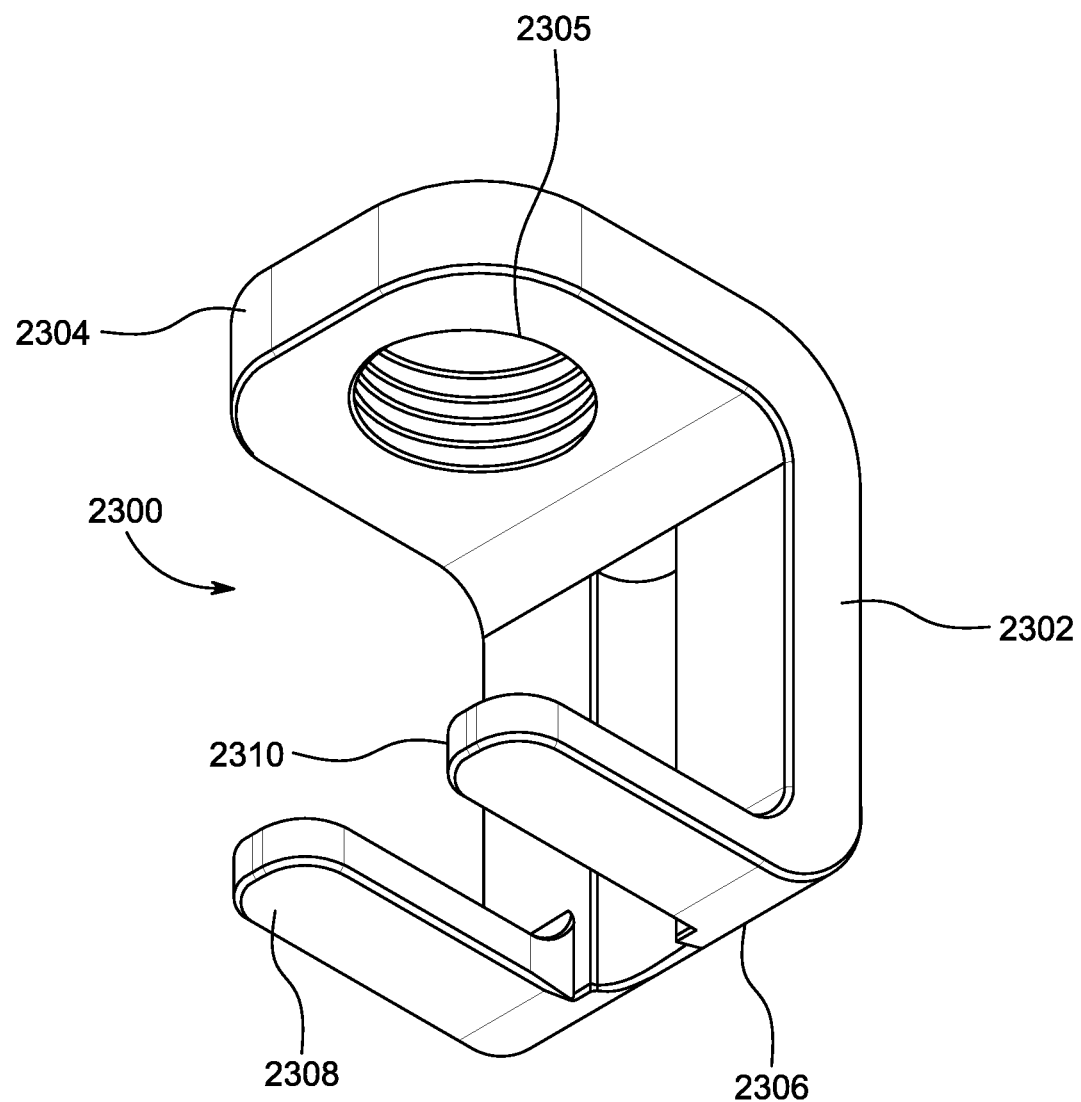
FIG. 32C is a bottom perspective view of the tulip head connector shown in FIG. 32A.
Figure 32D:
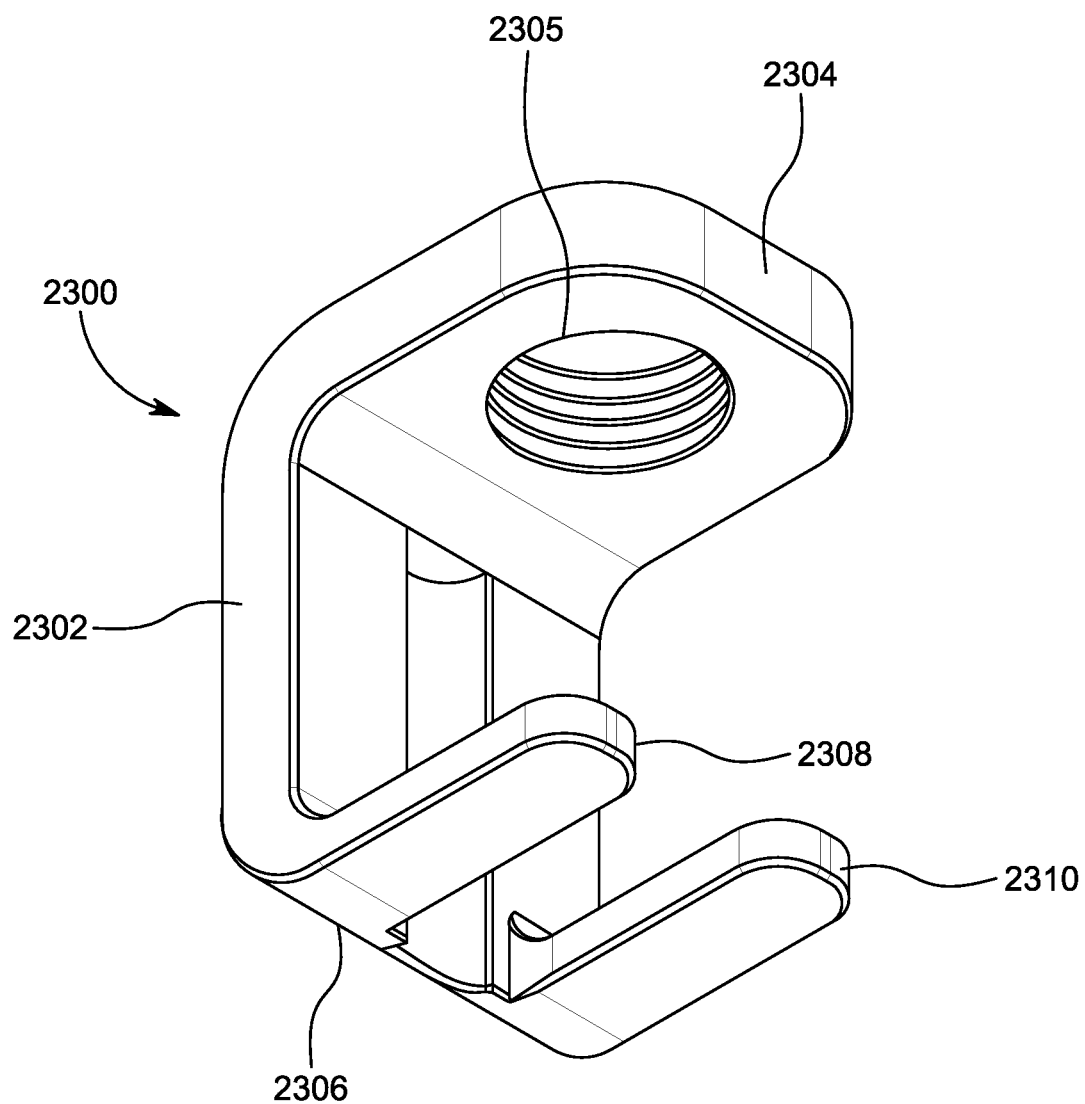
FIG. 32D is an alternative bottom perspective view of the tulip head connector shown in FIG. 32A.
Figure 32E:
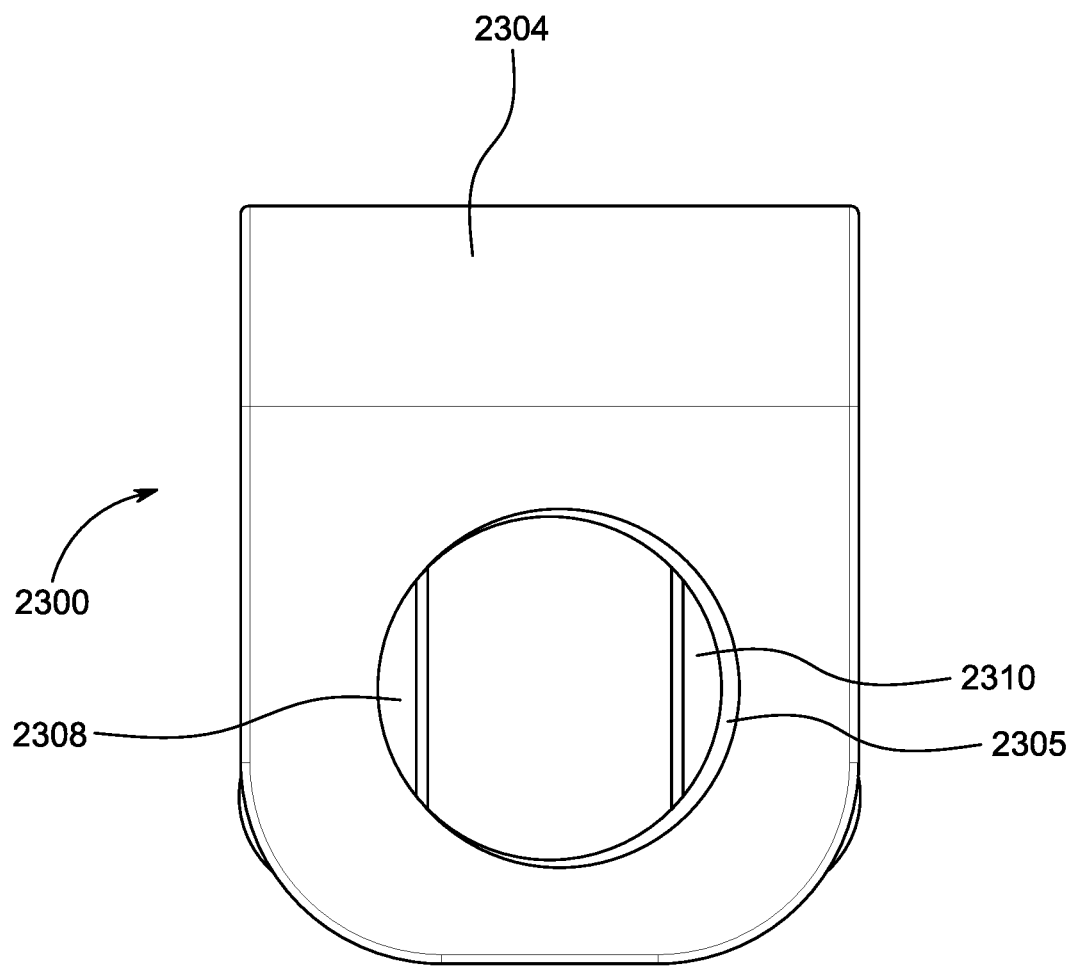
FIG. 32E is a top view of the tulip head connector shown in FIG. 32A.
Figure 32F:
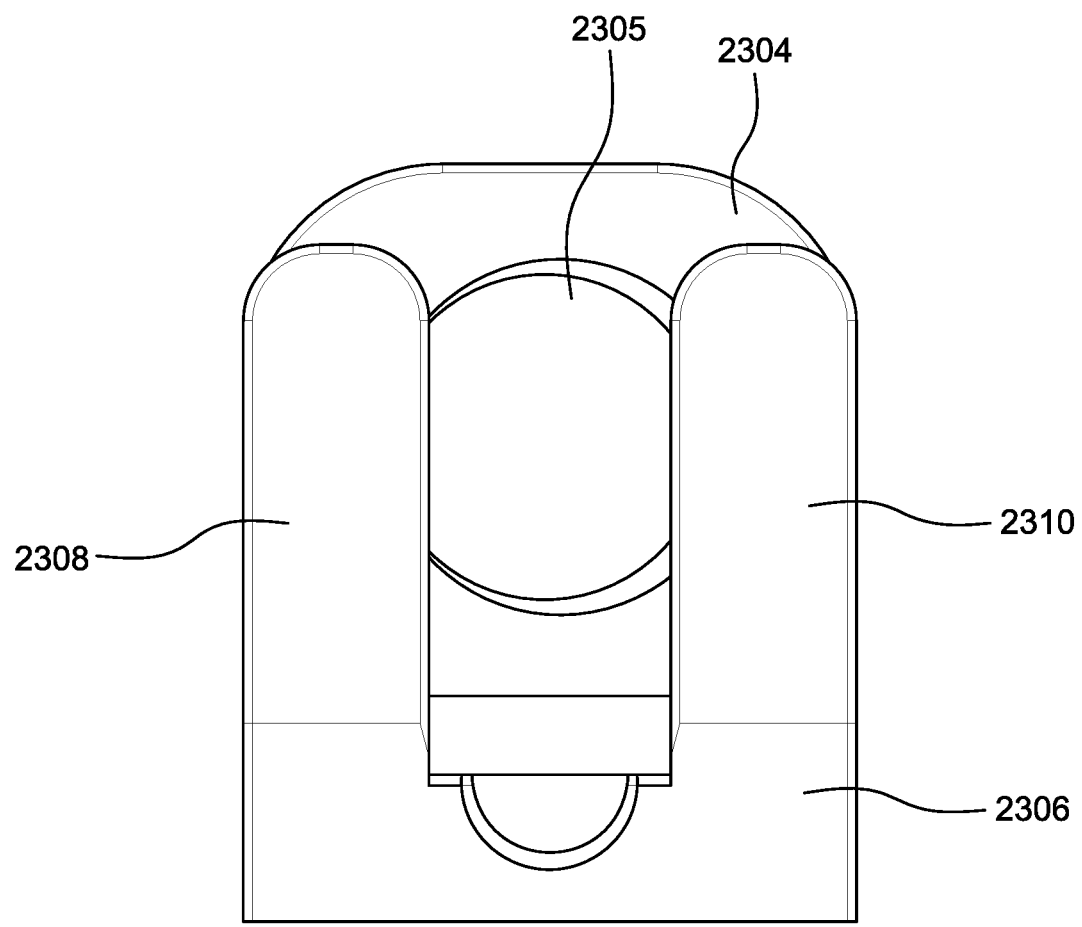
FIG. 32F is a bottom view of the tulip head connector shown in FIG. 32A.
Figure 32G:
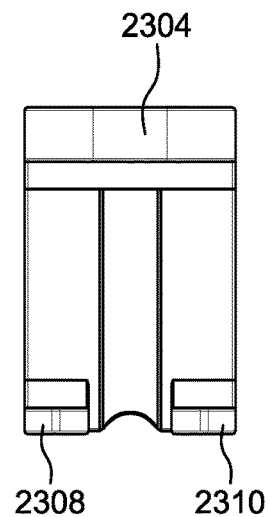
FIG. 32G is a front view of the tulip head connector shown in FIG. 32A.
Figure 32H:
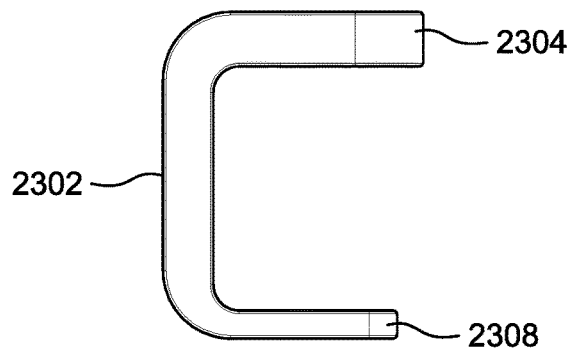
FIG. 32H is a right side of the tulip head connector in FIG. 32A.
Figure 32I:
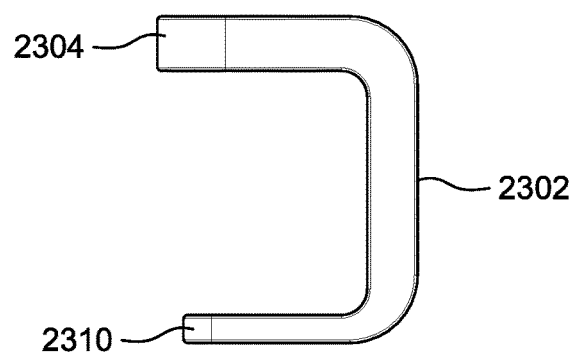
FIG. 32I is a left side of the tulip head connector shown in FIG. 32A.

Referring to FIGS. 31A-38I, alternative embodiments of the screw and/or rod connectors are shown. The embodiments illustrated in these figures are similar to the screw and/or rod connectors 300 described above. The screw and/or rod connectors illustrated in FIGS. 31A-38I can be adapted to include any one or more structures or components and/or structural configurations described for the screw and/or rod connectors 300s but not shown in the alternative embodiments. Referring to FIGS. 31A-31, the rod connector 1300 is configured to engage with and secure to a previously implanted rod 22. The rod connector 1300 may comprise a main body 1302 having an upper portion 1304 configured to engage with pedicle screw set screw and retractor blade (via retractor openings 1308 and threaded screw openings 1310), and a lower portion 1306 configured to engage with a preexisting surgical device, such as a previously implanted rod 22 (space or channel 1312 and curved surface 1314). The lower portion 1306 includes opening 1315. While two retractor openings 1308 are shown, one or three or four may be used, thus allowing retractor connection in any direction, i.e. front, back, left side, or right side of the rod connector 1300.

Referring to FIGS. 32A-32I, the rod connector 3300 is configured to engage with and secure to a previously implanted rod 22. The tulip head connector 2300 is configured to connect to a tulip head having a flat surface. The tulip head connector 2300 may comprise a main body 2302 having an upper portion 2304 configured to engage with pedicle screw set screw (threaded opening 2305) and/or a retractor blade, and a lower portion 2306 configured to engage with a preexisting surgical device, such as a previously implanted pedicle screw tulip 20. The add tulip head connector 2300 main body upper portion 2304 is separated from the connector main body lower portion 2306 by a space or channel 2307. The space or channel 2307 is sized and shaped to allow an existing pedicle screw tulip 20 previously implanted into a patient to fit and or rest therein. The tulip head connector 2300 main body 2302 include arms 2310 and 2310.

Figure 33A:
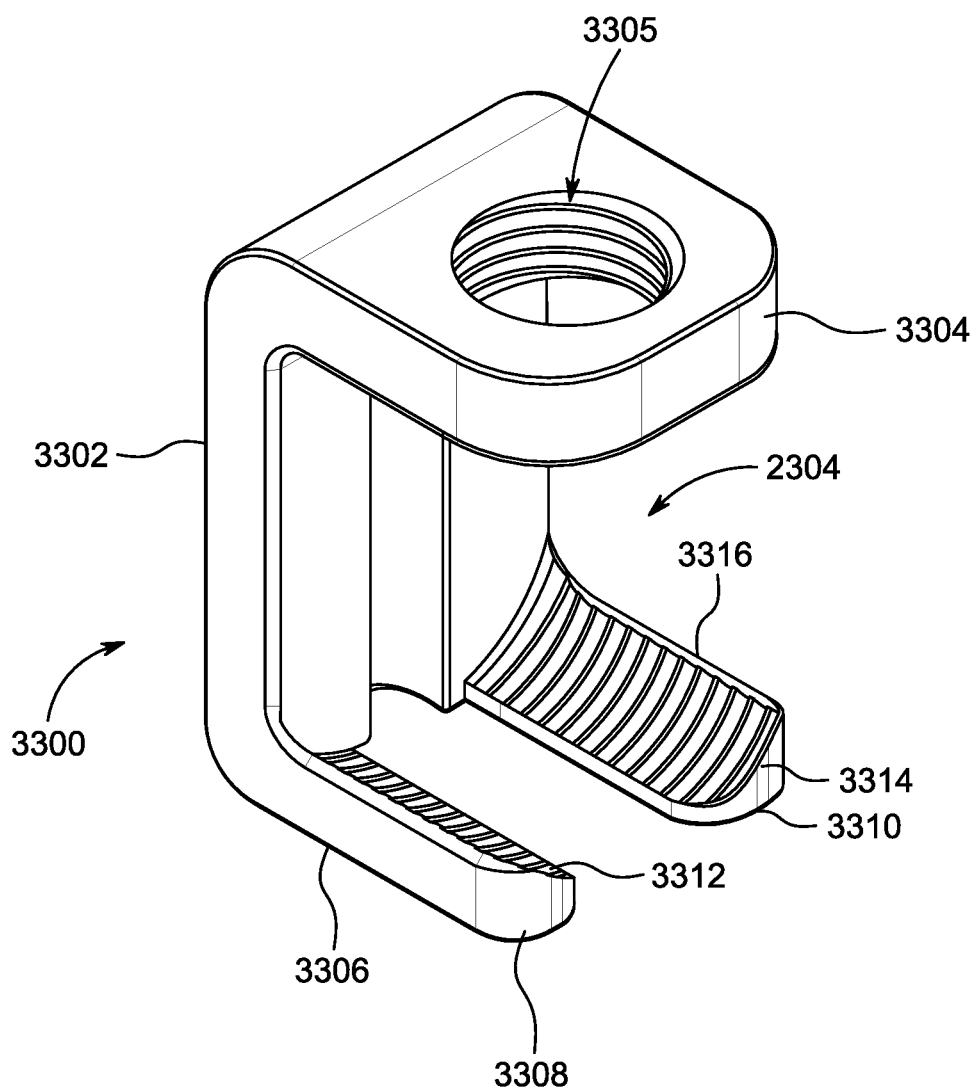
FIG. 33A is a perspective view of an illustrative embodiment of a tulip head connector.
Figure 33B:
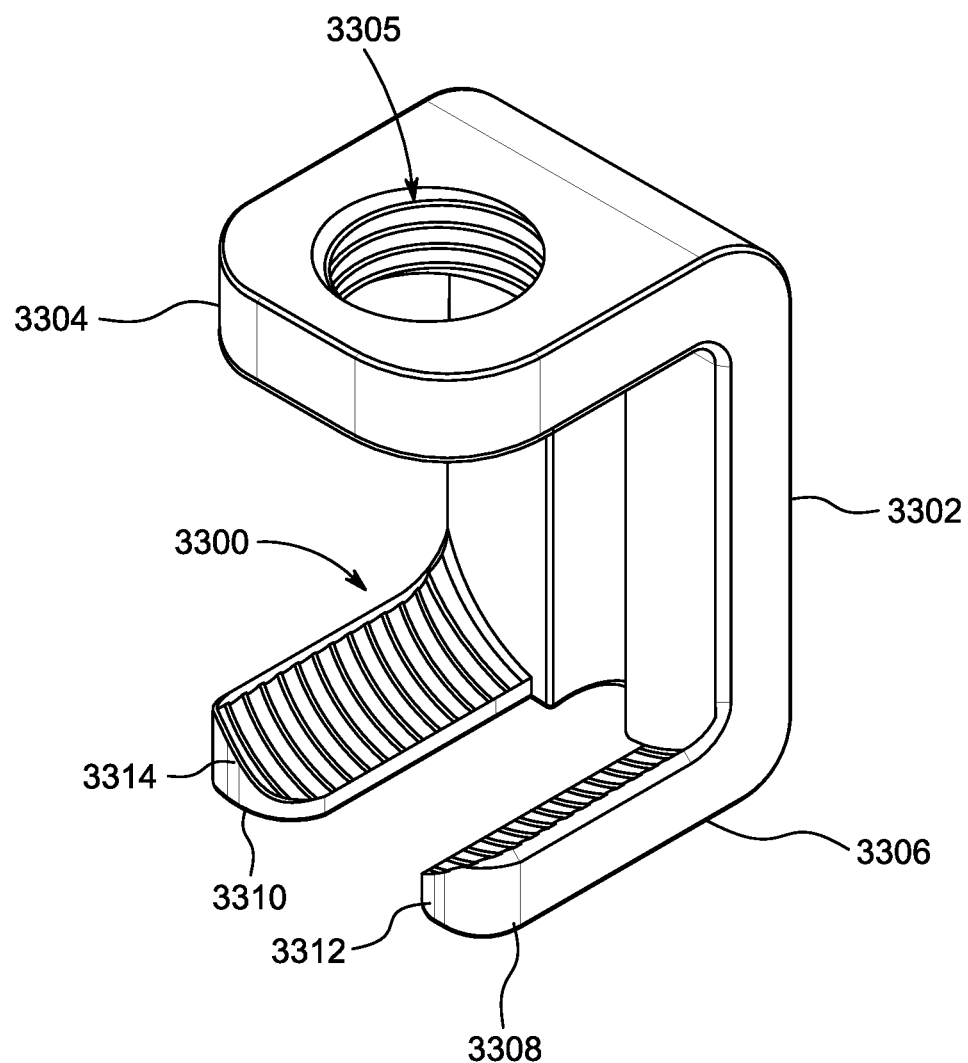
FIG. 33B is an alternative perspective view of the tulip head connector shown in FIG. 33A.
Figure 33C:
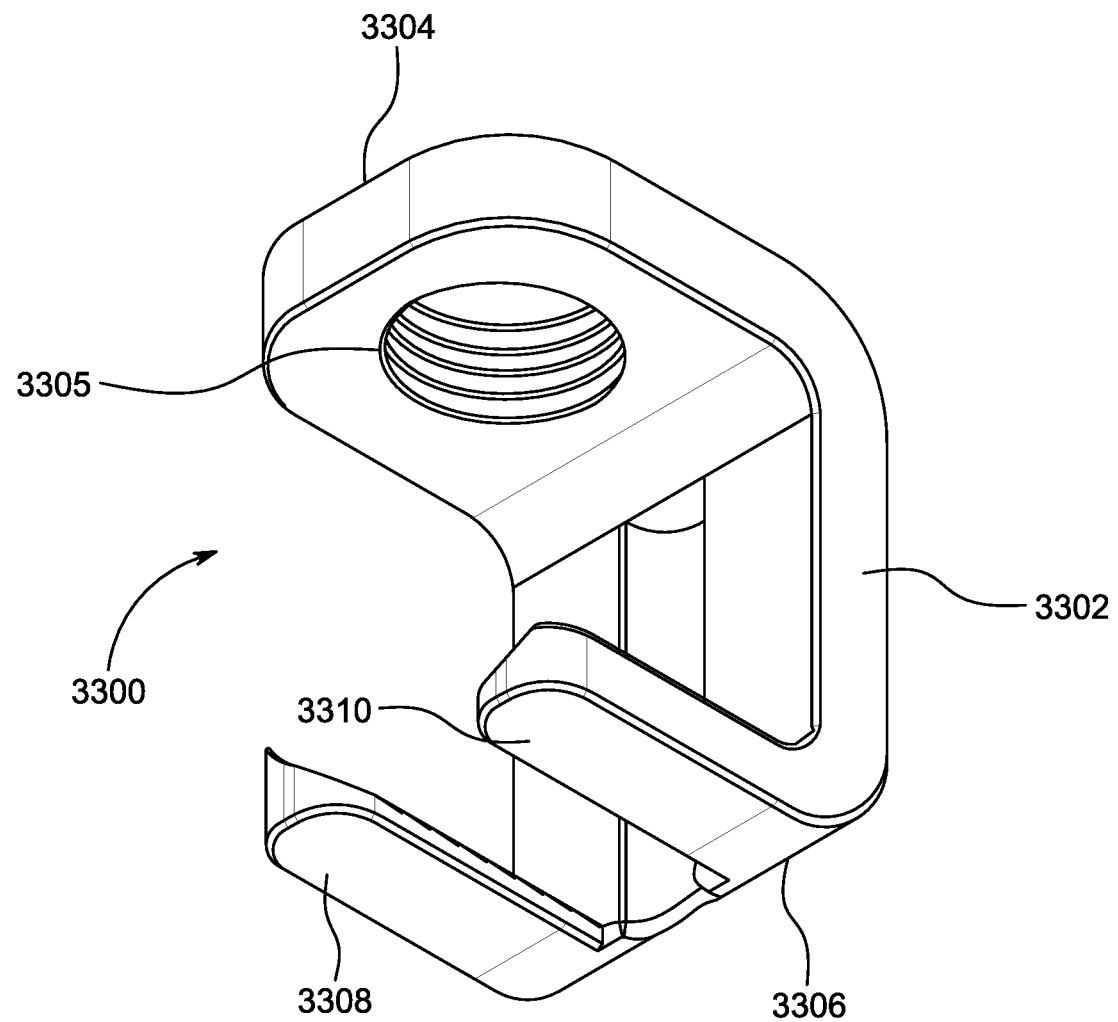
FIG. 33C is a bottom perspective view of the tulip head connector shown in FIG. 33A.
Figure 33D:
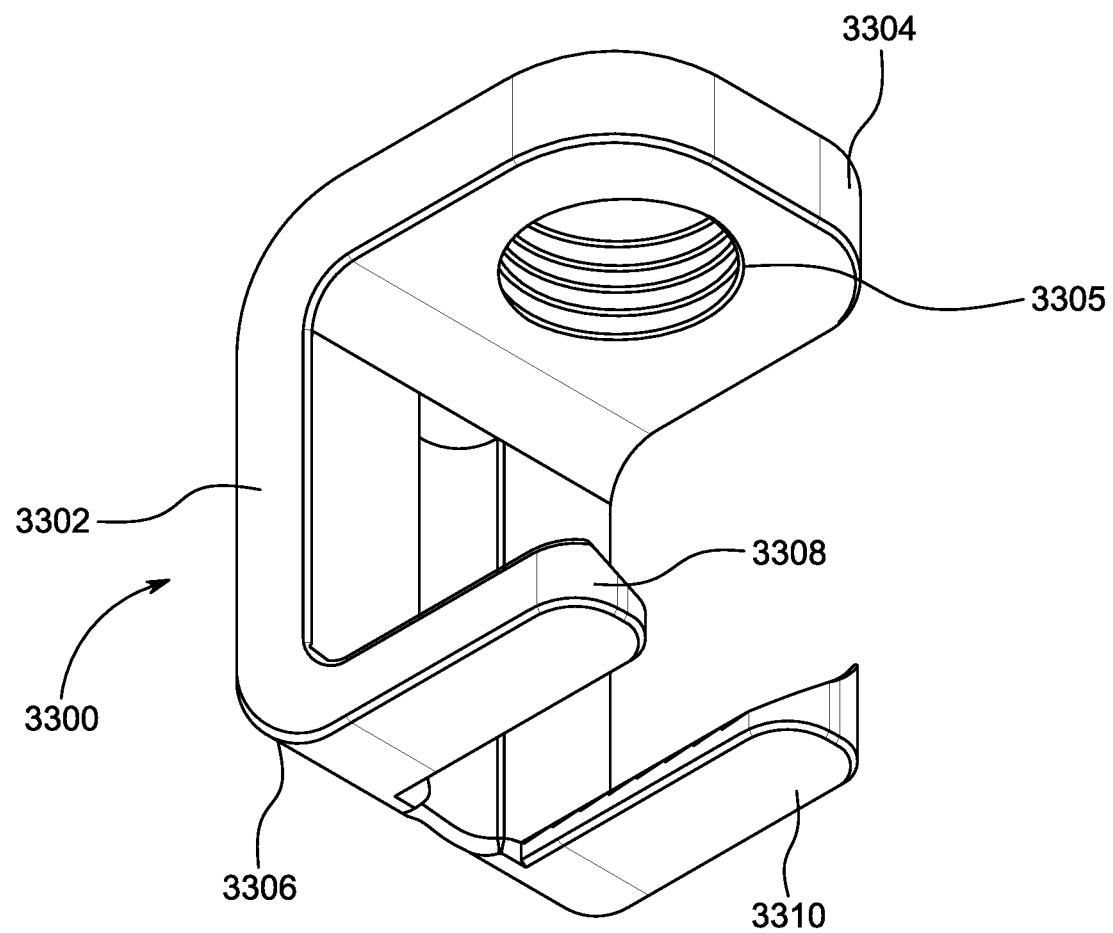
FIG. 33D is an alternative bottom perspective view of the tulip head connector shown in FIG. 33A.
Figure 33E:
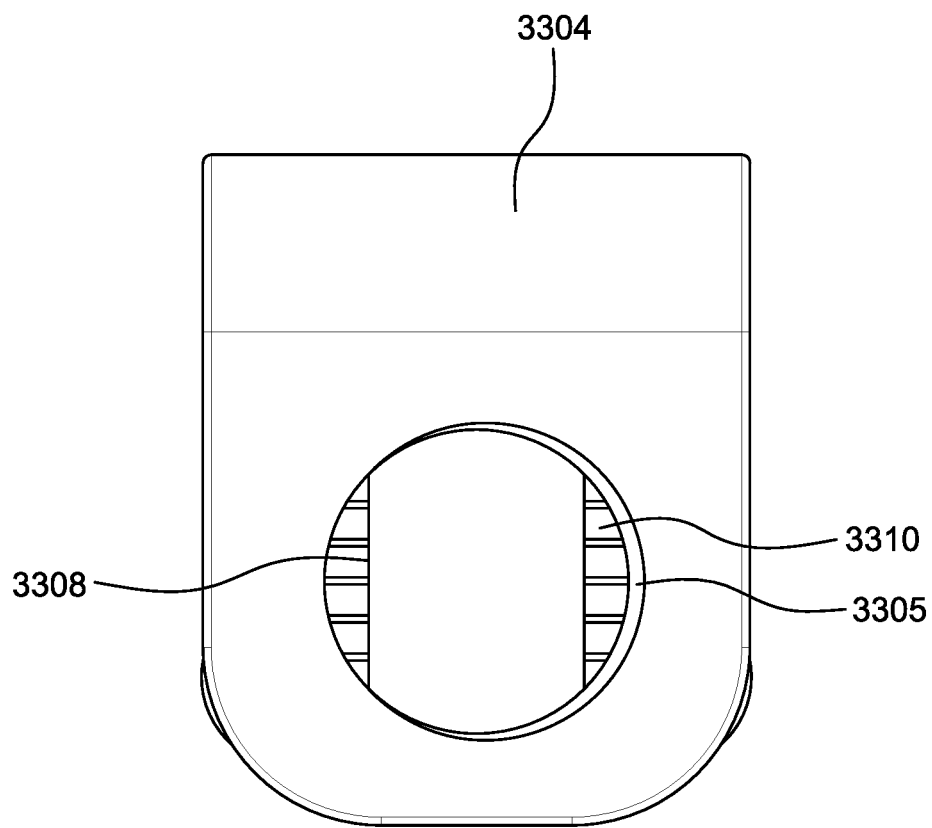
FIG. 33E is a top view of the tulip head connector shown in FIG. 33A.
Figure 33F:
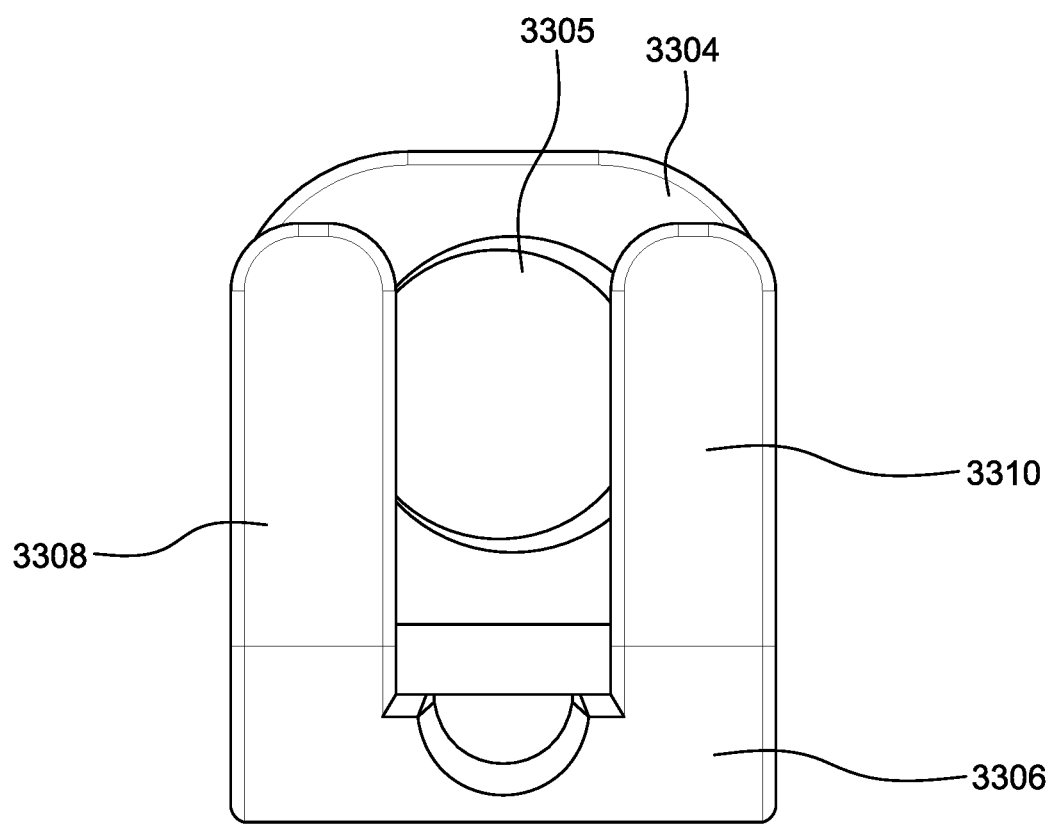
FIG. 33F is a bottom view of the tulip head connector shown in FIG. 33A.
Figure 33G:
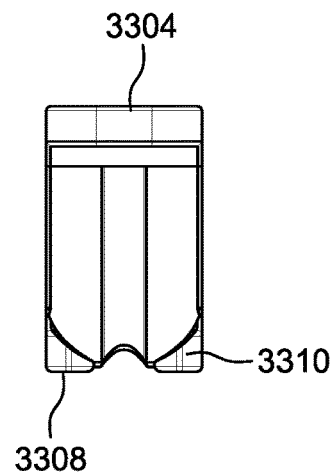
FIG. 33G is a front view of the tulip head connector shown in FIG. 33A.
Figure 33H:
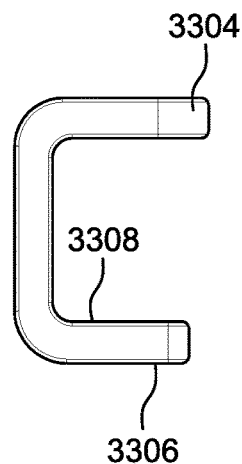
FIG. 33H is a right side of the tulip head connector in FIG. 33A.
Figure 33I:
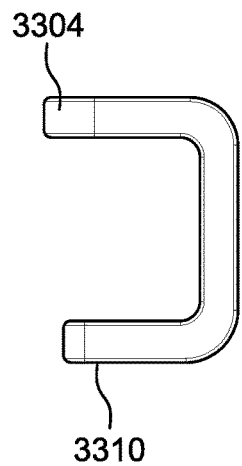
FIG. 33I is a left side of the tulip head connector shown in FIG. 33A.

Referring to FIGS. 33A-33T, the rod connector 3300 is configured to engage with and secure to a previously implanted rod 22. The tulip head connector 3300 is configured to connect to a tulip head having a curved surface. The tulip head connector 3300 may comprise a main body 3302 having an upper portion 3304 configured to engage with pedicle screw set screw (threaded opening 3305) and/or a retractor blade, and a lower portion 3306 configured to engage with a preexisting surgical device, such as a previously implanted pedicle screw tulip 20. The add tulip head connector 3300 main body upper portion 3304 is separated from the connector main body lower portion 2306 by a space or channel 3307. The space or channel 3307 is sized and shaped to allow an existing pedicle screw tulip 20 previously implanted into a patient to fit and or rest therein. The tulip head connector main body 3302 include arms 3308 and 3310. Arms 3308 and 3310 may include curved and/or angled surfaces 3312 and 3314 (correspond to the curvature of the tulip head). Arms 3308 and 3310 may include a knurled 3316 for use in gripping.

Figure 34A:
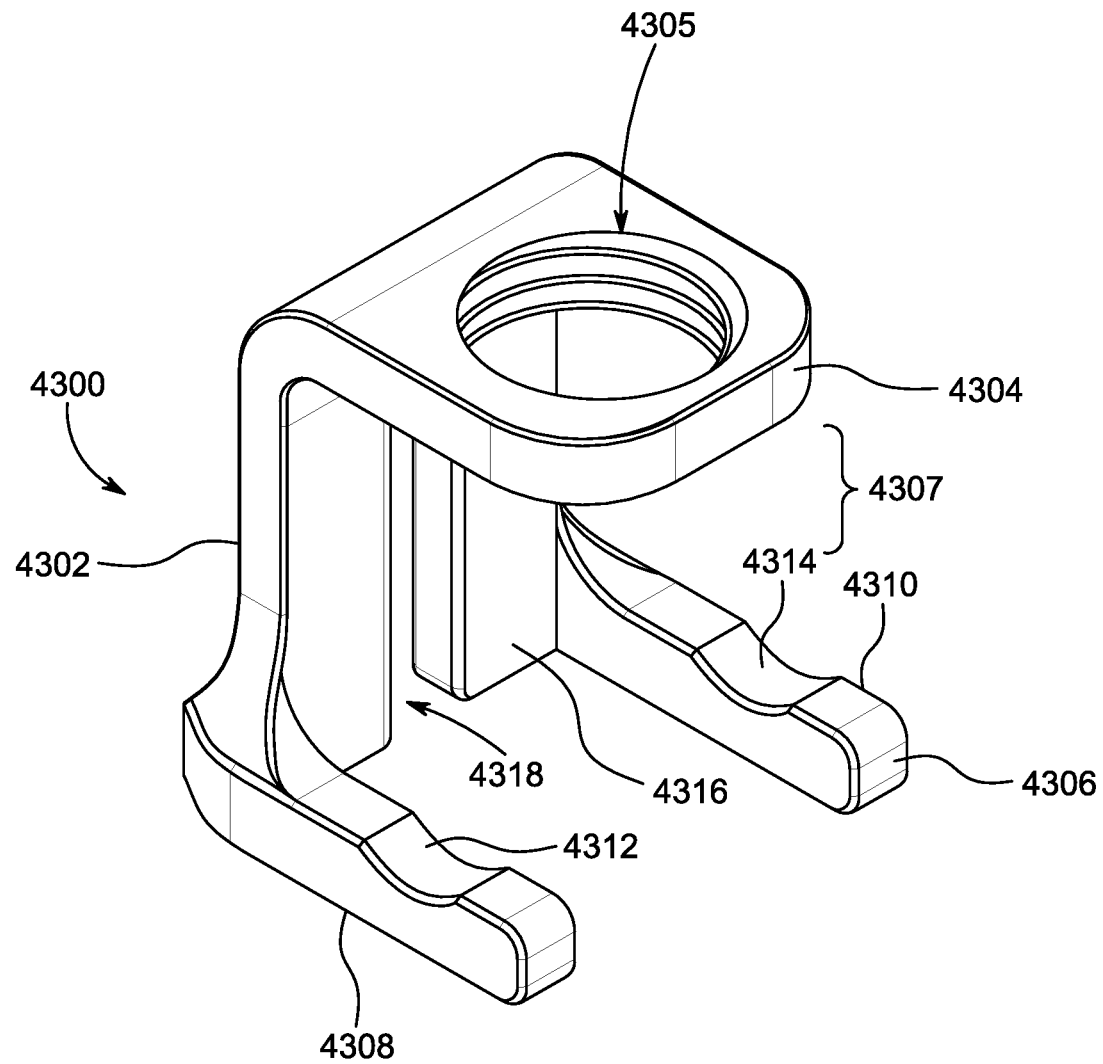
FIG. 34A is a perspective view of an illustrative embodiment of a tulip head connector.
Figure 34B:
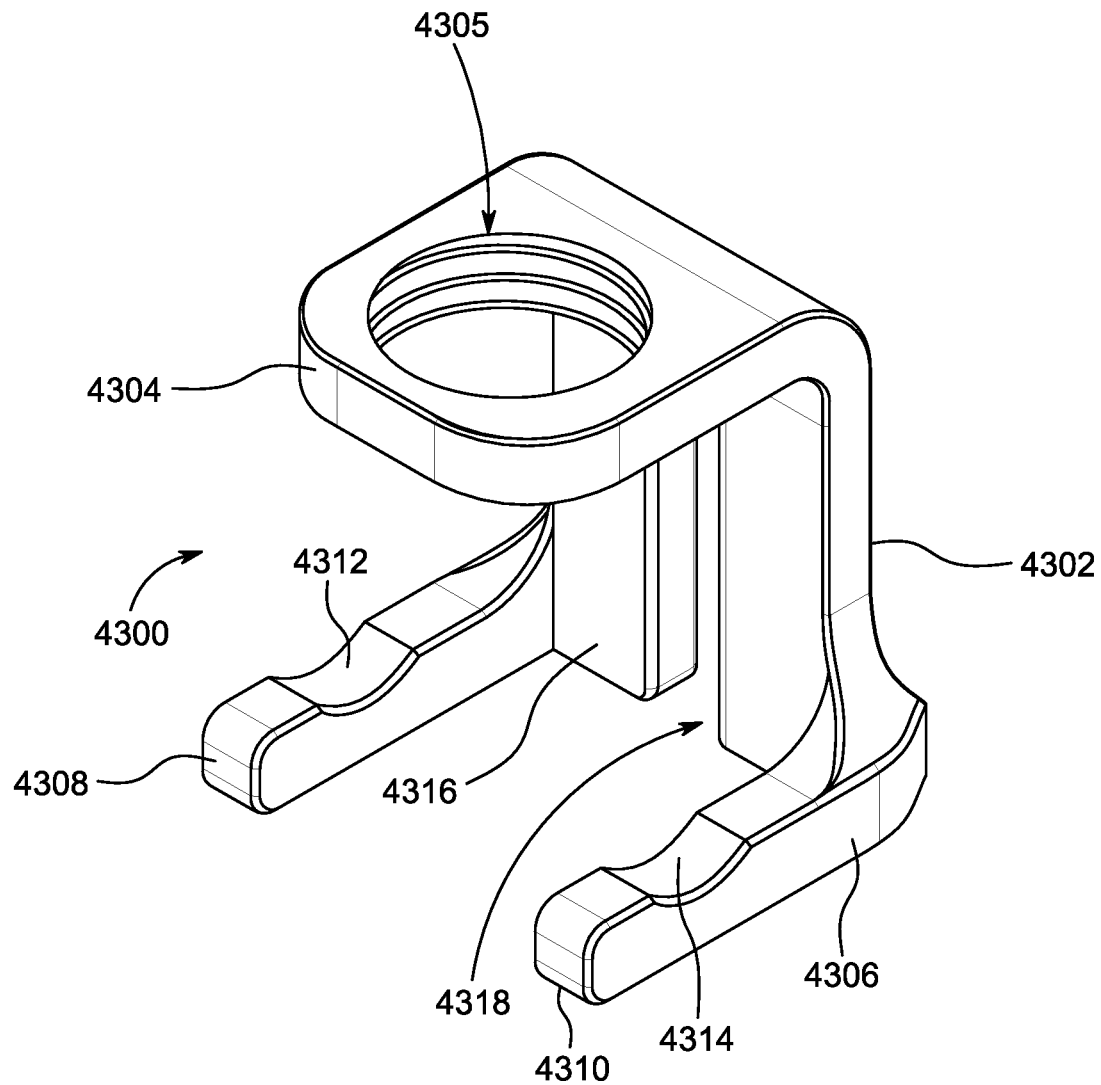
FIG. 34B is an alternative perspective view of the tulip head connector shown in FIG. 34A.
Figure 34C:
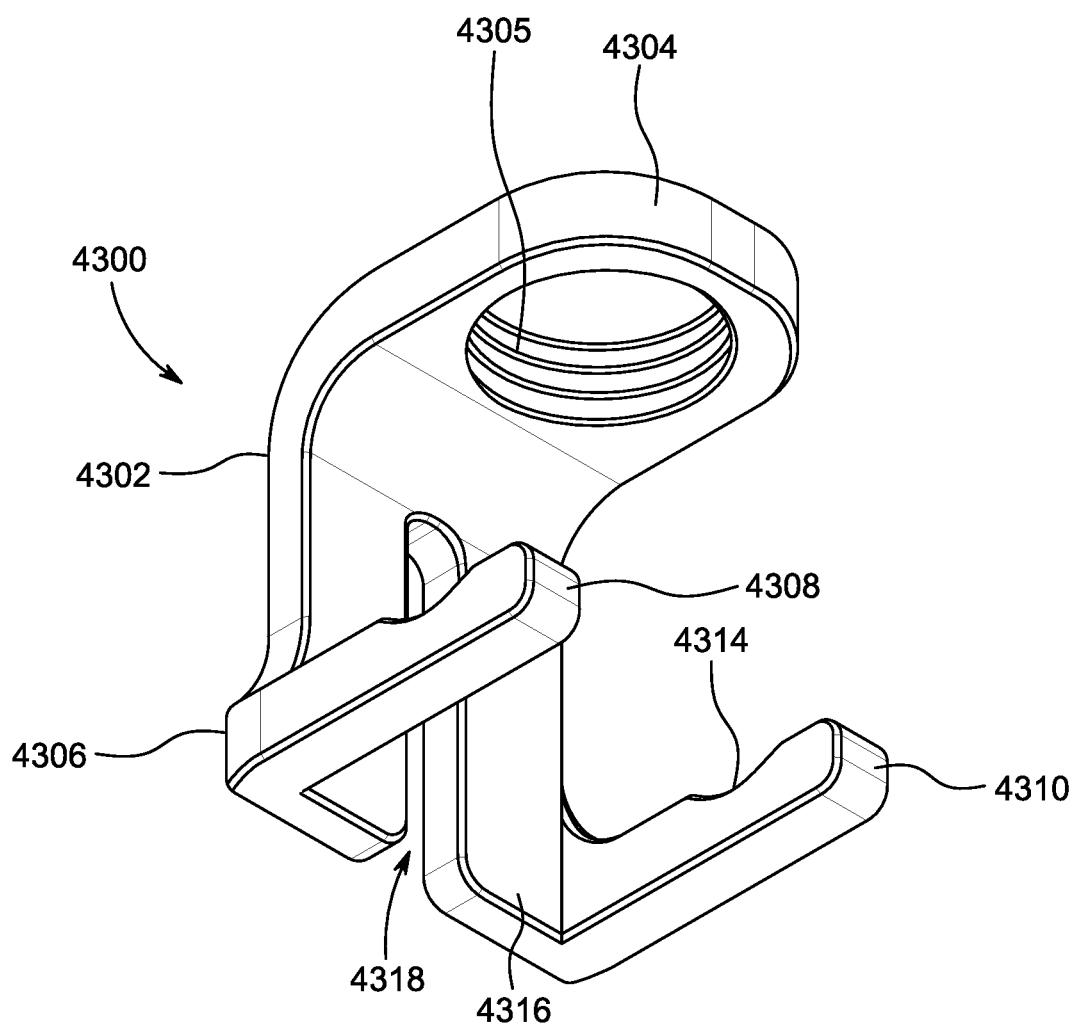
FIG. 34C is a bottom perspective view of the tulip head connector shown in FIG. 34A.
Figure 34D:
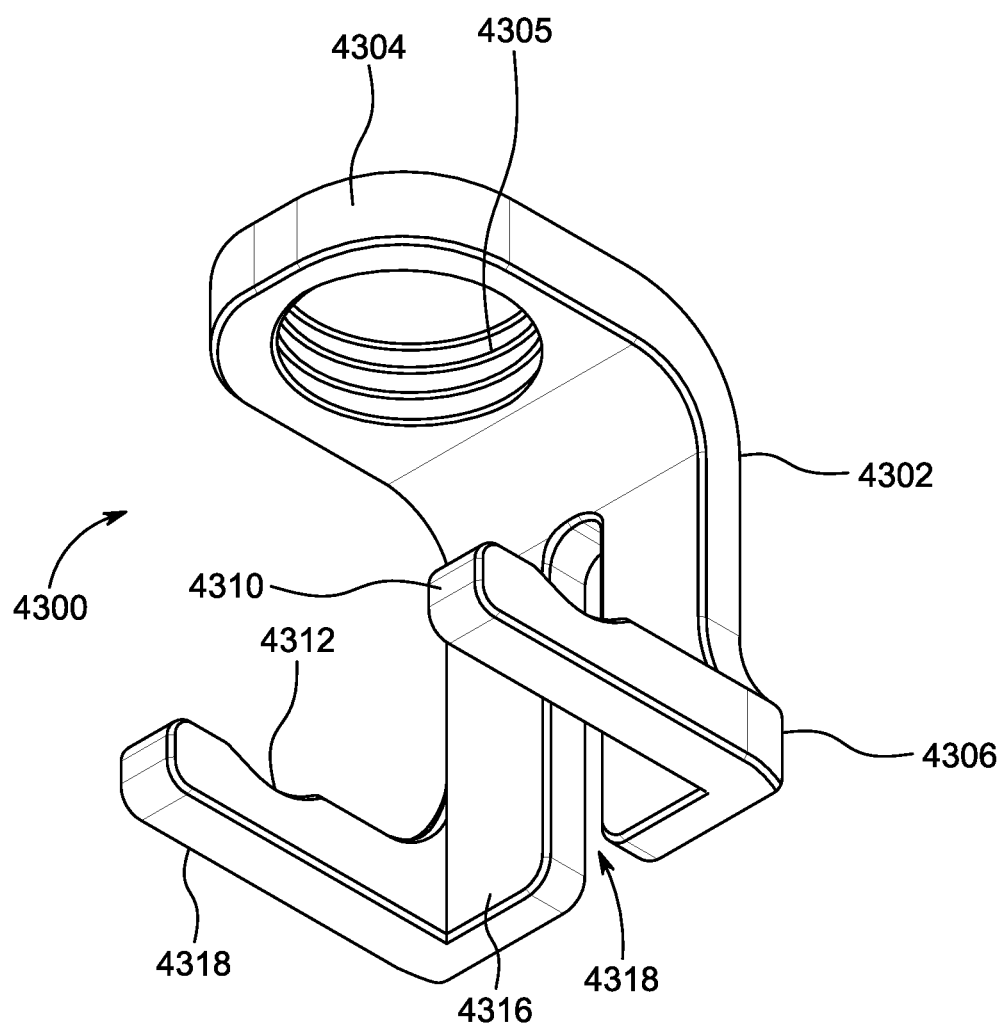
FIG. 34D is an alternative bottom perspective view of the tulip head connector shown in FIG. 34A.
Figure 34E:
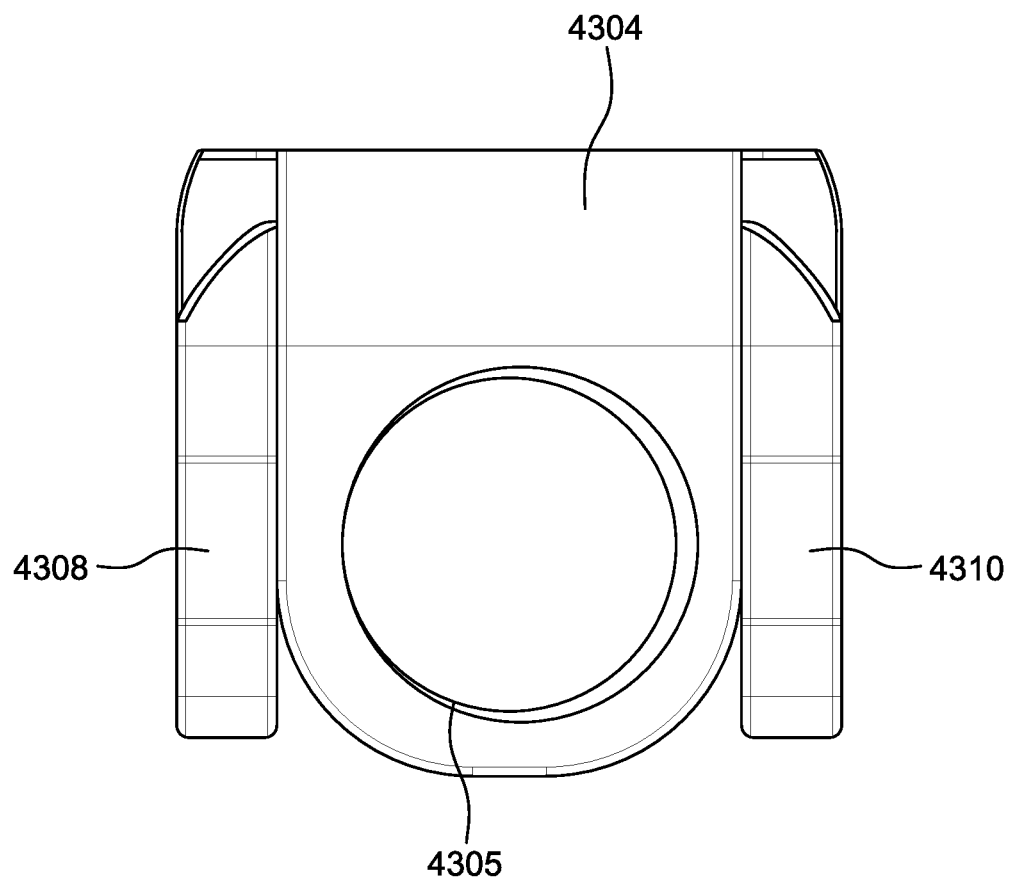
FIG. 34E is a top view of the tulip head connector shown in FIG. 34A.
Figure 34F:
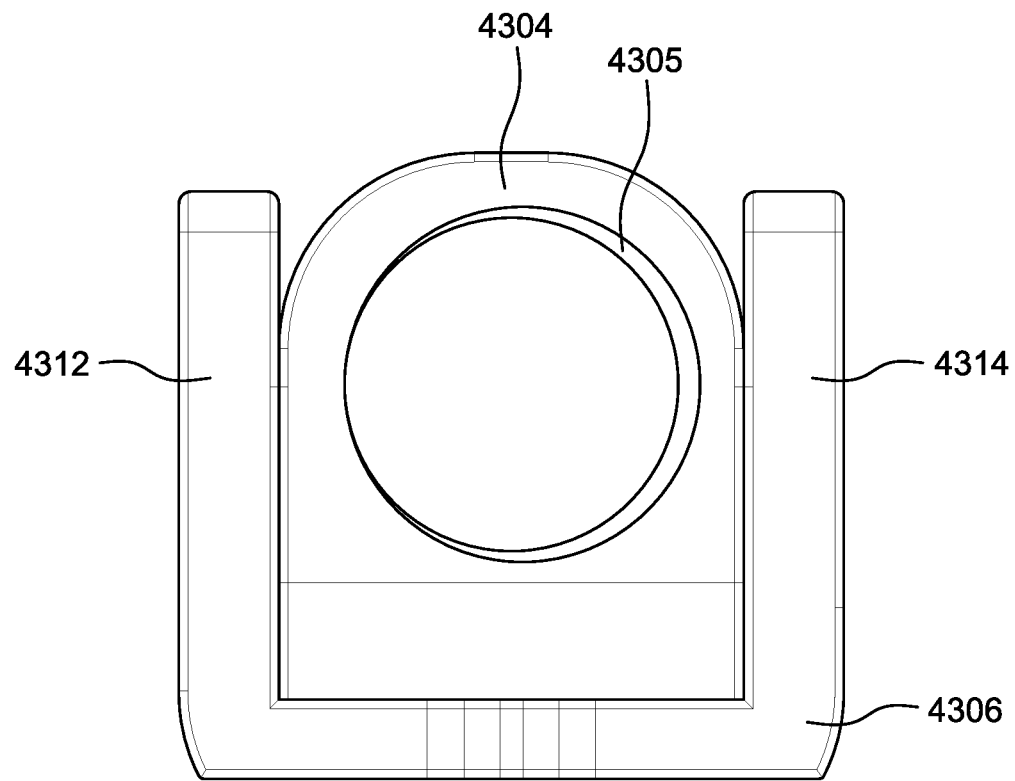
FIG. 34F is a bottom view of the tulip head connector shown in FIG. 34A.
Figure 34G:
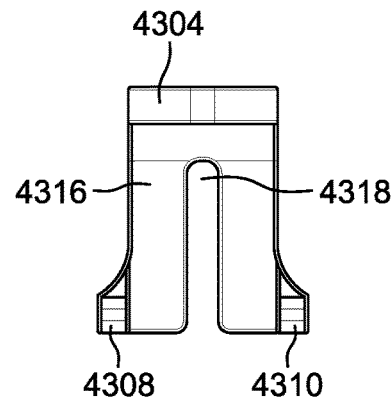
FIG. 34G is a front view of the tulip head connector shown in FIG. 34A.
Figure 34H:
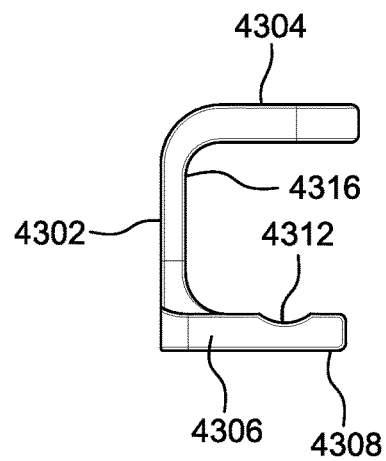
FIG. 34H is a right side of the tulip head connector in FIG. 34A.
Figure 34I:
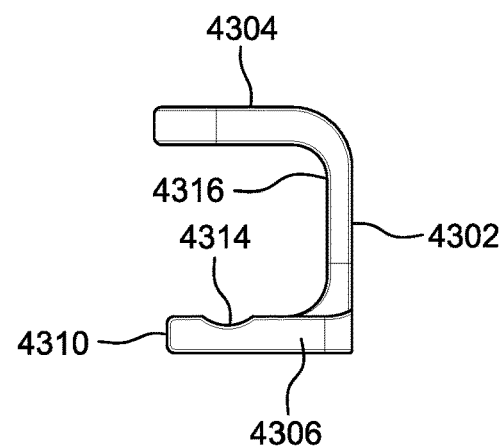
FIG. 34I is a left side of the tulip head connector shown in FIG. 34A.
Figure 35A:
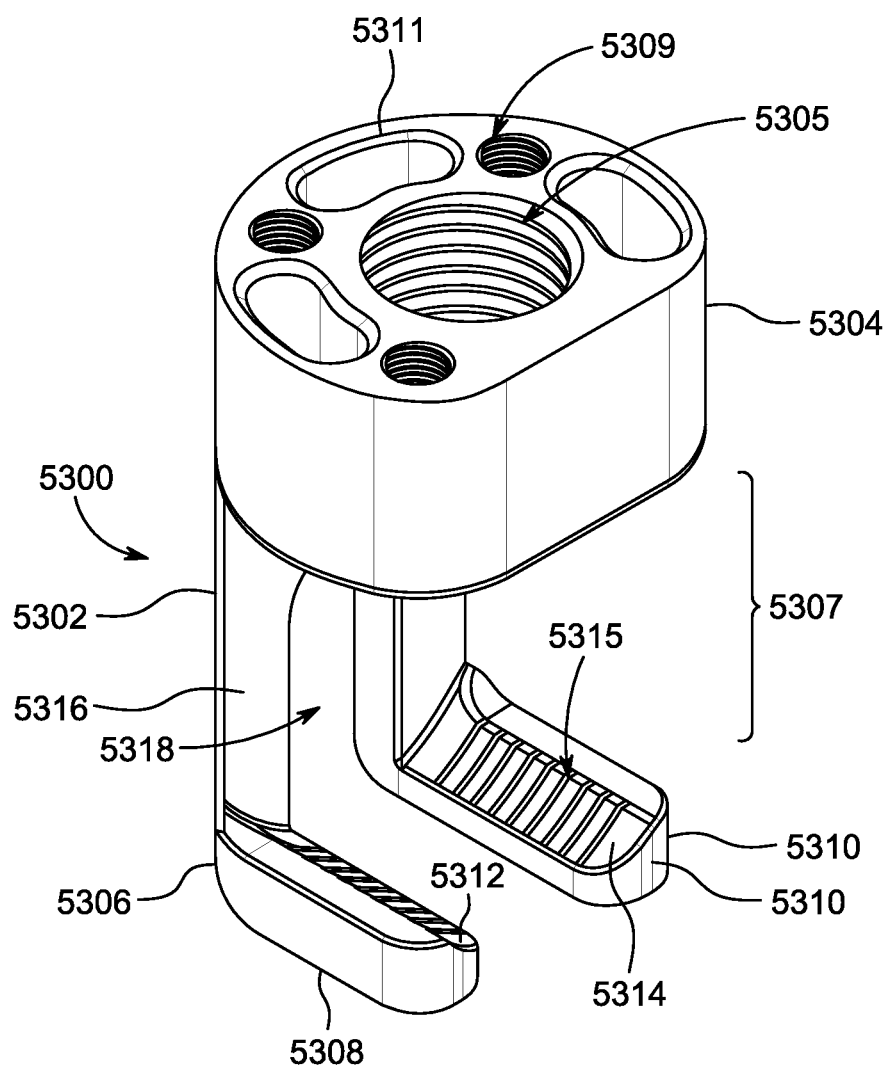
FIG. 35A is a perspective view of an illustrative embodiment of a tulip head connector.
Figure 35B:
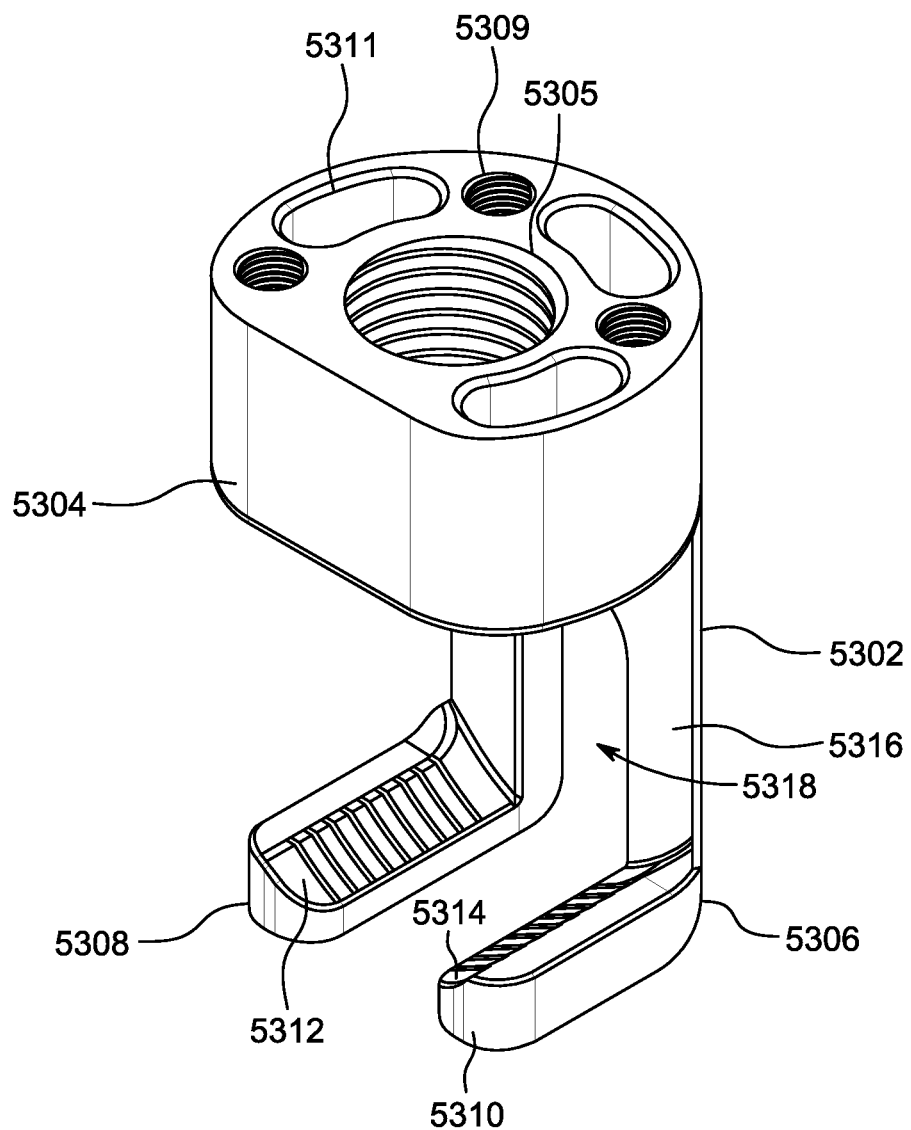
FIG. 35B is an alternative perspective view of the tulip head connector shown in FIG. 35A.
Figure 35C:
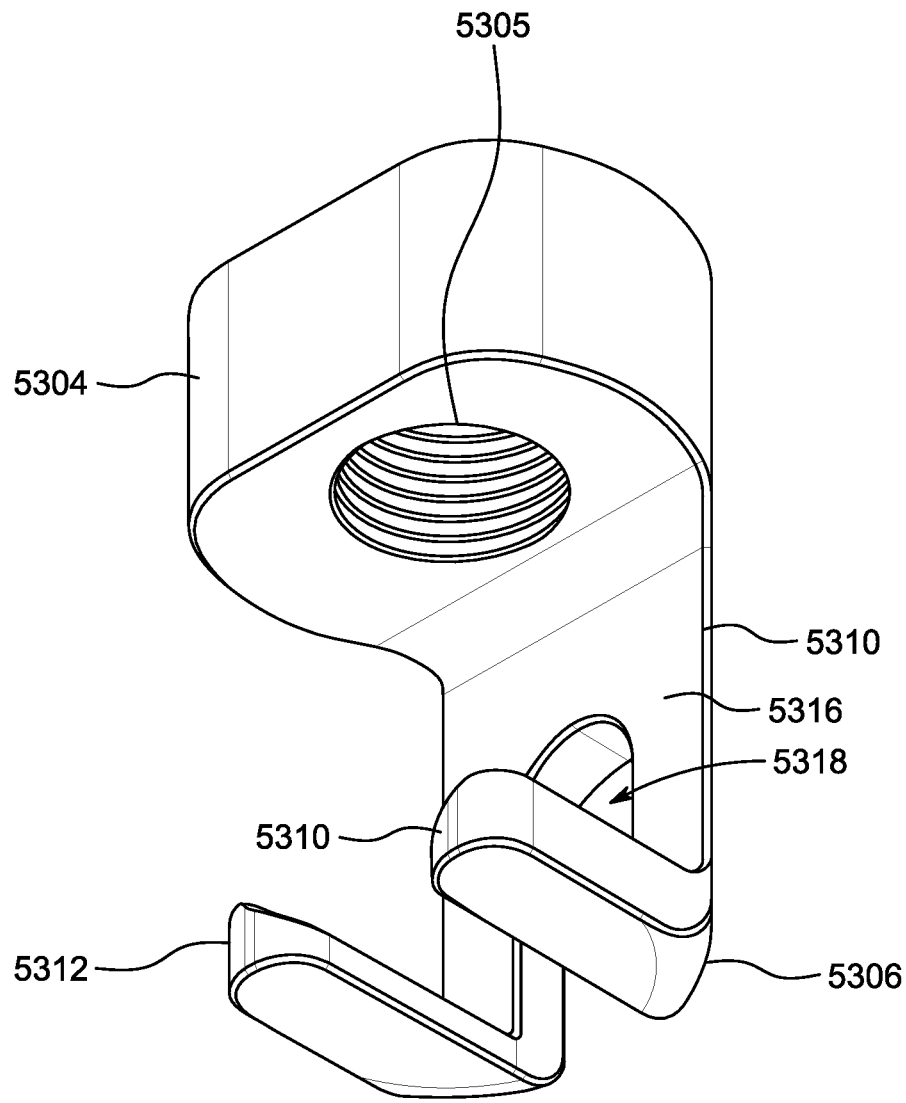
FIG. 35C is a bottom perspective view of the tulip head connector shown in FIG. 35A.
Figure 35D:
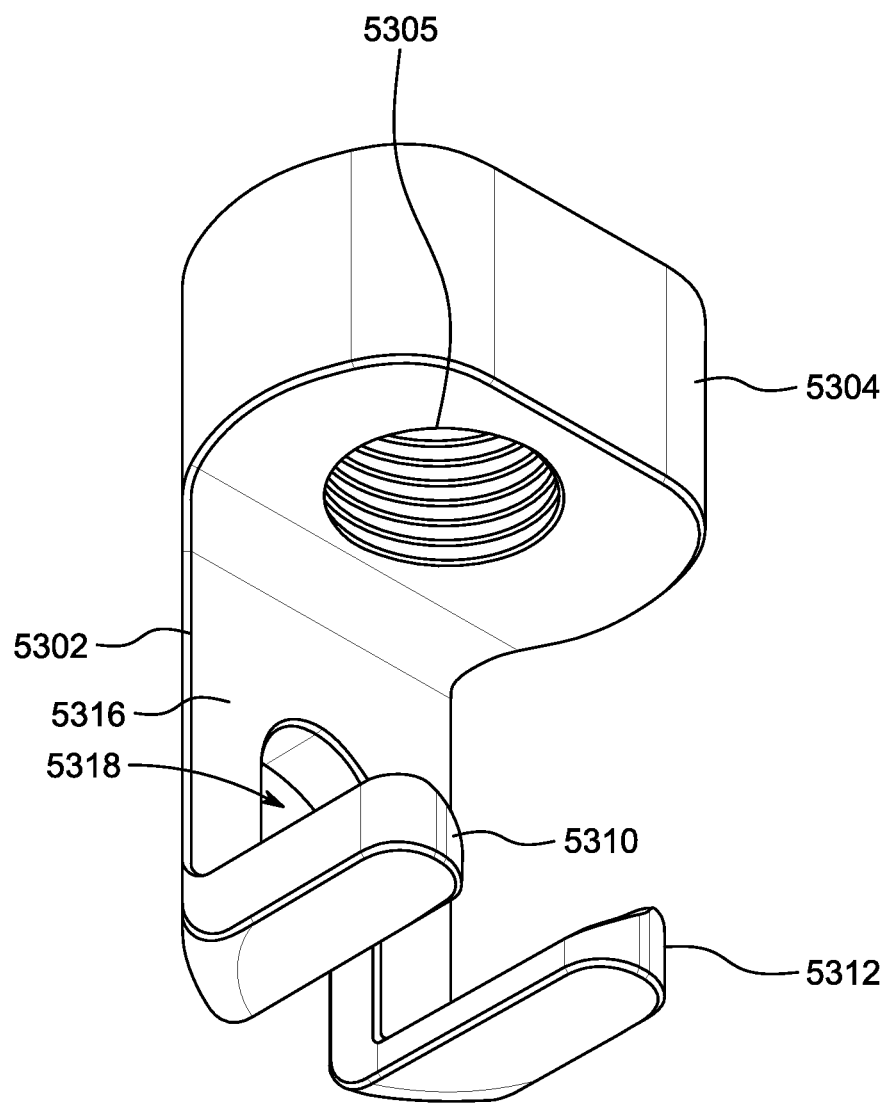
FIG. 35D is an alternative bottom perspective view of the tulip head connector shown in FIG. 35A.
Figure 35E:
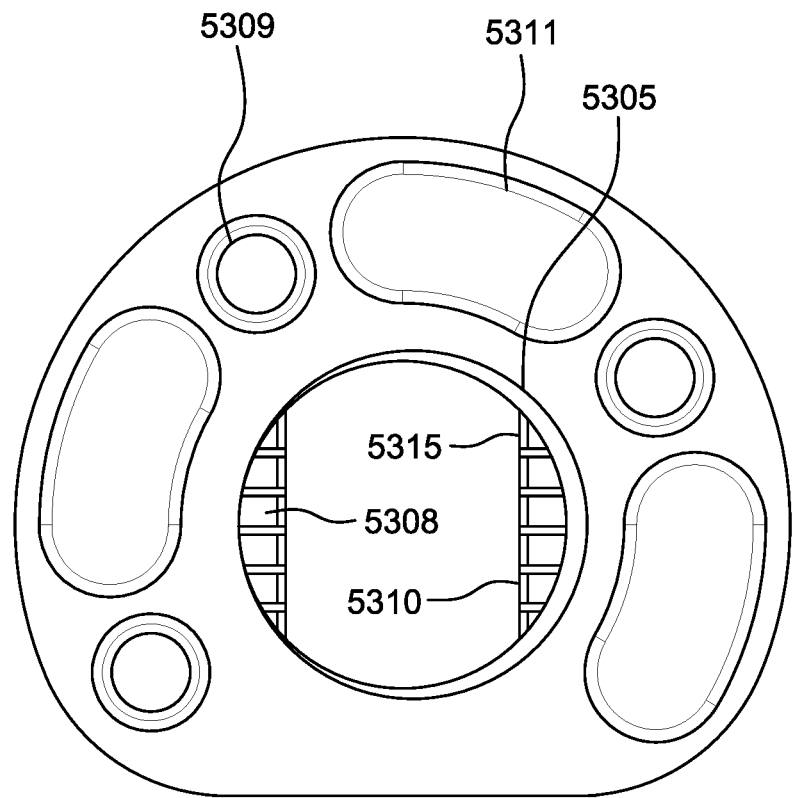
FIG. 35E is a top view of the tulip head connector shown in FIG. 35A.
Figure 35F:
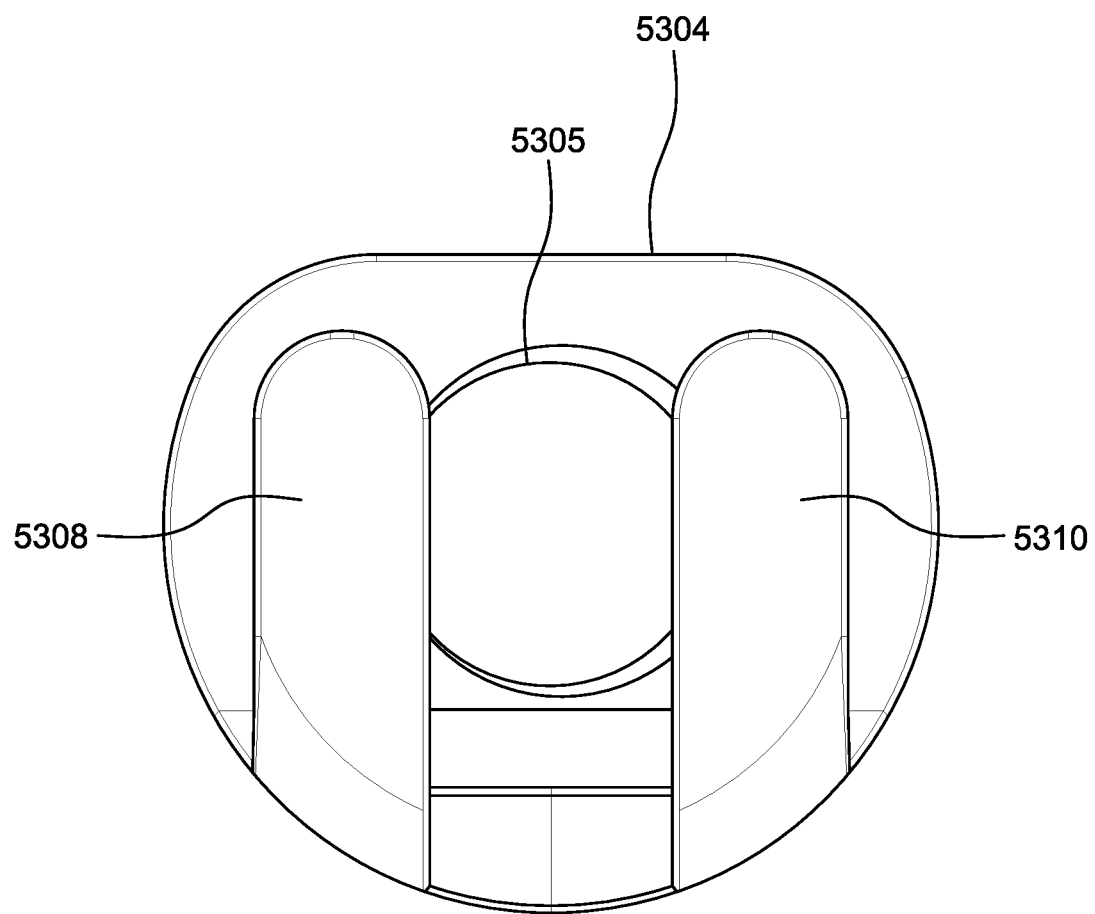
FIG. 35F is a bottom view of the tulip head connector shown in FIG. 35A.
Figure 35G:
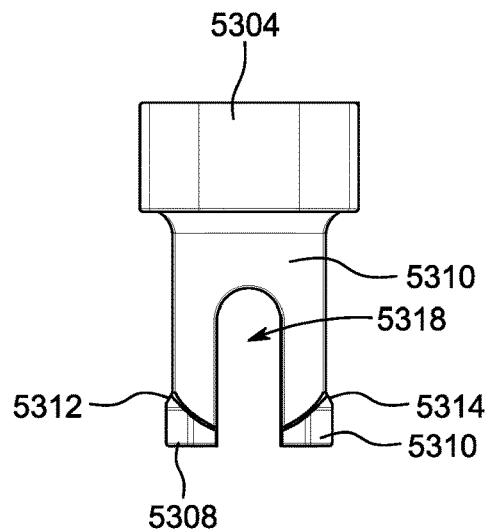
FIG. 35G is a front view of the tulip head connector shown in FIG. 35A.
Figure 35H:
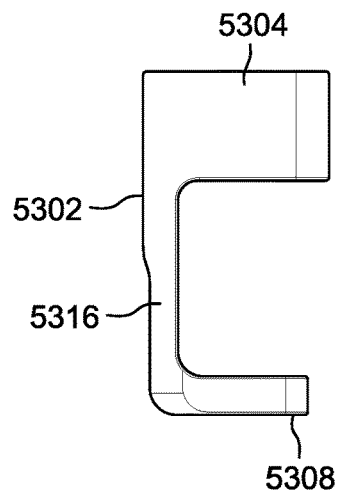
FIG. 35H is a right side of the tulip head connector in FIG. 35A.
Figure 35I:
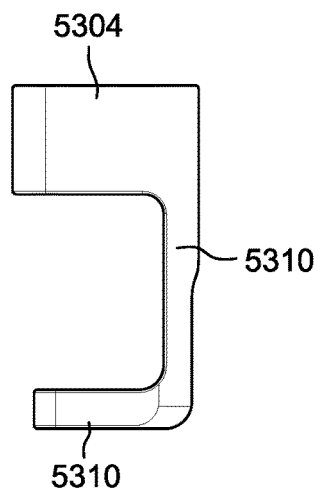
FIG. 35I is a left side of the tulip head connector shown in FIG. 35A.
Figure 36A:
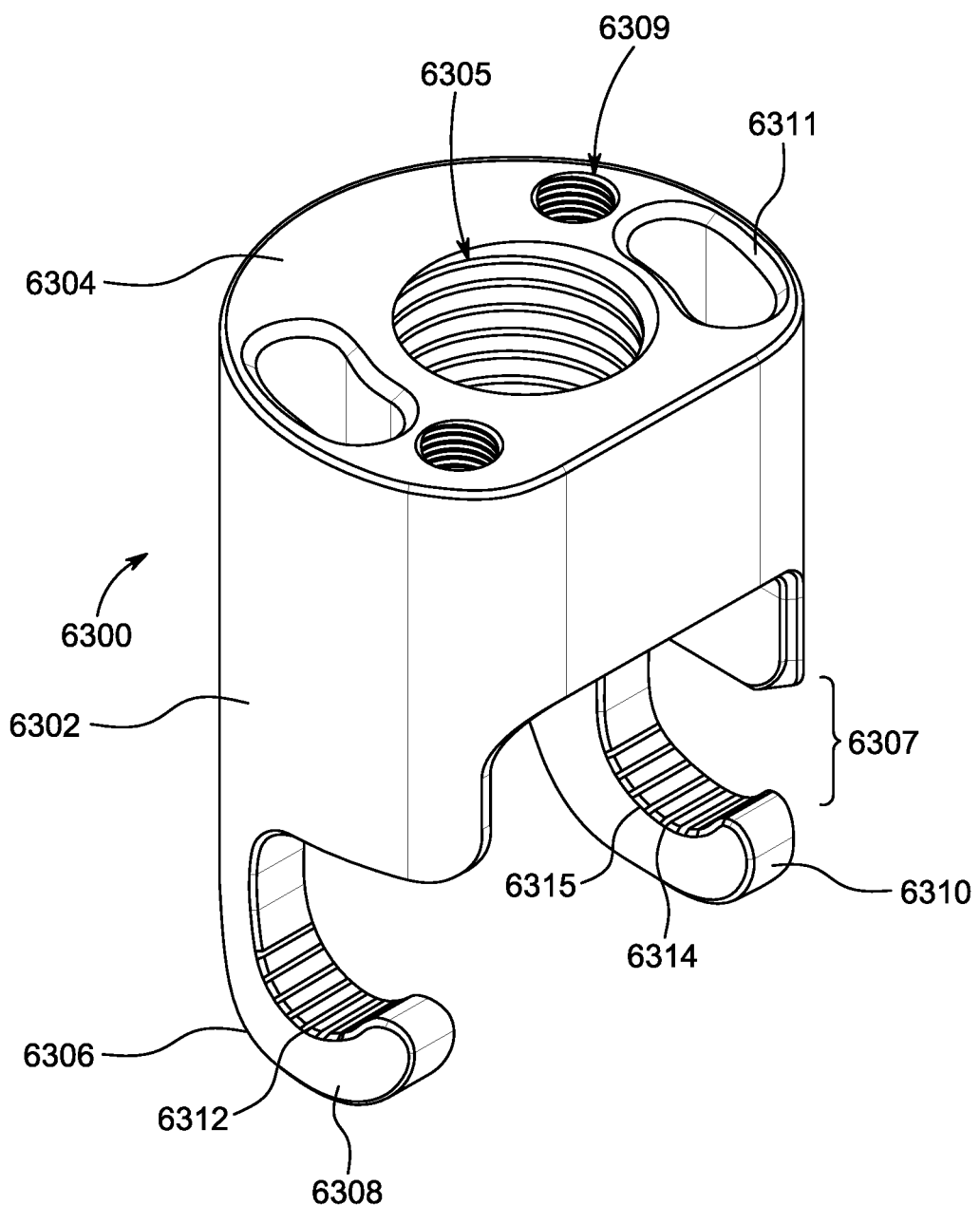
FIG. 36A is a perspective view of an illustrative embodiment of a tulip head connector.
Figure 36B:
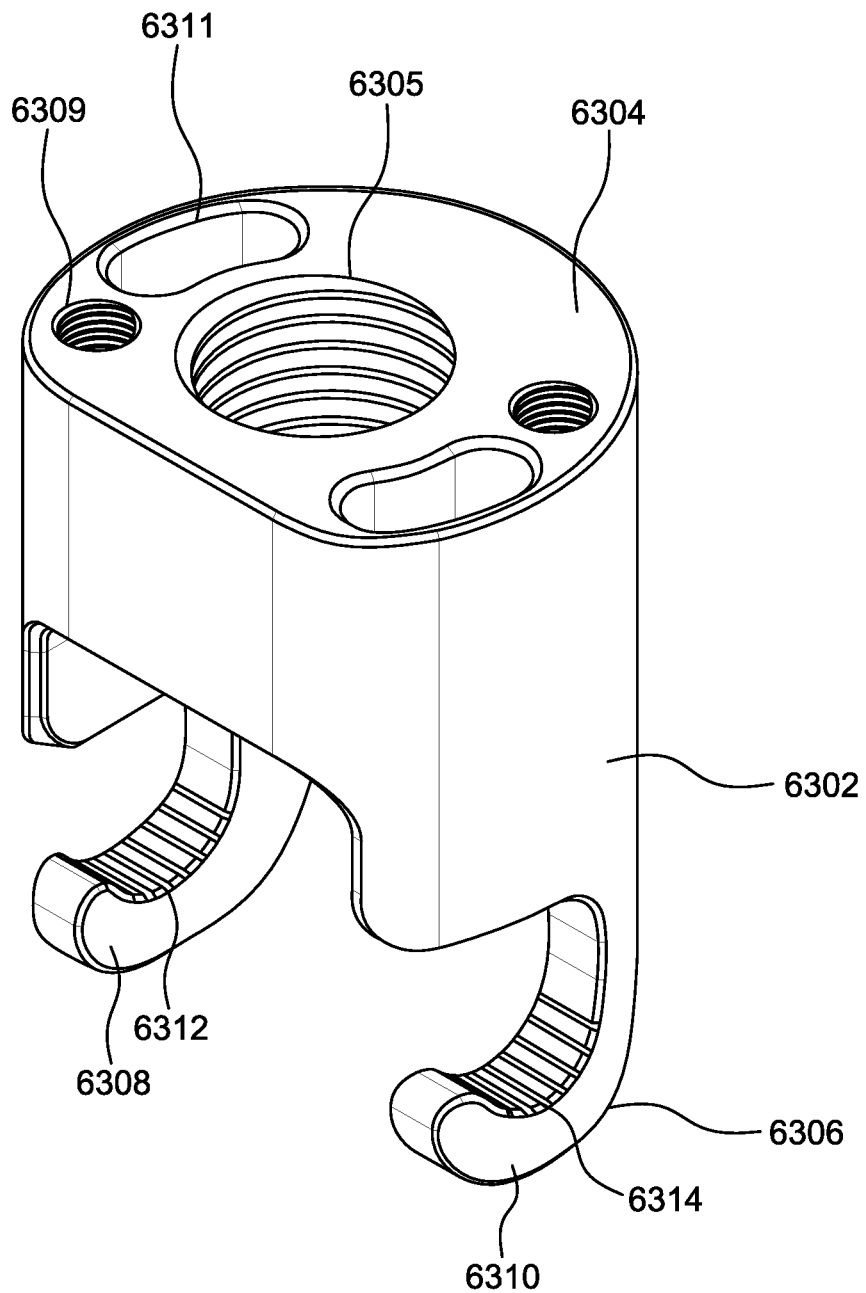
FIG. 36B is an alternative perspective view of the tulip head connector shown in FIG. 36A.
Figure 36C:
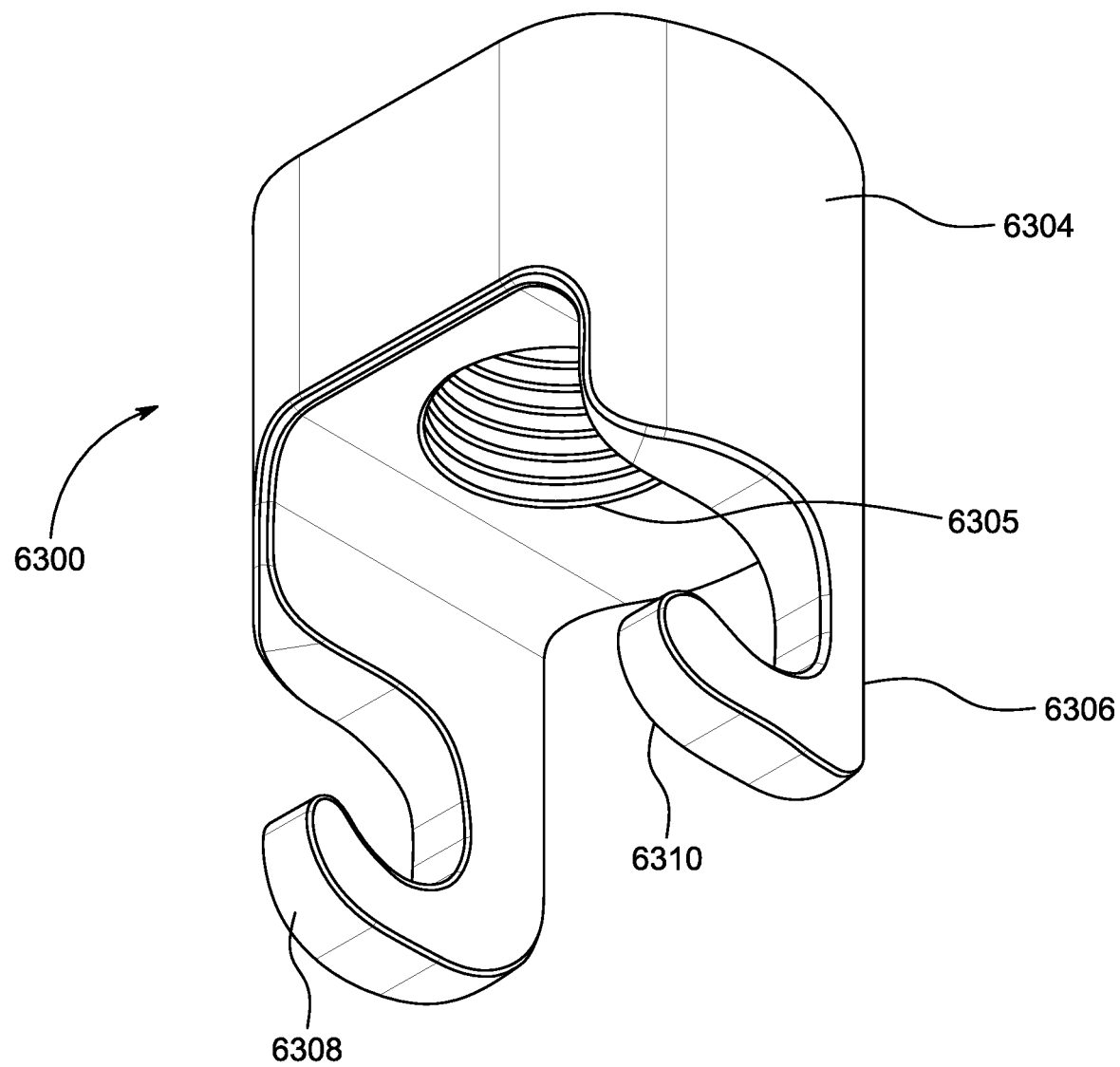
FIG. 36C is a bottom perspective view of the tulip head connector shown in FIG. 36A.
Figure 36D:
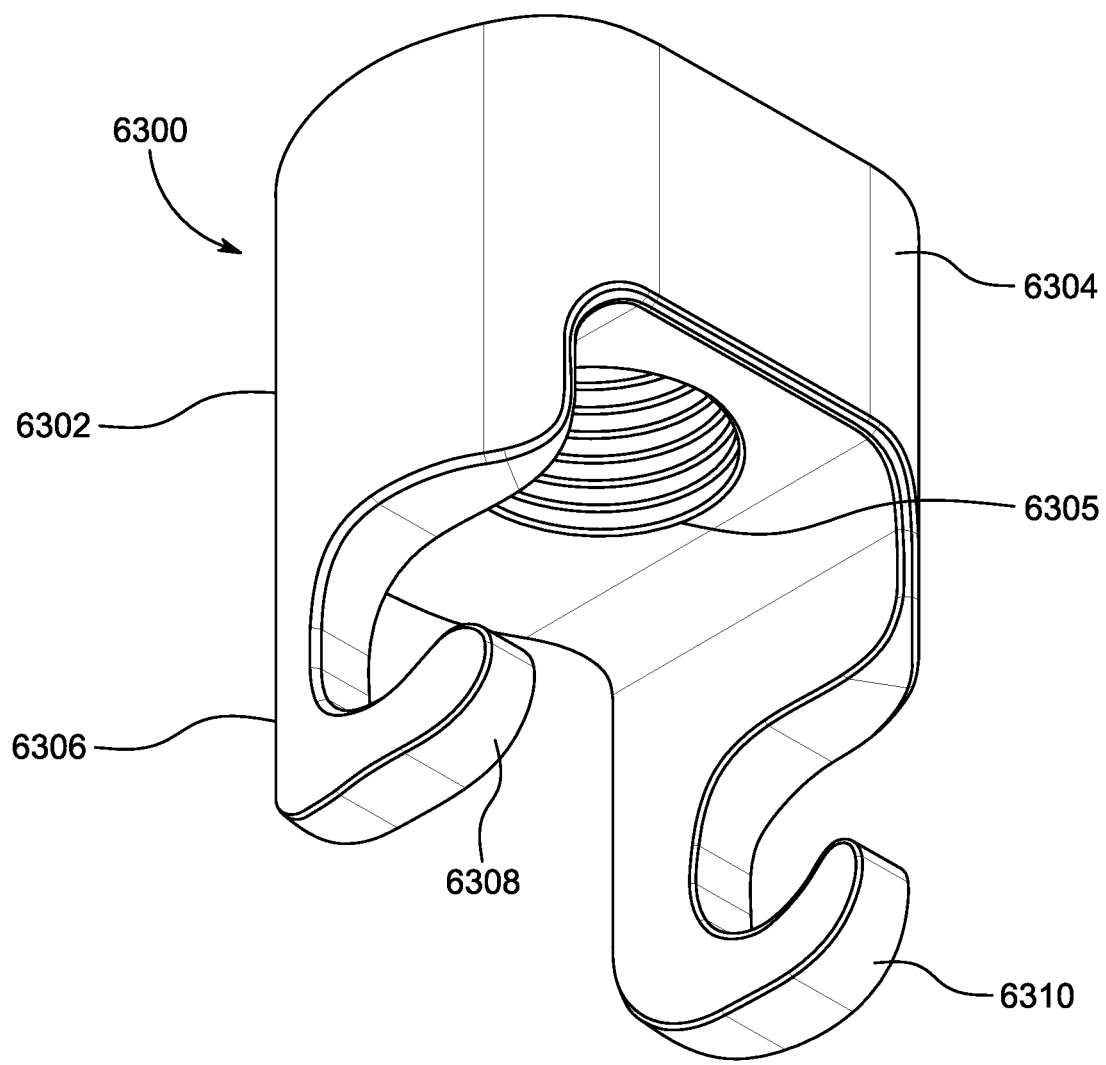
FIG. 36D is an alternative bottom perspective view of the tulip head connector shown in FIG. 36A.
Figure 36E:
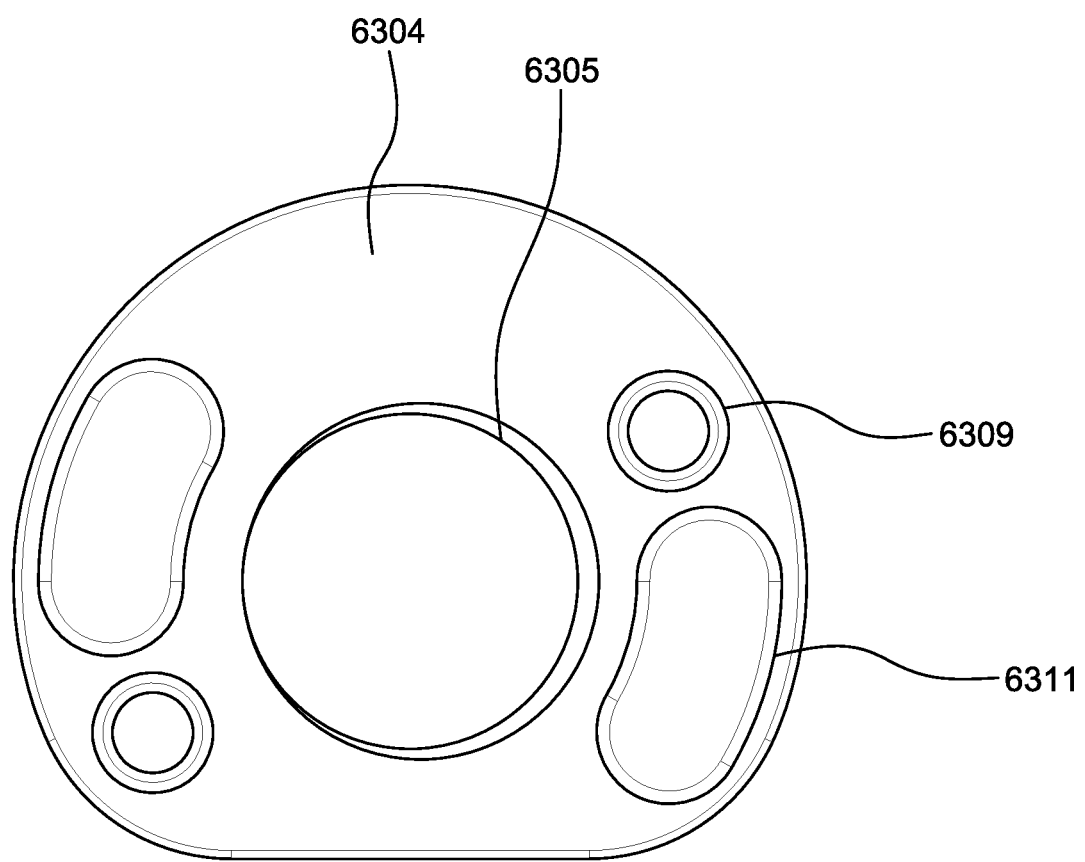
FIG. 36E is a top view of the tulip head connector shown in FIG. 36A.
Figure 36F:
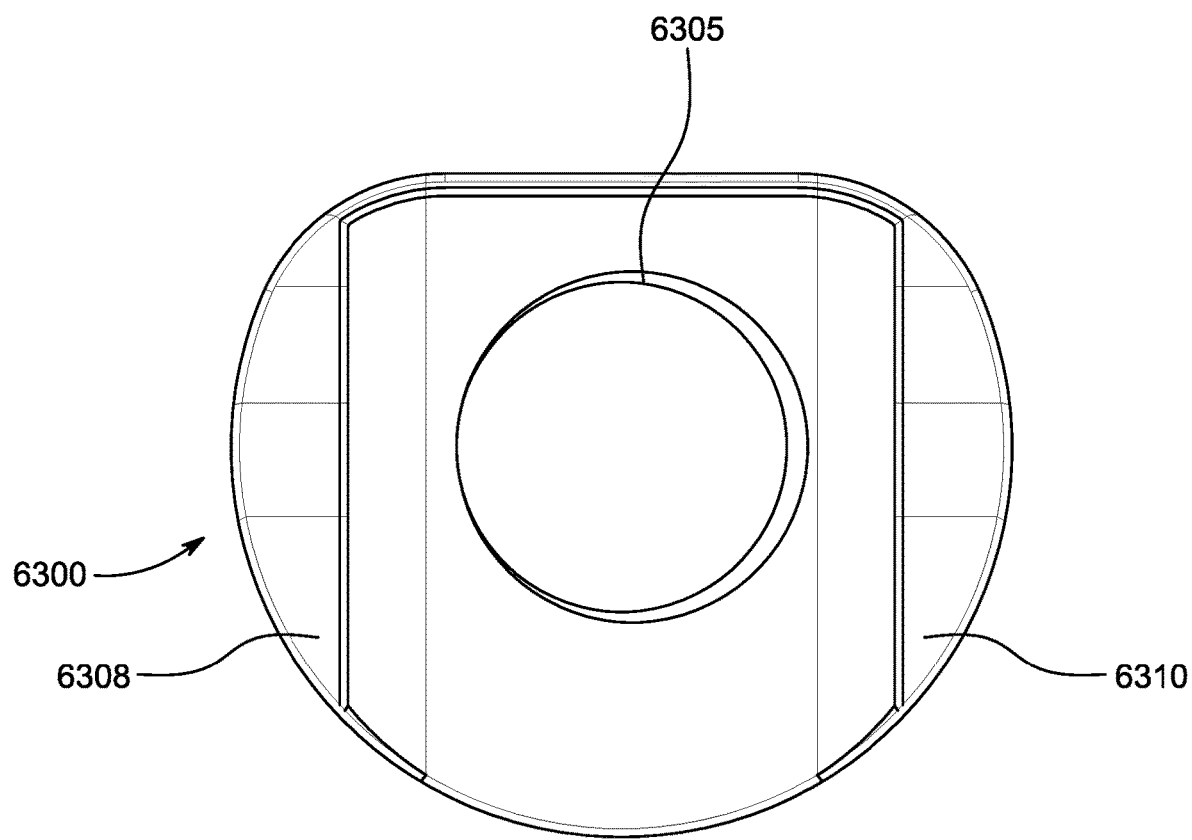
FIG. 36F is a bottom view of the tulip head connector shown in FIG. 36A.
Figure 36G:
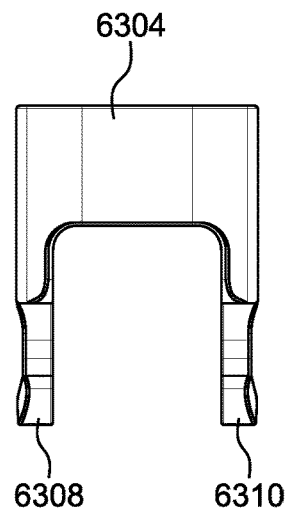
FIG. 36G is a front view of the tulip head connector shown in FIG. 36A.
Figure 36H:
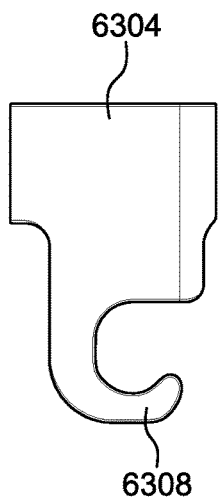
FIG. 36H is a right side of the tulip head connector in FIG. 32A.
Figure 36I:
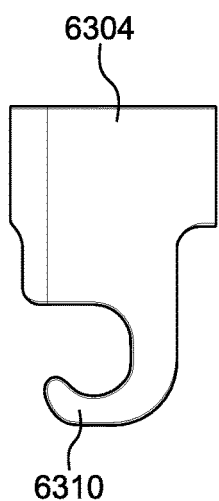
FIG. 36I is a left side of the tulip head connector shown in FIG. 36A.
Figure 37A:
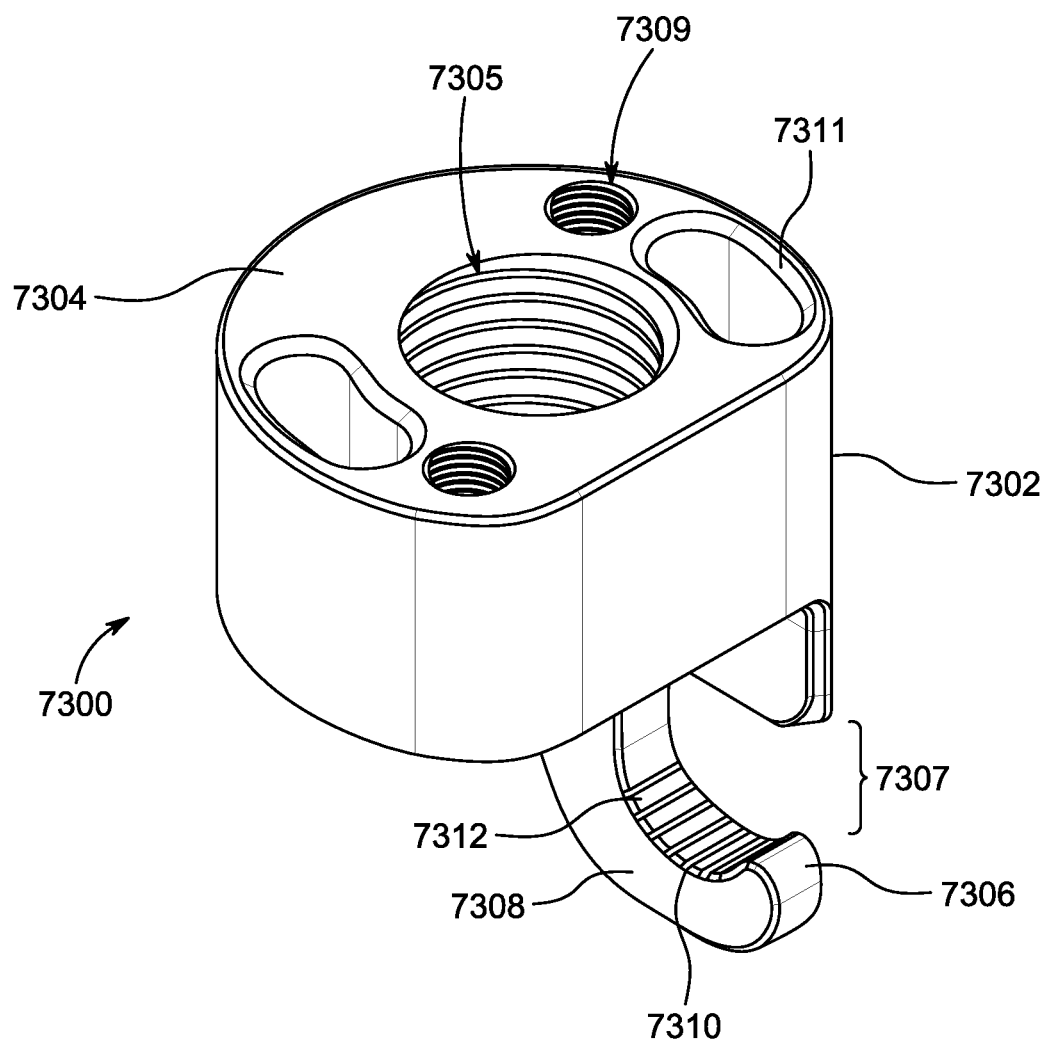
Figure 37B:
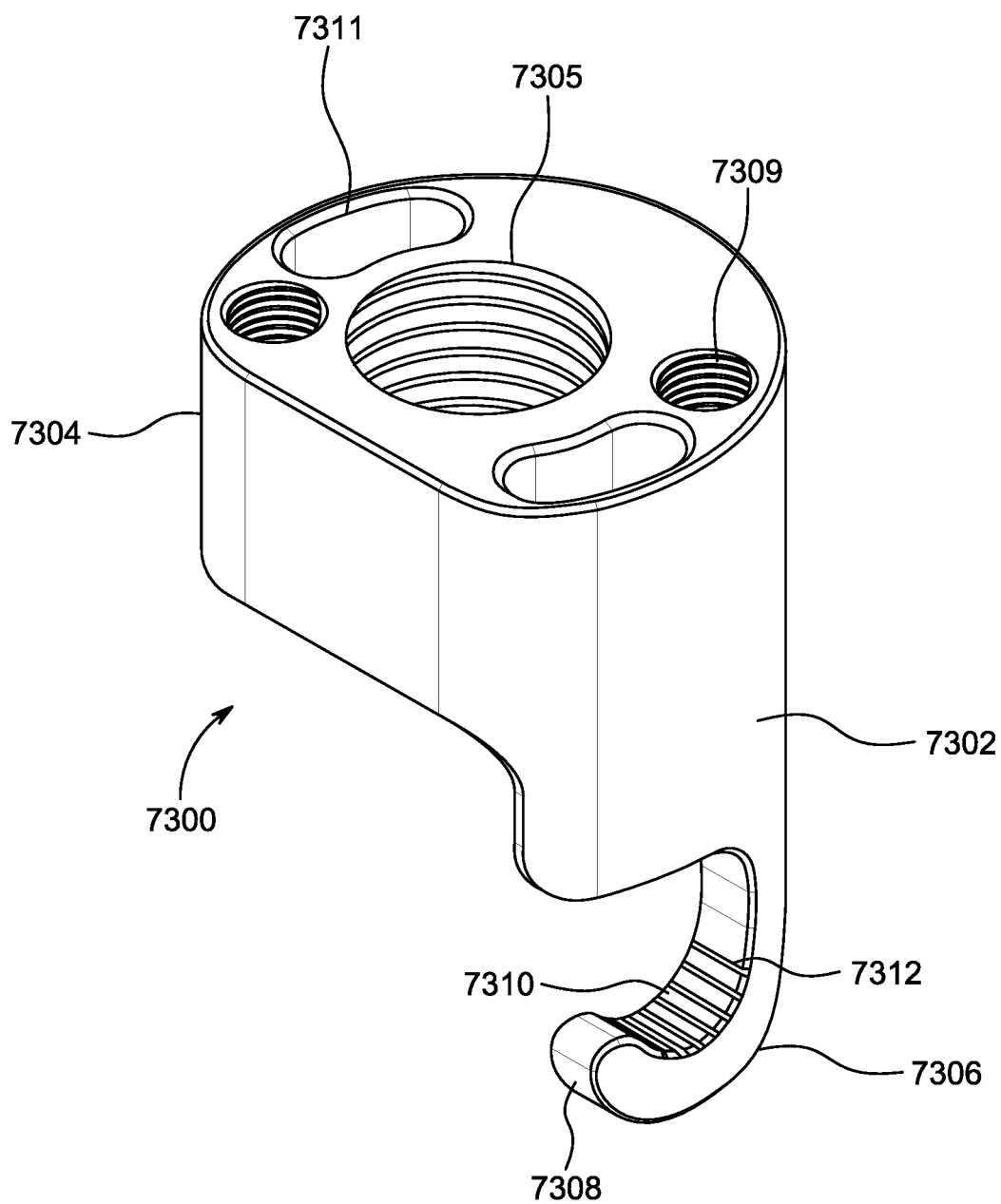
Figure 37C:
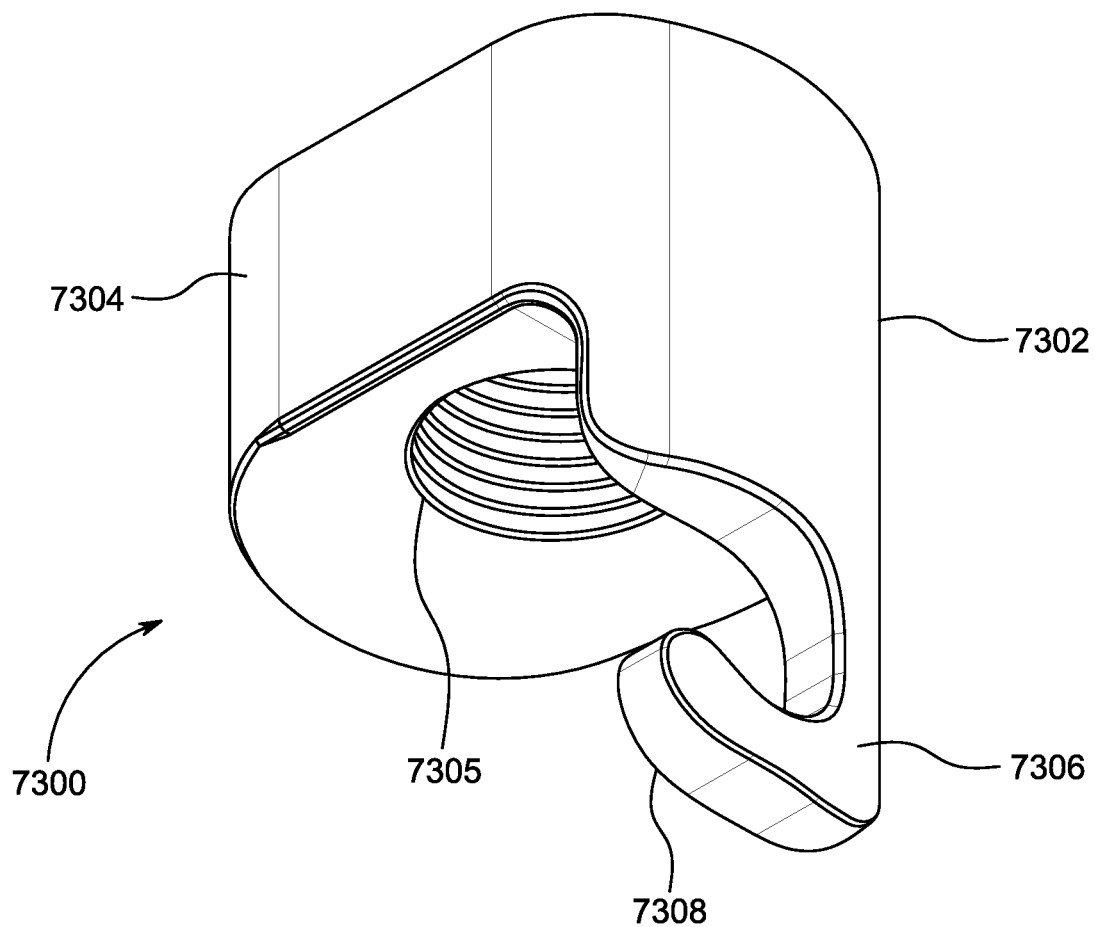
Figure 37D:
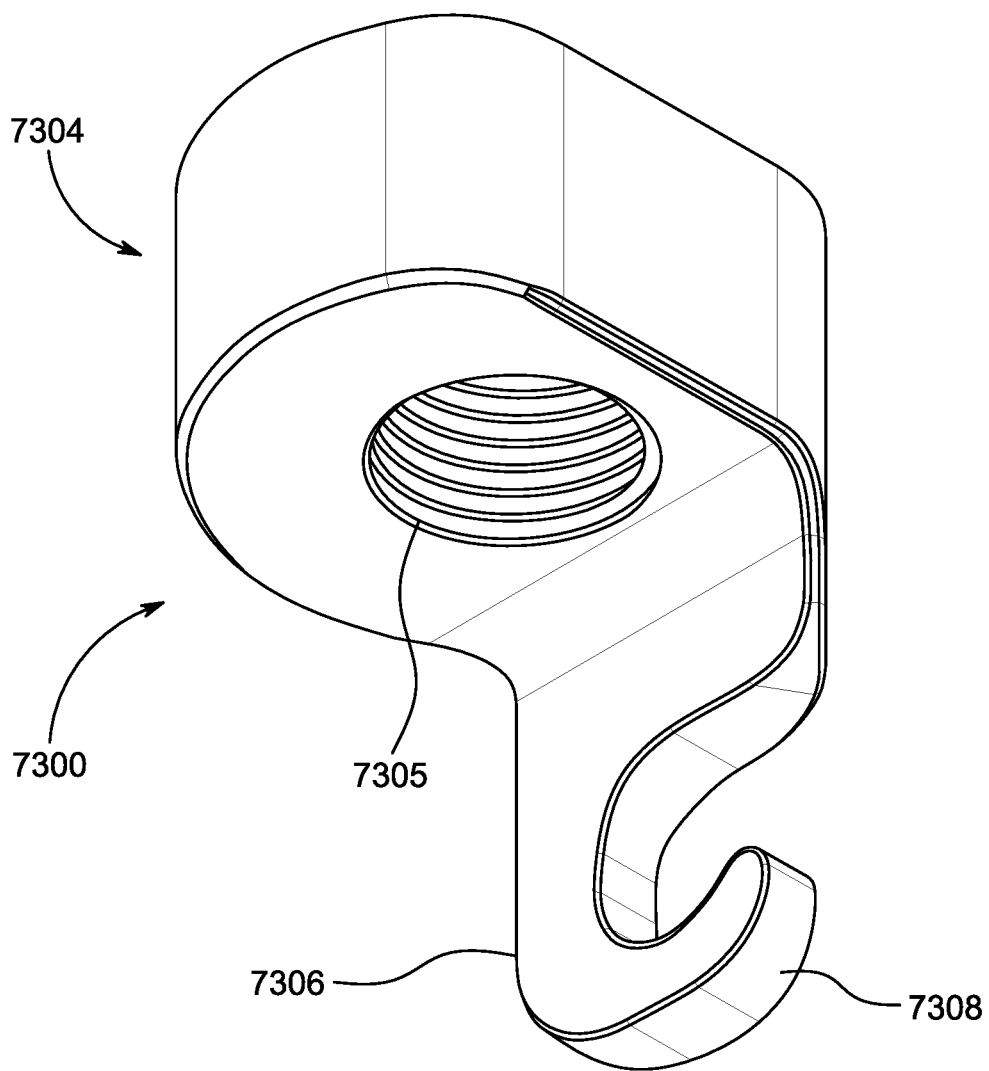
Figure 37E:
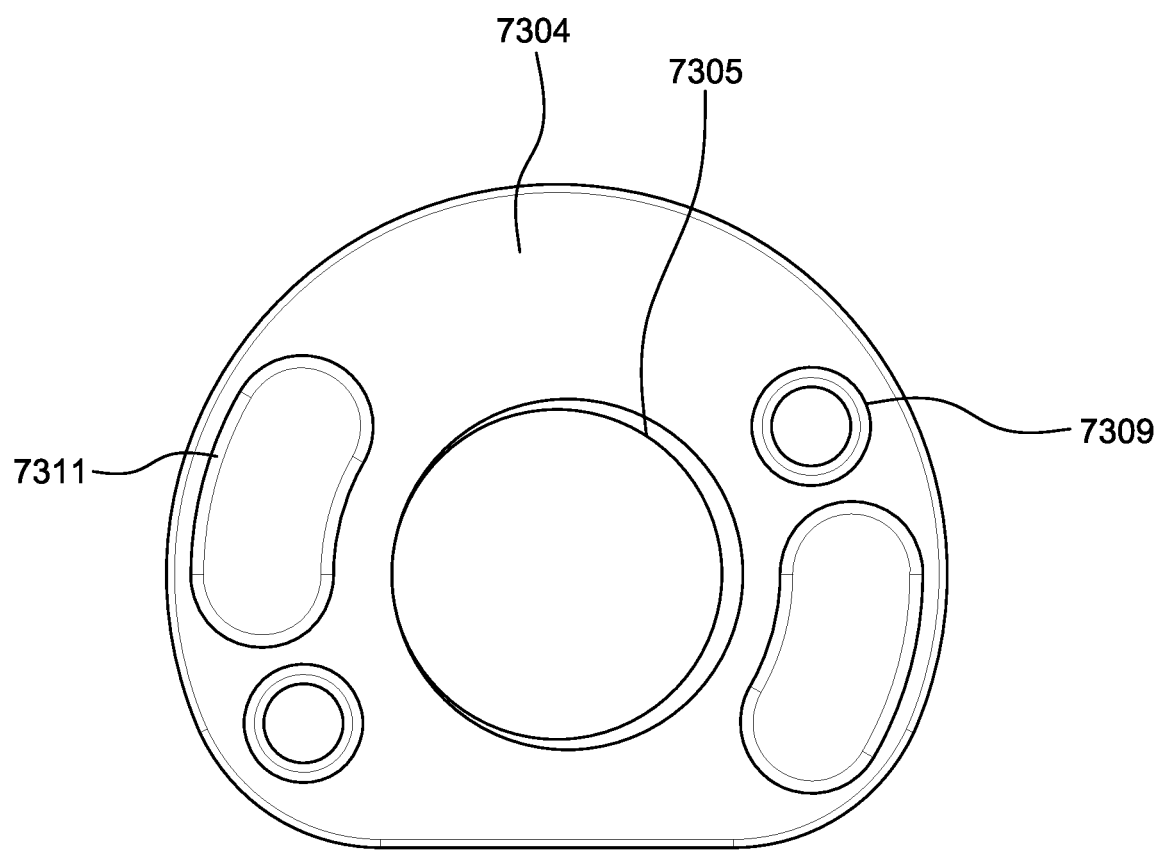
Figure 37F:
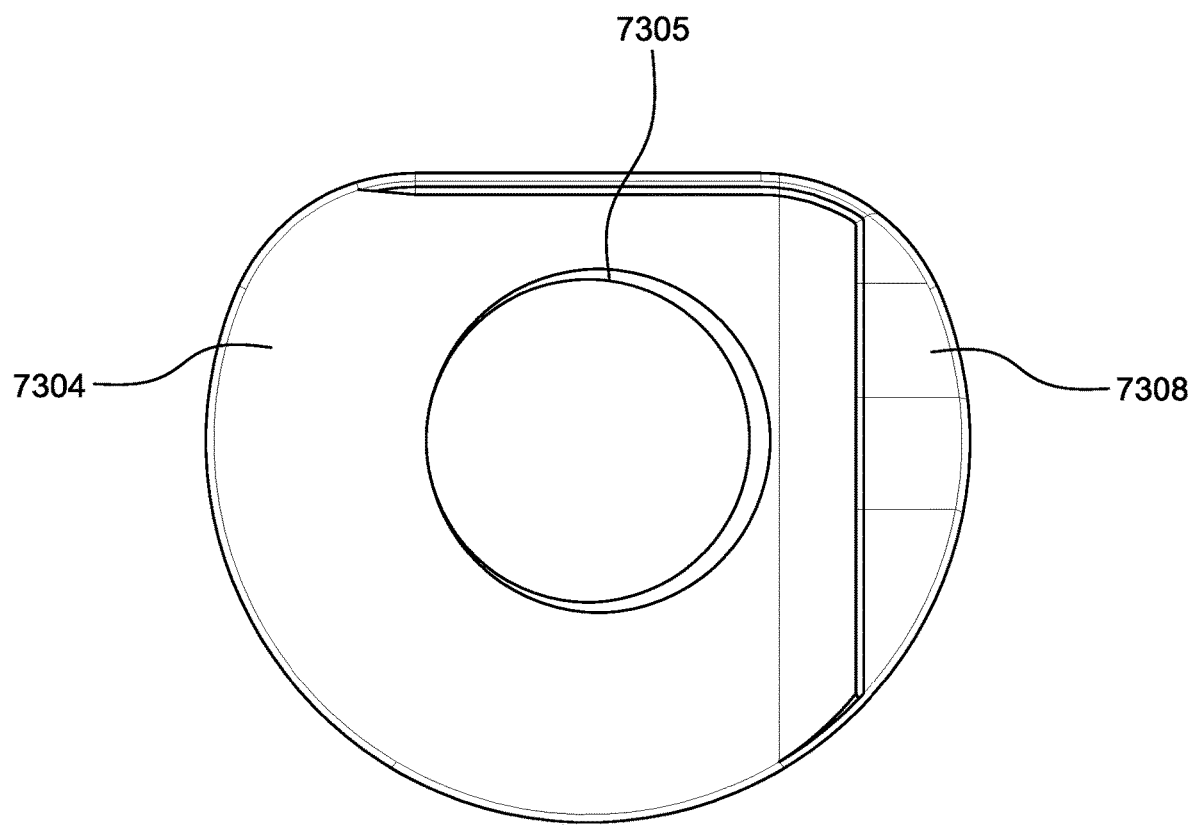
Figure 37G:
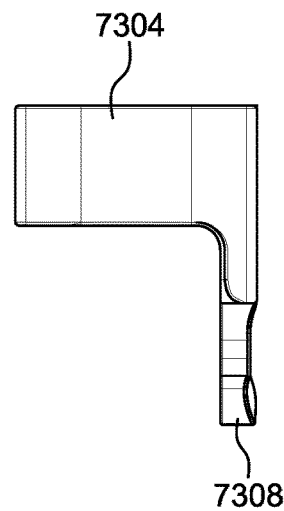
Figure 37H:
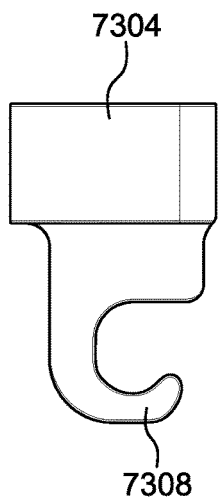
Figure 37I:
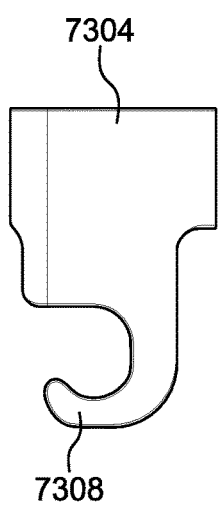

Referring to FIGS. 34A-34T, the tulip head connector 4300 is configured to engage with and secure to a previously implanted rod 22 and is fixed to an existing tulip head using set screw. The tulip head connector 4300 may comprise a main body 4302 having an upper portion 4304 configured to engage with pedicle screw set screw (threaded opening 4305), and a lower portion 4306 configured to engage with a preexisting surgical device, such as a previously implanted pedicle screw tulip 20 and rod 22. The tulip head connector main body upper portion 4304 is separated from the connector main body lower portion 4306 by a space or channel 4307. The space or channel 4307 is sized and shaped to allow an existing pedicle screw tulip 20 previously implanted into a patient to fit and or rest therein. The tulip head connector main body 4302 include arms 4308 and 4310. Arms 4308 and 4310 may include rod engagement portions, illustrated herein as indented curved surfaces (correspond to the curvature of the tulip head). A back wall 4316 may include a slotted channel 4318.

Referring to FIGS. 35A-35I, the tulip head connector 5300 is configured to engage with and secure to a previously implanted tulip head and/or retractor blade. Tulip head connector 5300 is sized and shaped to fit to an existing tulip head, fixed with a top set screw. The tulip head connector 5300 can be positioned in 4 positions on tulip head, and the retractor blade can be positioned in 3 different ways. The bottom can have 2 versions to fit both flat and curved tulip heads. The tulip head connector 5300 may comprise a main body 5302 having an upper portion 5304 configured to engage with pedicle screw set screw (threaded opening 4305), other screws (threaded opening 5309), and retractor blades (opening 5311), and a lower portion 5306 configured to engage with a preexisting surgical device, such as a previously implanted pedicle screw tulip 20. The tulip head connector main body upper portion 5304 is separated from the connector main body lower portion 5306 by a space or channel 5307. The space or channel 5307 is sized and shaped to allow an existing pedicle screw tulip 20 previously implanted into a patient to fit and or rest therein. The tulip head connector main body 5302 include arms 5308 and 5310. Arms 5308 and 5310 may include curved and/or angled surfaces 5312 and 5314 (correspond to the curvature of the tulip head). Arms 5308 and 5310 may include a knurled 5315 for use in gripping. A back wall 5316 may include a slotted channel 5318.

Referring to FIGS. 36A-36I, the tulip head connector 6300 is configured to engage with and secure to a previously implanted tulip head, rod, and/or retractor or traction blade. Tulip head connector 6300 is sized and shaped to fit to an existing tulip head, fixed with a top set screw. The tulip head connector 6300 may be fixed or secured to a rod, on both sides and a retractor or traction blade, in multiple directions. The tulip head connector 6300 may comprise a main body 6302 having an upper portion 6304 configured to engage with pedicle screw set screw (threaded opening 6305), other screws (threaded opening 6309), and retractor or traction blades (opening 6311), and a lower portion 5306 configured to engage with a preexisting surgical device, such as a previously implanted pedicle screw tulip 20. The tulip head connector main body upper portion 6304 is separated from the connector main body lower portion 6306 by a space or channel 6307. The space or channel 6307 is sized and shaped to allow an existing pedicle screw tulip 20 previously implanted into a patient to fit and or rest therein. The tulip head connector main body 6302 include arms 6308 and 6310. Arms 6308 and 6310 may include curved surfaces 6312 and 6314 (correspond to the curvature of the tulip head). Arms 6308 and 6310 may include a knurled 6315 for use in gripping.

Referring to FIGS. 37A-37I, the tulip head connector 7300 is configured to engage with and secure to a previously implanted tulip head, rod, and/or retractor or traction blade. Tulip head connector 7300 is sized and shaped to fit to an existing tulip head, fixed with a top set screw. The tulip head connector 7300 may be fixed or secured to a rod (right side), and a retractor or traction blade, in multiple directions. The tulip head connector 7300 may comprise a main body 7302 having an upper portion 7304 configured to engage with pedicle screw set screw (threaded opening 7305), other screws (threaded opening 7309), and retractor or traction blades (opening 7311), and a lower portion 7306 configured to engage with a preexisting surgical device, such as a previously implanted pedicle screw tulip 20. The tulip head connector main body upper portion 7304 is separated from the connector main body lower portion 7306 by a space or channel 7307. The space or channel. 6307 is sized and shaped to allow an existing pedicle screw tulip 20 previously implanted into a patient to fit and or rest therein. The tulip head connector main body 7302 includes right arms 7308. Arm 6308 may include curved surfaces 7310 (correspond to the curvature of the tulip head). Arms 7308 may include a knurled 7312 for use in gripping.

Referring to FIGS. 38A-38I, the tulip head connector 8300 is configured to engage with and secure to a previously implanted tulip head, rod, and/or retractor or traction blade. Tulip head connector 8300 is sized and shaped to fit to an existing tulip head, fixed with a top set screw. The tulip head connector 8300 may be fixed or secured to a rod (left side), and a retractor or traction blade, in multiple directions. The tulip head connector 8300 may comprise a main body 8302 having an upper portion 8304 configured to engage with pedicle screw set screw (threaded opening 8305), other screws (threaded opening 8309), and retractor or traction blades (opening 8311), and a lower portion 8306 configured to engage with a preexisting surgical device, such as a previously implanted pedicle screw tulip 20. The tulip head connector main body upper portion 8304 is separated from the connector main body lower portion 8306 by a space or channel 8307. The space or channel 8307 is sized and shaped to allow an existing pedicle screw tulip 20 previously implanted into a patient to fit and or rest therein. The tulip head connector main body 8302 includes right arms 8308. Arm 6308 may include curved surfaces 8310 (correspond to the curvature of the tulip head). Arms 8308 may include a knurled 8312 for use in gripping.

All patents and publications mentioned in this specification are indicative of the levels of those skilled in the art to which the invention pertains.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An add on surgical screw system for use in surgical procedures, comprising:
   a side to side bone screw connector constructed and arranged to engage with and secure to a preexisting implanted bone screw system having a preexisting screw head attached to an anatomical structure without having to remove any components of said preexisting implanted bone screw system, said side to side bone screw connector comprising a vertical body having a flange member at an upper end extending away from said vertical body, said flange member having an opening for receiving a top locking screw, and a preexisting screw head engaging member extending from said vertical body in the same direction as said flange member, said vertical body separating said flange member and said preexisting screw head engaging member by a distance to form a first space, said first space defining a preexisting implanted bone screw system receiving channel sized and shaped to receive and partially enclose therein said preexisting screw head of said preexisting implanted bone screw system, said preexisting screw head engaging member defined by a first member extending away from said vertical body in the same direction as said flange member and a second member extending away from said vertical body in the same direction as said first member, said second member separated from said first member by a second space, said vertical body having a length which positions said first member and said second member underneath said preexisting screw head when said side to side bone screw connector engages with said preexisting implanted bone screw system screw head;
   a secondary screw head support member comprising a horizontal body extending from said vertical body in a direction opposite of said first member and said second member of said preexisting screw head engaging member;
   a secondary screw head constructed and arranged to receive a secondary surgical rod, said secondary screw head secured to or formed from said secondary screw head support member horizontal body and having two threaded surfaces for receiving a set screw, and a base separating said two threaded surfaces, said base sized and shaped to receive said secondary surgical rod, wherein when said side to side bone screw connector engages or secures to said preexisting implanted bone screw system screw head, said secondary screw head is positioned in a side-by-side orientation with said preexisting implanted bone screw system screw head; and
   a locking screw constructed and arranged to fit within said flange member opening and secure to or engage with a preexisting set screw associated with said preexisting implanted bone screw system screw head.

2. The add on surgical screw system for use in surgical procedures according to claim 1, wherein said preexisting implanted bone screw system further includes a tulip, a spinal rod, one or more set screws, a threaded screw, or combinations thereof.

3. The add on surgical screw system for use in surgical procedures according to claim 1, wherein said secondary screw head support member horizontal body comprises an opening.

4. The add on surgical screw system for use in surgical procedures according to claim 1, wherein said flange member further comprises one or more additional openings.

5. The add on surgical screw system for use in surgical procedures according to claim 1, wherein said secondary screw head supports a pedicle screw, a facet screw, or a lateral mass screw.

6. The add on surgical screw system for use in surgical procedures according to claim 1, wherein said secondary screw head is a tulip head supporting a polyaxial screw.

7. The add on surgical screw system for use in surgical procedures according to claim 1, wherein said preexisting implanted bone screw system is a pedicle screw system, a facet screw system, or a lateral mass screw system.

8. A side to side screw head connector for engaging with or securing to a preexisting implanted bone screw system having a preexisting screw head secured to a bone structure, comprising:
   a vertical body comprising an upper end having a flange member having an opening for receiving a top locking screw and extending away from said vertical body, a bottom end, and a first space separating said flange member and said bottom end, said first space defining a preexisting implanted bone screw system receiving channel sized and shaped to receive and partially enclose therein said preexisting screw head of said preexisting implanted bone screw system, said vertical body separating said flange member and said bottom end;
   a preexisting screw head engaging member comprising a first member extending away from said vertical body, a second member extending away from said vertical body in the same direction as said first member, and a second space separating said first member from said second member, said vertical body having a length which positions said first member and said second member underneath said preexisting screw head when said side to side screw head connector engages with said preexisting implanted bone screw system;
a secondary screw head support member comprising a horizontal body extending from said vertical body in a direction opposite of said first member and said second member of said preexisting screw head engaging member; and
a locking screw constructed and arranged to fit within said flange member opening and secure to or engage with a preexisting set screw associated with said preexisting implanted bone screw system screw head.

9. The side to side screw head connector according to claim 8, further comprising a secondary screw head constructed and arranged to receive a secondary surgical rod, said secondary screw head comprising two threaded surfaces for receiving a set screw, and a base separating said two threaded surfaces, said base sized and shaped to receive said secondary surgical rod,
wherein when said side to side bone screw connector is secured to said preexisting implanted bone screw system screw head, said secondary screw head is arranged in a side-by-side orientation with said preexisting implanted bone screw system screw head.

10. The side to side screw head connector according to claim 9, wherein, said secondary screw head is secured to said secondary screw head support member body via a screw.

11. The side to side screw head connector according to claim 9, wherein said secondary screw head supports a pedicle screw system, a facet screw system, or a lateral mass screw system.

12. The side to side screw head connector according to claim 9, wherein said secondary screw head is a tulip head supporting a polyaxial screw system.

13. The side to side screw head connector according to claim 8, wherein said flange member further comprises one or more additional openings.

14. A side to side screw head connector for engaging with and securing to a preexisting implanted bone screw system having a preexisting screw head and a surgical rod secured to a portion of a bone structure without having to remove any components of said preexisting implanted bone screw system, comprising:
a side to side screw head connector vertical body comprising a flange member having an opening for receiving a top locking screw, said flange member extending away from said vertical body at a first end, a second end having a preexisting implanted bone screw system engaging member, said vertical body separating said flange member and said preexisting implanted bone screw system engaging member by a distance to form a first space, said first space sized and shaped to receive and partially enclose therein said preexisting screw head of said preexisting implanted bone screw system, said preexisting implanted bone screw system engaging member defined by a first member extending away from said vertical member and a second member extending away from said vertical member in the same direction as said first member, said second member separated from said first member by a second space, said second space of sufficient distance to position said first member along a first side of said preexisting screw head and said second member along a second side of said preexisting screw head when said side to side screw head connector engages with said preexisting implanted bone screw system screw head, said vertical body having a length which positions said first member and said second member under and in contact with said preexisting surgical rod when said side to side screw head connector engages with said pre-existing implanted bone screw system screw head or surgical rod;
a secondary screw head support member comprising a horizontal body extending from said vertical body in a direction opposite each member of said preexisting implanted bone screw system engaging member; and
a locking screw constructed and arranged to fit within said flange member opening and secure to or engage with a preexisting set screw associated with said preexisting implanted bone screw system screw head.

15. The side to side screw head connector according to claim 14, further comprising a secondary screw head constructed and arranged to receive a secondary surgical rod, said secondary screw head comprising two threaded surfaces for receiving a set screw, and a base separating said two threaded surfaces, said base sized and shaped to receive said secondary surgical rod,
wherein, when said side to side bone screw connector is secured to or engages with said preexisting implanted bone screw system screw head or surgical rod, said secondary screw head is arranged in a side-by-side orientation with said preexisting implanted bone screw system screw head.

16. The side to side screw head connector according to claim 15, wherein, said secondary screw head is secured to said secondary screw head support member horizontal body via a screw.

17. The side to side screw head connector according to claim 15, wherein said secondary screw head supports a pedicle screw system, a facet screw system, or a lateral mass screw system.

18. The side to side screw head connector according to claim 15, wherein said secondary screw head is a tulip head supporting a polyaxial screw system.

19. The side to side screw head connector according to claim 14, wherein said preexisting implanted bone screw system is a pedicle screw system, a facet screw system, or a lateral mass screw system.

20. The side to side screw head connector according to claim 14, wherein said flange member further comprises one or more additional openings.

* * * * *